United States Patent
Besseler et al.

(10) Patent No.: US 8,584,669 B2
(45) Date of Patent: Nov. 19, 2013

(54) INHALER

(75) Inventors: Jens Besseler, Dortmund (DE); Hubert Kunze, Dortmund (DE); Achim Moser, Chemnitz (DE); Ralf Thoemmes, Willich (DE); Gilbert Wuttke, Dortmund (DE); Dieter Hochrainer, Schmallenberg (DE); Heinrich Kladders, Mulheim-Ruhr (DE); Christoph Dworzak, Oberthal (CH); Josef Eckert, Mellrichstadt (DE); Antonio Lanci, Bern (CH); Markus Mast, Bern (CH); Elmar Mock, Colombier (CH); Andre Klopfenstein, La Neuveville (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1284 days.

(21) Appl. No.: 12/296,560

(22) PCT Filed: Apr. 11, 2007

(86) PCT No.: PCT/EP2007/003208
§ 371 (c)(1), (2), (4) Date: Jan. 22, 2009

(87) PCT Pub. No.: WO2007/118648
PCT Pub. Date: Oct. 25, 2007

(65) Prior Publication Data
US 2009/0194105 A1      Aug. 6, 2009

(30) Foreign Application Priority Data
Apr. 13, 2006   (EP) ................................. 06007767

(51) Int. Cl.
*A61M 13/00*     (2006.01)

(52) U.S. Cl.
USPC .................. 128/200.11; 128/200.4; 128/129; 128/153.02

(58) Field of Classification Search
USPC ..................... 128/200.11, 200.4, 129, 153.02
See application file for complete search history.

(56) References Cited

U.S. PATENT DOCUMENTS

| | | |
|---|---|---|
| 2,946,332 A | 7/1960 | Sacks |
| 3,507,277 A | 4/1970 | Altounyan |

(Continued)

FOREIGN PATENT DOCUMENTS

| | | |
|---|---|---|
| CA | 2 513 130 A1 | 7/2004 |
| DE | 103 00 982 A1 | 7/2004 |

(Continued)

OTHER PUBLICATIONS

International Search Report for PCT/EP2007/003208 mailed Aug. 13, 2007.

*Primary Examiner* — Jerome W Donnelly
(74) *Attorney, Agent, or Firm* — Michael P. Morris; Wendy A. Petka

(57) ABSTRACT

An inhaler (1) is proposed (see FIG. 1), for the inhalation of a formulation (2) from capsules (3) that each contain one dose of the formulation. The capsules are preferably each emptied in a capsule chamber (4) by being set in motion by a stream of air flowing through the capsule chamber. The stream of air can be generated by the inhalation of a user or patient and/or can be generated actively generated by the inhaler. For simple handling, the inhaler has a means for, in particular, automatic filling, emptying and/or cleaning of the capsule chamber, if the latter is used more than once. Alternatively, the inhaler has a large number of capsule chambers that each preferably already contain a capsule and re preferably used just once.

17 Claims, 49 Drawing Sheets

(56) References Cited

U.S. PATENT DOCUMENTS

| | | | |
|---|---|---|---|
| 3,518,992 A | 7/1970 | Altounyan | |
| 3,669,113 A | 6/1972 | Altounyan | |
| 3,837,341 A | 9/1974 | Bell | |
| 3,906,950 A | 9/1975 | Cocozza | |
| 3,991,761 A | 11/1976 | Cocozza | |
| 4,013,075 A | 3/1977 | Cocozza | |
| 4,117,844 A | 10/1978 | James | |
| 4,353,365 A | 10/1982 | Hallworth | |
| 4,524,769 A | 6/1985 | Wetterlin | |
| 4,570,630 A | 2/1986 | Elliott | |
| 4,778,054 A * | 10/1988 | Newell et al. | 206/531 |
| 4,811,731 A | 3/1989 | Newell | |
| 5,035,237 A * | 7/1991 | Newell et al. | 128/203.15 |
| 5,042,472 A | 8/1991 | Bunin | |
| 5,366,122 A | 11/1994 | Guentert et al. | |
| 5,595,175 A | 1/1997 | Malcher et al. | |
| 7,219,665 B1 * | 5/2007 | Braithwaite | 128/203.21 |
| 7,231,920 B2 | 6/2007 | Harvey | |
| 7,318,436 B2 * | 1/2008 | Snow | 128/203.21 |
| 7,571,723 B2 * | 8/2009 | Braithwaite | 128/203.21 |
| 2004/0099676 A1 | 5/2004 | Harvey | |
| 2004/0198708 A1 | 10/2004 | Kaplan et al. | |
| 2004/0236282 A1 | 11/2004 | Braithwaite | |
| 2005/0056280 A1 | 3/2005 | Alston et al. | |
| 2005/0172961 A1 | 8/2005 | Nesbitt | |

FOREIGN PATENT DOCUMENTS

| | | |
|---|---|---|
| EP | 0 388 621 A1 | 9/1990 |
| EP | 0 406 893 A1 | 1/1991 |
| EP | 0 530 625 A1 | 3/1993 |
| EP | 0 666 085 A1 | 8/1995 |
| EP | 1 145 728 A1 | 10/2001 |
| EP | 1 462 138 A1 | 9/2004 |
| FR | 1471722 A | 3/1967 |
| GB | 1122284 A | 8/1968 |
| GB | 1182779 A | 3/1970 |
| GB | 2061735 A | 5/1981 |
| JP | 63006024 B | 2/1988 |
| JP | 1027750 B | 5/1989 |
| JP | 1041343 B | 9/1989 |
| JP | 1047190 B | 10/1989 |
| JP | 3018376 A | 1/1991 |
| JP | 5077432 B | 10/1993 |
| JP | 5077433 B2 | 10/1993 |
| JP | 9262295 A | 10/1997 |
| JP | 2004512147 A | 4/2004 |
| WO | 92/03175 A1 | 3/1992 |
| WO | 0236189 A1 | 5/2002 |
| WO | 03/066470 A1 | 8/2003 |
| WO | 2005/049121 A1 | 6/2005 |

* cited by examiner

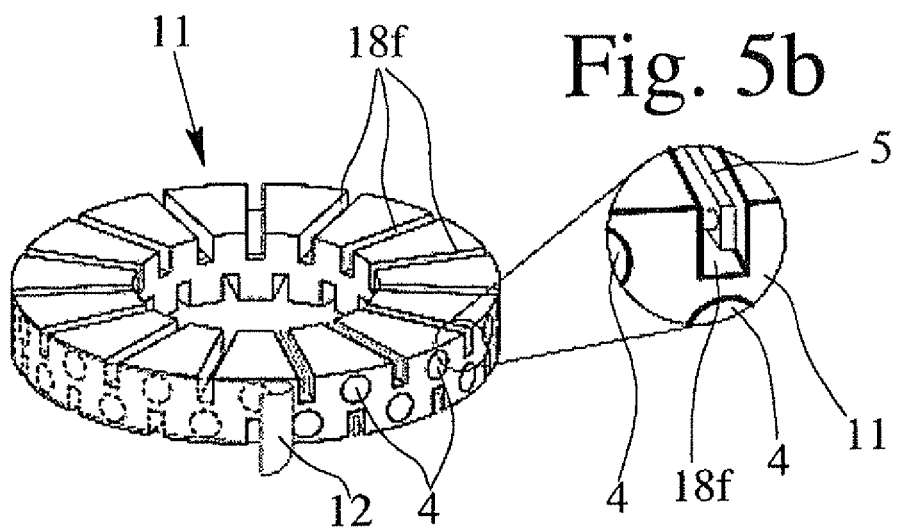
Fig. 5a
Fig. 5b
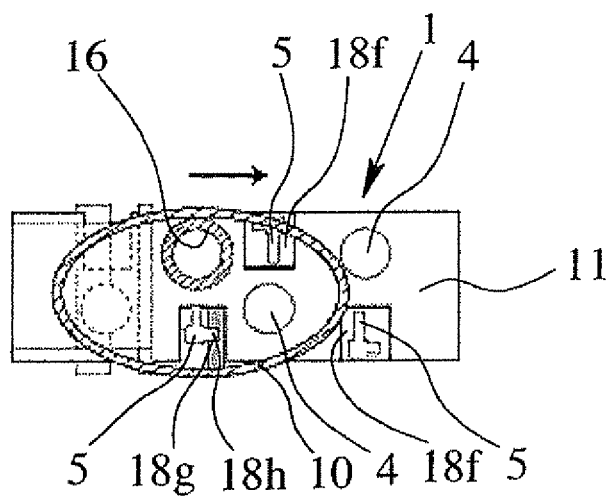
Fig. 5c

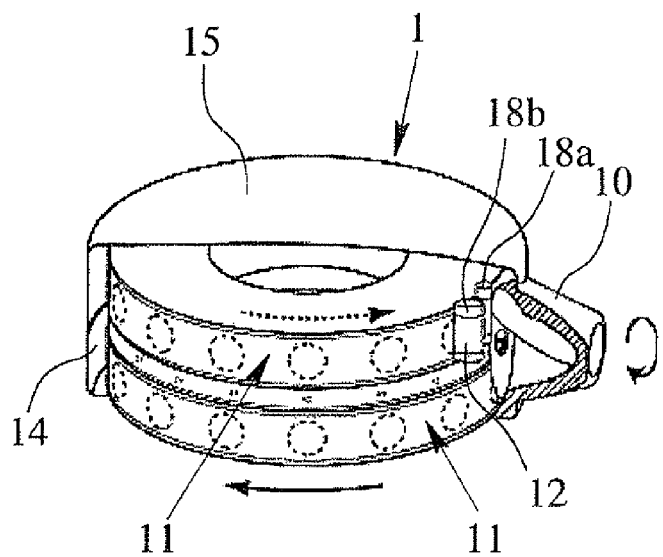
Fig. 6a
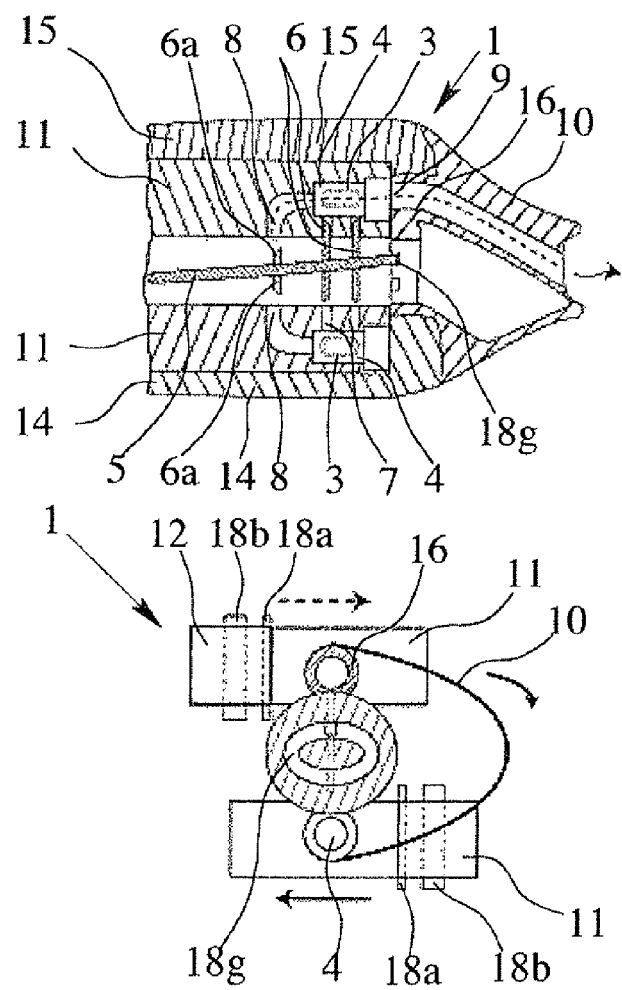
Fig. 6b
Fig. 6c

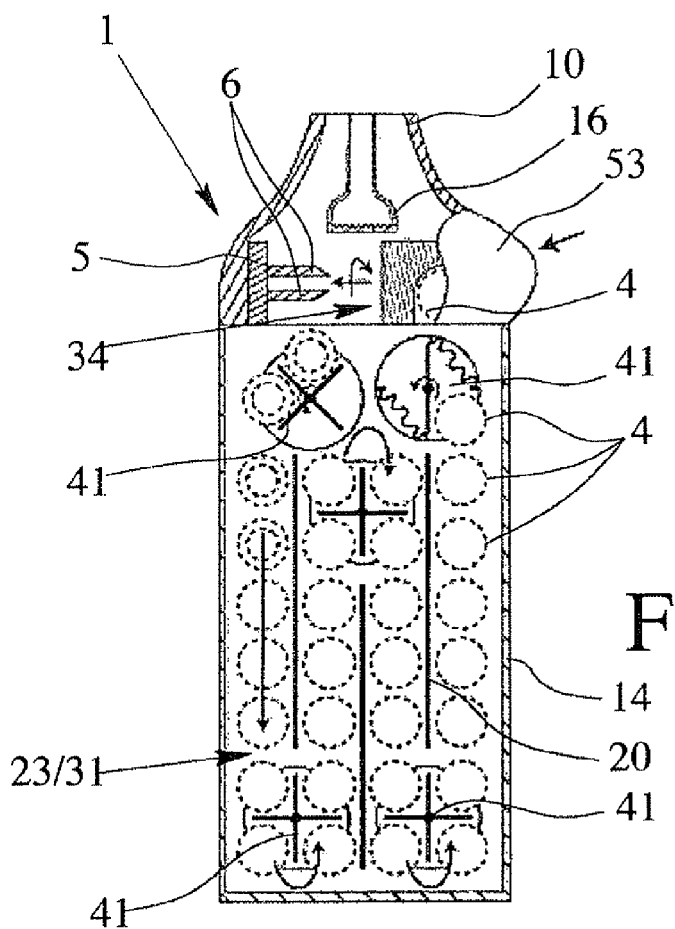
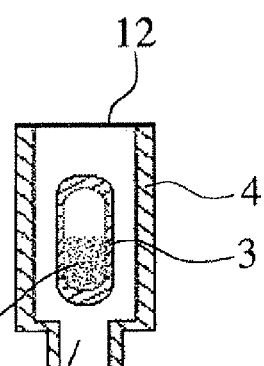
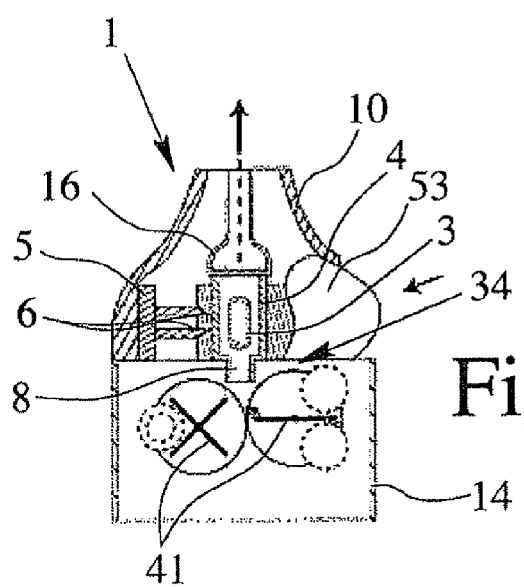
Fig. 38a
Fig. 38b
Fig. 38c

INHALER

This application is the national phase entry under 35 U.S.C. §271 of International Application No. PCT/EP2007/003208, filed Apr. 11, 2007, which claims priority to European Application No. EP 06007767.4, filed Apr. 13, 2006, each of which is hereby incorporated by reference in its entirety.

The present invention relates in particular to an inhaler for the delivery or inhalation of a preferably powdered formulation, i.e. a powder inhaler. However, the formulation may theoretically also be in liquid phase, a dispersion or in some other fluidisable form.

The formulation is, in particular, a therapeutic agent or medicament. In particular, the formulation accordingly contains at least one active substance or consists thereof. The formulation thus serves particularly for medical treatment or other therapeutic purposes.

In the present invention the formulation is contained in capsules, each capsule containing one dose of the formulation. The formulation is thus pre-dosed into the capsules.

In the present invention the term "capsule" refers primarily to containers having a solid or at least substantially rigid, more particularly leak-tight, one-piece, sealed and/or pervious coating which can be handled and/or opened, in particular, separately from one another. In another sense, according to the present invention the term "capsule" preferably also refers to other containers, packaging or the like containing one dose of the formulation, which are to be handled and/or opened in particular separately from one another.

EP 0 147 755 A2 discloses an inhaler for inhaling powdered medicaments from elongate capsules. The inhaler comprises a capsule chamber into which a capsule can be inserted manually. The capsule is pierced along its longitudinal side and thus opened by manual actuation of an opening device in the capsule chamber. During inhalation, an air current flowing through the capsule chamber causes the capsule to move back and forth in the capsule chamber, causes the capsule to move back and forth in the capsule chamber, as a result of which the powdered medicament is expelled and dispersed in the air current. The present invention makes use of this principle, in particular, but can also be used in other methods of delivering a formulation.

Moreover, an inhaler known as the "inhaler M" made by Boehringer Ingelheim Pharma GmbH & Co KG, Ingelheim, Germany, is known, which operates according to EP 0 147 755 A2 and comprises a rotatable carrier having six capsule chambers which can be filled manually with capsules.

WO 2005/049121 A1 discloses a portable capsule device which can in particular be inserted in a powder inhaler, for holding a plurality of capsules. The cylindrical capsules are guided in an upright position one behind the other by a rail or are joined together in the manner of a chain.

Other inhalers are known, for example, from WO 92/03175 A1, EP 0 406 893 A1 or U.S. Pat. No. 5,048,514 A, U.S. Pat. No. 5,595,175 A, US 2004/198708 A1, EP 0 666 085 A1 or U.S. Pat. No. 5,673,686 A and DE 103 00 982 A1 or CA 2,513,130 A1.

US 2004/0236282 A1 discloses a container for a powdered medicament, particularly for a powder inhaler. The container has a coil member for each dose, this coil member being surrounded by a sleeve. The particular dose is received in the annular space between the coil member and sleeve. The sleeve together with the coil member is accommodated in a sealed envelope. When the seal is open the sleeve is moveable relative to the coil member, thus releasing the powder. This container does not constitute a sealed capsule in a capsule chamber in the sense of the present invention.

The aim of the present invention is to provide an inhaler which allows easy handling, has a simple or compact construction, ensures particularly accurate dosing, particularly reliable or complete delivery of the formulation and/or multiple use without the manual insertion of new capsules.

A capsule chamber in the sense of the present invention is preferably an at least substantially rigid or solid and/or elongate container having an in particular elongate or cylindrical chamber in which the particular capsule can be moved back and forth in particular or set vibrating or oscillating in order to empty it.

Individual aspects, features, properties and advantages of the present invention will become apparent from the claims and the following description of preferred embodiments and variants by reference to the drawings, wherein:

BRIEF DESCRIPTION OF THE DRAWINGS

FIG. 3b shows a schematic view of the opening of the carrier according to FIG. 3a;

FIG. 4b is a schematic section through a detail of the inhaler according to FIG. 4a;

FIG. 5a is a schematic view of a carrier of the inhaler according to another embodiment;

FIG. 5b is a schematic magnification of FIG. 5a;

FIG. 5c is a schematic section or side view of the inhaler with the carrier according to FIG. 5a;

FIG. 6a is a schematic, partially cut away view of the inhaler according to another embodiment;

FIG. 6b is a schematic section through a detail of the inhaler according to FIG. 6a;

FIG. 6c is a schematic lateral functional view of the inhaler according to FIG. 6a;

FIG. 8b is a schematic section through the inhaler according to FIG. 8a;

FIG. 8c is another schematic section through the inhaler according to FIG. 8a;

FIG. 15c is a schematic view of a part of the capsule chamber of the opening device or the capsule chamber of the inhaler according to FIG. 14a;

FIG. 38a shows a schematic section through the inhaler according to another embodiment;

FIG. 38b shows a schematic section through a capsule chamber of the inhaler according to FIG. 38a;

FIG. 38c shows a detailed section of the inhaler according to FIG. 38a;

Figure 1:
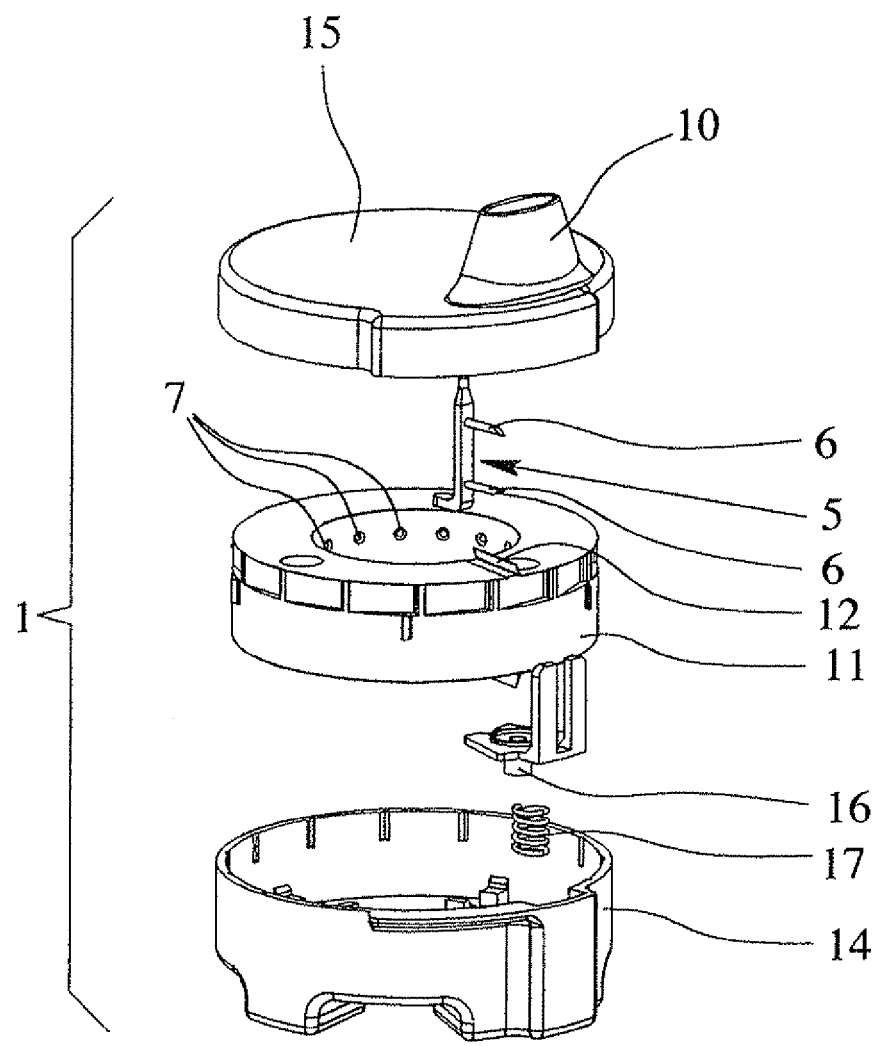
FIG. 1 shows a schematic exploded view of an inhaler according to a preferred embodiment.

In the figures, the same reference numerals have been used for identical or similar parts, even if the related description has not been repeated. In particular, the same or corresponding advantages and properties are obtained. The individual figures are mostly not drawn to scale for reasons of representation or simplicity.

FIG. 1 schematically shows, in a perspective exploded view, the structure of a proposed inhaler 1 according to a preferred embodiment. The inhaler 1 is preferably constructed to be portable and operates purely mechanically, in particular.

Figure 2:
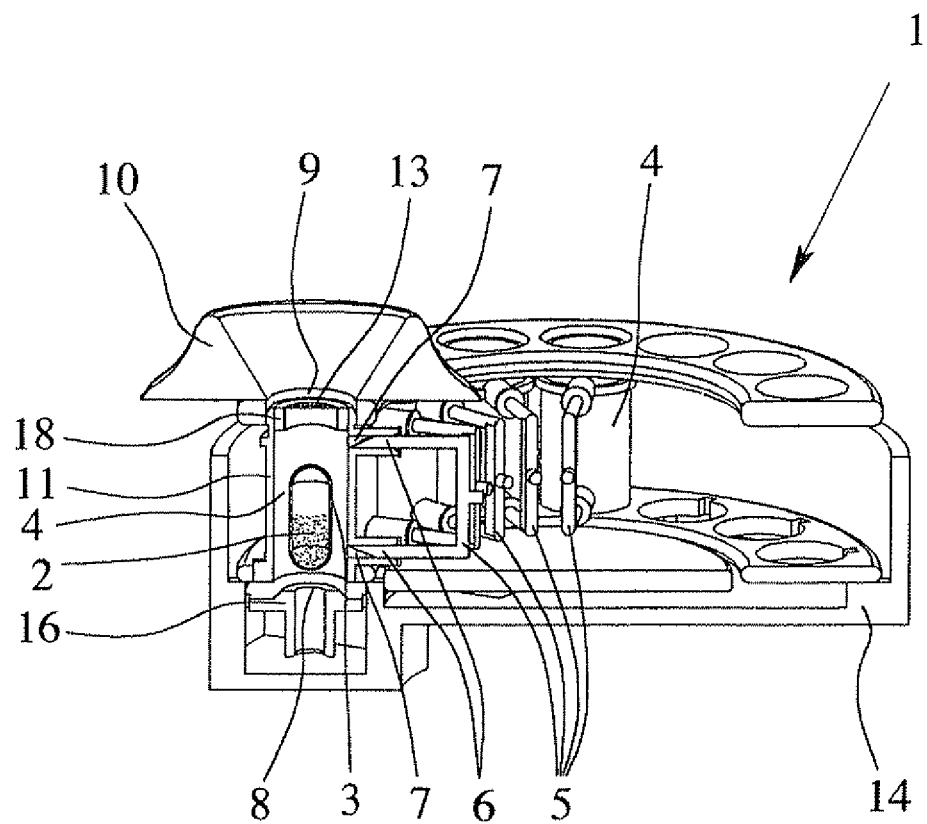
FIG. 2 shows a schematic section of a detail of the inhaler according to FIG. 1.

FIG. 2 shows in schematic section the assembled inhaler 1 for inhaling a preferably powdered formulation 2 in the sense described hereinbefore from capsules 3.

In the schematic section, a capsule 3 is shown inside a capsule chamber 4 of the inhaler 1. The capsule 3 is still sealed, i.e. not yet opened.

The capsules 3 are preferably of elongate construction. However, theoretically, the capsules 3 may also be of any other suitable shape and may for example be spherical.

The capsules 3 may theoretically be made from or consist of any suitable material. Preferably, gelatine is used as the capsule material. In this case it may be used in admixture with other additives selected from among polyethyleneglycol (PEG), preferably PEG 3350, glycerol, sorbitol, propyleneglycol, PEO-PPO block copolymers and other polyalcohols and polyesters. It is particularly preferable to use gelatine in admixture with PEG, preferably PEG 3350. Particularly preferably, a gelatine capsule 3 contains PEG in an amount of from 1 to 10% (by weight), preferably 3 to 8%. Particularly preferred gelatine capsules 3 contain PEG in an amount of from 4 to 6%, a PEG content of around 5% being most preferred. In the case of gelatine-containing capsule materials, the capsules 3 preferably have a TEWS or halogen dryer moisture content of less than 12%, most preferably <10%.

If cellulose derivatives are used as the capsule material it is preferable to use hydropropylmethylcellulose, hydroxypropylcellulose, methylcellulose, hydroxymethylcellulose and hydroxyethylcellulose. It is particularly preferable in this case to use hydroxypropylmethylcellulose (HPMC), most preferably HPMC 2910 as the capsule material. If cellulose derivatives are used as capsule materials the degree of TEWS or halogen dryer moisture is preferably less than 8%, most preferably less than 5%. It is most preferably for inhalation capsules 3 made of cellulose derivatives to be dried to a TEWS or halogen dryer moisture content of less than 4%, most preferably less than 2%, before being filled with a tiotropium-containing inhalable powder.

Suitable plastic materials for the capsules 3 are any pharmaceutically acceptable plastics which can be processed by injection or blow moulding and deep drawing by thermoforming and/or plastics which do not require a mould release agent in order to process them to form the capsule cap or capsule body, as the mould release agent may cause the contents to stick to the capsule wall. The plastic should also not have any marked adhesion to pharmaceutical chemical substances, particularly particles of a size intended for the lungs. The preferred Shore hardness D of the materials is preferably between 10 and 85, preferably between 55 and 75, most preferably between 60 and 70. The material should also be such that a plastic capsule 3 will withstand a force of preferably up to 20 N along its longitudinal axes. Moreover, the wall of the capsule 3 should have a permeability to water vapour of less than $1.3\times10^{-14}$ kg/($m^2$s Pa), preferably $1.5\times10^{-16}$ kg/($m^2$s Pa). The melt viscosity MFR (melt flow rate) is preferably between 40 and 65 g/10 minutes, preferably 45-49 g/10 minutes and most preferably 52 g/10 minutes.

The capsules 3 may each consist of a capsule body and a capsule cap, as disclosed particularly in WO 00/07572 A2. Therefore explicit reference will hereby be made to the contents of WO 00/07572 A2 in their entirety. In this two-part structure, plastic is used as the capsule material, in particular. The capsule body and the capsule cap, in particular, consist of the same material. They are joined together so as to form a stable sealed cavity of a defined volume. It is particularly preferable to use plastics, particularly polyethylene. The capsule 3 may have latching elements that firmly attach the capsule cap to the capsule body.

To open it, the inhaler 1 has an opening device 5, particularly a plurality of opening devices 5, each associated with a capsule chamber 4 or a capsule 3. In particular, in the embodiment illustrated, the capsule 3 is opened laterally. For this purpose the preferably elongate capsule 3 is capable of being pierced and thus opened along its longitudinal side or laterally and/or at right angles to the main direction of flow by at least one piercing element 6—or two piercing elements 6 in the embodiment shown—of the respective opening device 5. The capsule chamber 4 preferably has corresponding piercing openings 7 for the piercing elements 6. Preferably the piercing elements 6 remain in position in the pierced openings 7 and seal them. This position is occupied by the opening device 5 in particular after the capsule 3 has been opened and during inhalation.

Associated with the capsule chamber 4 are an inlet 8 and an outlet 9 which are connected, in particular axially or at the end faces to the preferably elongate or cylindrical capsule chamber 4. Preferably the geometric dimensions correspond to the data in EP 0 147 755 A2, which is cited as an additional disclosure on this subject.

During inhalation, air or some other gas flows through the inlet 8 into the capsule chamber 4, through the chamber and out of the preferably opposite outlet 9. This flow of air or gas can be produced by breathing in during inhalation and/or by a pressure generator associated with the inhaler 1 and not shown here, such as an air pump, a pressurised gas reservoir or the like.

As a result of the Bernoulli effect, in particular, the flow of air through the capsule chamber 4 causes the capsule 3 to move axially back and forth or vibrate or oscillate, in particular, in the capsule chamber 4. This causes or assists with the expulsion of the formulation 2 from the opened capsule 3 into the air current—particularly in the form of very fine particles—and dispersion of the formulation in the air current by which the formulation 2 is expelled through the outlet 9 and delivered in particular through an adjoining mouthpiece 10 to a user or patient (not shown). The delivery or dispersion of the formulation 2 takes place in particular as described in EP 0 147 755 A2, which is incorporated to this end as a supplementary disclosure. However, the formulation 2 may theoretically also be expelled from the capsule 3 by any other suitable means.

In the present embodiment the inhaler 1 has a plurality of capsule chambers 4, each of which is filled with a capsule 3 and is used only once, in particular. There is no refilling or changing of the capsules 3, in particular. This means that the carrier 11 can be fitted with the capsules 3 in the factory, so that there is no need for the user or patient to insert the capsules 3 manually or handle them.

The proposed inhaler 1 preferably has only one opening device 5. If necessary, however, the inhaler 1 may also have a plurality of opening devices 5, particularly so that each capsule chamber 4 has its own separate opening device 5 associated with it or the capsule chambers 4 or capsules 3 are associated with separate or different piercing elements 6 or the like, as shown in FIG. 2. In this case the opening devices 5 can preferably be controlled or actuated by means of a cam, slide or other device, as necessary. In the embodiment shown the opening devices 5 or the piercing elements 6 are moved along with the capsule chambers 4 or carriers 11 and preferably cannot be detached from them.

Preferably, the capsules 3 and capsule chambers 4 are arranged in a ring. In particular, the capsule chambers 4 are formed on or by a common, preferably annular carrier 11 (cf. FIG. 1 and FIG. 3*a*). The carrier 11 can be replaced if necessary. In this case the inhaler 1 can be used a number of times, i.e. with a number of carriers 11.

In the present embodiment a plurality of capsules 3 are accommodated in the carrier 11 and a corresponding number of capsule chambers 4 are formed.

Each capsule 3 preferably contains one dose of the formulation 2. As the carrier 11 may contain a plurality of capsules 3 and hence a corresponding number of doses, the inhaler 1 may ensure a supply of the formulation 2, i.e. a medicament or the like, to a user or patient for a week or several weeks or even a month, for example.

The capsule chambers 4 are preferably closed off, particularly so as to be fluid-tight and are preferably also gas-tight. For example, the carrier 11 is provided for this purpose with an optionally continuous cover 12 on both end faces so that the inlets 8 on the one hand and the outlets 9 on the other hand—and any lattices 13 inserted or arranged therein—are covered and closed off. The cover 12 is, in particular, a suitable seal, foil or the like.

In the embodiment shown the cover 12 is preferably in the form of a strip or of a continuous design. However, if necessary, separate covers may also be provided for the individual capsule chambers 4 or inlets 8 and/or outlets 9. A segmental design of the cover 12 is also possible, for example.

Preferably, the piercing openings 7 are also closed initially, for example by means of wall sections, plugs, covers, not shown here, and possibly also by the cover or covers 12 or the like.

The capsule chambers 4 with the capsules 3 arranged therein are accordingly preferably hermetically sealed. This allows lengthy storage as the capsules 3 are optimally protected from environmental influences, particularly severe changes in relative humidity or pollution.

In the embodiment shown the inhaler 1 has a lower housing part 14 particularly for accommodating the carrier 11 and an upper housing part 15 particularly with the mouthpiece 10 as a cover.

In the assembled inhaler 1, the carrier 11 can be advanced stepwise so that the capsule 3 or capsule chamber 4 intended for the next inhalation is moveable into an inhaling position, in this case underneath the mouthpiece 10. During movement into this position, in this case by the rotation of the carrier 11, the capsule chamber 4 moving into the position of inhalation is preferably opened individually, for example by pulling off the cover or covers 12 from the respective inlet 8 and outlet 9. This is preferably done automatically by a corresponding mechanism, device or the like in the inhaler 1. Alternatively, the opening of the inlet 8 and outlet 9 may only occur in the position of inhalation.

The preferably individual opening of the capsule chambers 4 may be carried out, for example, by successively pulling or peeling off, rolling up or coiling the cover or covers 12. However, the cover 12 or each capsule chamber 4 may also be opened by any other suitable method. For example it is also possible to pull, press, peel or otherwise move, remove or detach the cover 12 radially inwards or outwards and/or in the axial direction, particularly in the annular arrangement as provided in the first embodiment.

If required, the cover 12 may be stuck back again after the removal or detachment, for example it may be reattached to the carrier 11 or another suitable part of the inhaler 1. For example, the removed cover 12 may also serve to close up the piercing openings 7 in order to ensure the desired passage of air during inhalation. For this purpose, the pulled off cover 12 may for example be stuck down over the respective piercing openings 7.

In the embodiment shown the inhaler 1 comprises a connector 16 that forms the inlet 8 or is adjacent thereto and which can be biased and/or applied particularly by its spring force, in this case by an axially acting spring 17, against the capsule chamber 4 on the air supply side in the inhalation position. If necessary the connector 16 may also effect the opening of the respective connecting chamber 11 at the same time, if suitably configured.

On the outlet side, a corresponding manner or some other suitable manner, the mouthpiece 10 with the outlet 9 or an outlet channel or connector can be connected to the respective capsule chamber 4 in the inhalation position, preferably applied thereto, particularly so that when the user breathes in a sufficient flow of air is produced or sucked through the capsule chamber 4 to set the capsule 3 in motion in the capsule chamber 4 in the desired manner and in particular to bring about or assist with the delivery of the formulation 2 in this way.

During the inhalation or expulsion of the formulation 2, the opening device 5 preferably closes off the piercing openings 7 with its piercing elements 6, as shown in FIG. 2, to ensure the desired flow of air from the inlet 8 to the outlet 9. After inhalation, the opening device 5 is pulled completely out of the pierced openings 7 so that the carrier 11 can be rotated further and in this way the next capsule chamber 4 can be moved into the inhaling position.

However, the piercing openings 7 can be resealed, at least temporarily for inhalation, in any suitable manner after the piercing or opening of the capsule 3. For example, the piercing openings 7 may be formed to be self-sealing by means of a septum (not shown) associated therewith or, may be closed off, at least in the region of the inhaling position after the piercing of the capsule 3, by a suitable closure element such as a stopper, a pressable seal or the like.

For advancing the carrier 11, for the coordinated actuation of the opening device 5 and/or for opening the respective capsule chamber 4, a suitable, more particularly shared mechanism or the like is preferably provided, not shown here. In particular, the inhaler 1 is actuated manually.

If the mechanism is suitably designed, handling is particularly easy. In particular, there is no need for individual capsules 3 to be inserted manually into the respective capsule chamber 4. Moreover, if suitably designed, the actuation of a single actuating element may be sufficient to perform all the functions, namely advancing the next capsule chamber 4 with capsule 3 into the inhaling position, opening the capsule chamber 4 and opening the capsule 3.

One advantage of the proposed inhaler 1 is that empty or used capsules 3 and used capsule chambers 4 do not have to be expelled and disposed of but are contained within the inhaler 1 and remain therein. This makes their handling very simple and enables them to be used universally.

In the present embodiment the capsules 3 and/or capsule chambers 4 are preferably aligned at right angles to the direction of movement and/or parallel to one another and/or at least substantially axially. According to FIG. 4, 5 or 6, however, the capsules 3 and/or capsule chambers 4 may also be aligned radially. This allows the inhaler 1 to have a particularly low overall height. If necessary the capsule chambers 4 and/or capsules 3 can be pivoted out of the radial position into the axial position for inhalation or in the inhalation position, particularly if the carrier 11 is constructed accordingly.

The forgoing explanations apply accordingly to the capsules 3 if they are not initially arranged in capsule chambers 4 but are supplied one after the another to a capsule chamber 4, for example.

Generally, instead of the cover 12, it is also possible to use other closures or the like such as stoppers, covers, gates, a preferably rotatable shutter, slide, sleeve or the like, to close off the capsule chambers 4 individually or in groups or jointly.

Alternatively or additionally it is possible to provide the capsule chambers 4 individually or in groups or the carrier 11 as a whole with a surrounding packaging such as a blister, welded foil or the like. This helps to ensure a long shelf life.

In the present embodiment the carrier 11 is preferably made from a relatively solid or rigid and/or diffusion proof material, particularly a suitable plastic. The piercing openings 7 are preferably already formed in the carrier 11 and are preferably covered to maintain the desired shelf life or to hermetically seal the capsule chambers 4 as well as the inlets 8 and outlets 9. For this purpose, a continuous or shared or separate cover (not shown) may again be provided, the piercing openings 7 in that case preferably being opened in succession, i.e. only the opening for the particular capsule chamber 4. Instead of the piercing openings 7 being formed during the manufacture of the carrier 11 it is theoretically also possible for the piercing openings 7 to be formed only by the piercing elements 6 or the like during the opening of the individual capsules 3. For this purpose, the piercing elements 6 may for example penetrate correspondingly weakened or thin wall portions of the carrier 11. Alternatively, it is theoretically also possible to open the capsule 3 through the inlet 8 and/or outlet 9 of the particular capsule chamber 4 before it is introduced into the capsule chamber 4. In particular, the capsules 3 may also be opened axially or along their longitudinal side.

In the embodiments shown the capsules 3 are preferably opened at two places to enable or ensure the best possible or most complete emptying of the capsule 3. Theoretically, however, it is also possible to open the capsules 3 only at one point or in one region in order to empty them. This depends in particular on the size, shape and position of the respective opening, the shape of the capsule, the shape of the chamber, the possible movement of the capsule and the like.

Moreover it is theoretically also possible for the capsules 3 not to move during emptying but for the respective dose of formulation 2 to be removed or expelled, for example, by a corresponding current of air through the opened capsule 3 or by otherwise expelling it or, for example, opening the capsule 3 completely.

The optional lattices 13 prevent any capsule fragments caused by the opening or piercing process, for example, from being carried in the current of air and delivered through the mouthpiece 10. Any such fragments of capsule can be held back by the lattices 13. Alternatively or in addition, the lattices 13 may also serve to hold the capsules 3 in the capsule chambers 4.

The lattices 13 are preferably held by, in particular, annular inserts 18 which are arranged on the capsule chambers 4 on the outlet side or inserted therein. In the embodiment shown, the inserts 18 preferably result at the same time in a desired reduction of the cross section of flow on the outlet side so as to achieve the desired flow conditions, so that the preferred longitudinal movement of the capsule 3 in the capsule chamber 4 is produced during inhalation or as air or gas flows through.

Alternatively, it is also possible to provide a continuous lattice for a plurality of capsule chambers 4 or for all the capsule chambers 4 on the outlet side.

Some alternative features and additional embodiments will be described in more detail hereinafter. Only essential differences from the first embodiment or new aspects will be described in detail. In particular, the remarks made hereinbefore continue to apply in a corresponding or supplementary manner.

Figure 3A:
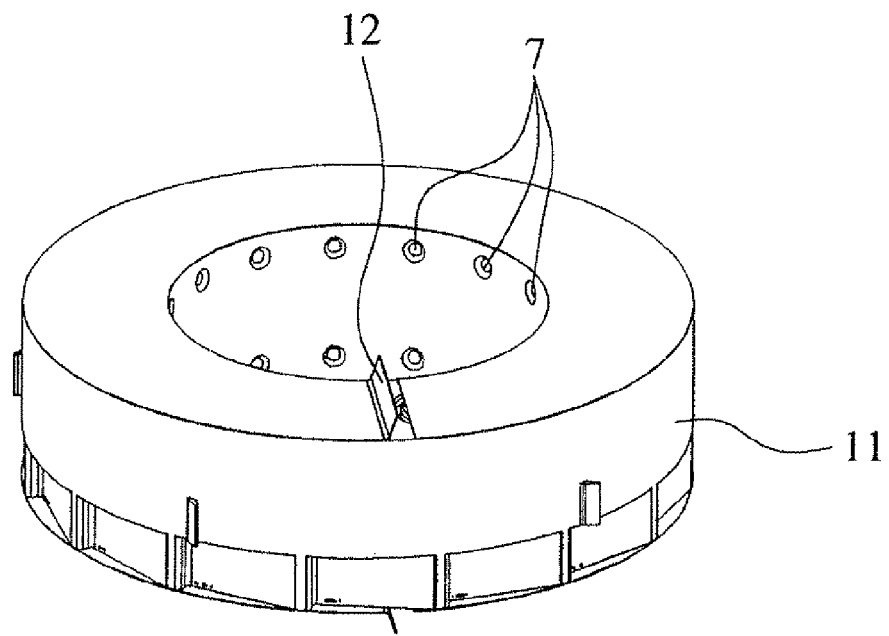
FIG. 3a shows a perspective view of a carrier of the inhaler according to FIG. 1.
Figure 3B:
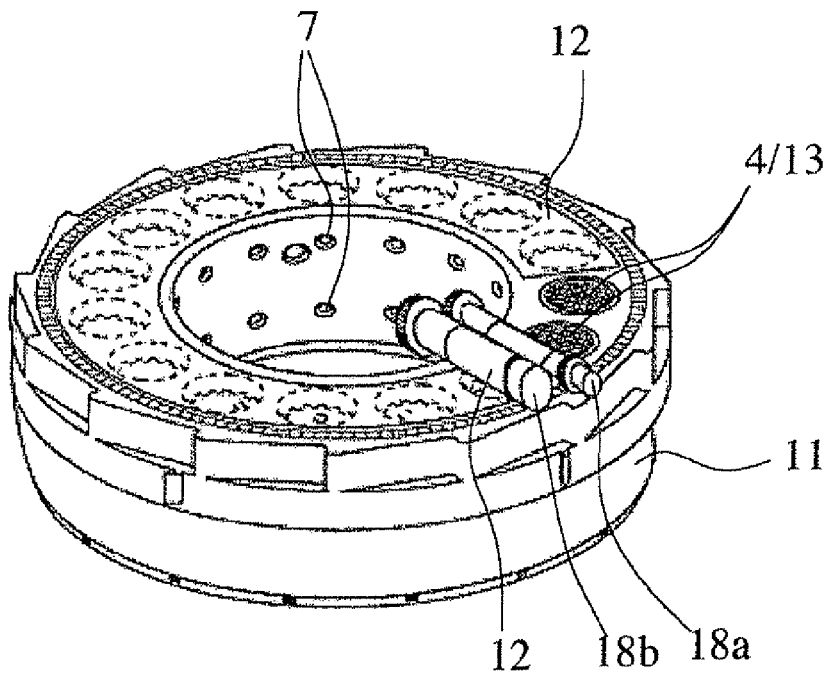

FIG. 3b shows a preferred variant for opening the cover 12. The cover 12, preferably in the form of a foil, is peeled or pulled or rolled off over a first roller 18a and preferably wound onto a second roller 18b. The two rollers 18a and b are joined together in particular by a friction clutch or gearing and/or can be driven or rotated by means of gearing, preferably during or as a result of the further movement of the carrier 11 or capsule chambers 4. The rollers 18a and b are suitably mounted in the inhaler 1.

Figure 3C:
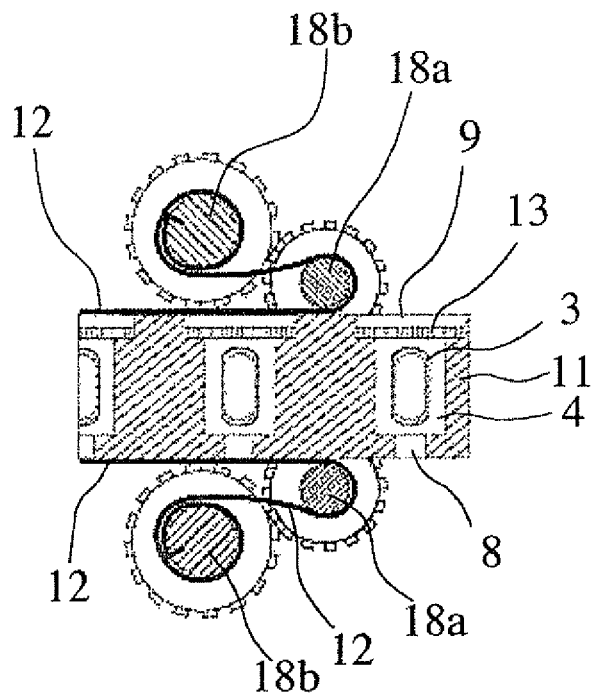
FIG. 3c is a schematic section of a detail from FIG. 3b.

FIG. 3c shows, in a section through a detail from FIG. 3b, the opening of the capsule chambers 4 or carrier 11 on both sides, which is preferably carried out in corresponding manner with at least one roller 18a, preferably two rollers 18a and b.

Alternatively, instead of the first roller 18a it is also possible for the cover to be pulled or peeled off over a fixed roller, edge or the like.

Figure 3D:
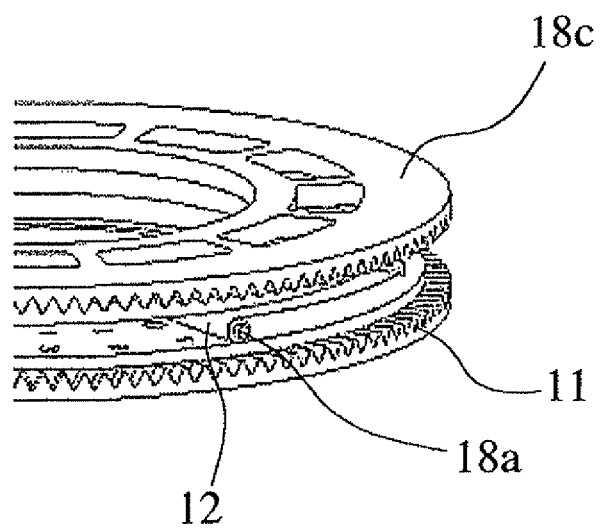
FIG. 3d is a schematic view of another embodiment.

FIG. 3d is a schematic view of a detail of another embodiment. The cover 12 is not wound on to the second roller 18b in this case, but preferably laid on a ring 18c rotating in the opposite direction, via the first roller 18a.

Figure 3E:
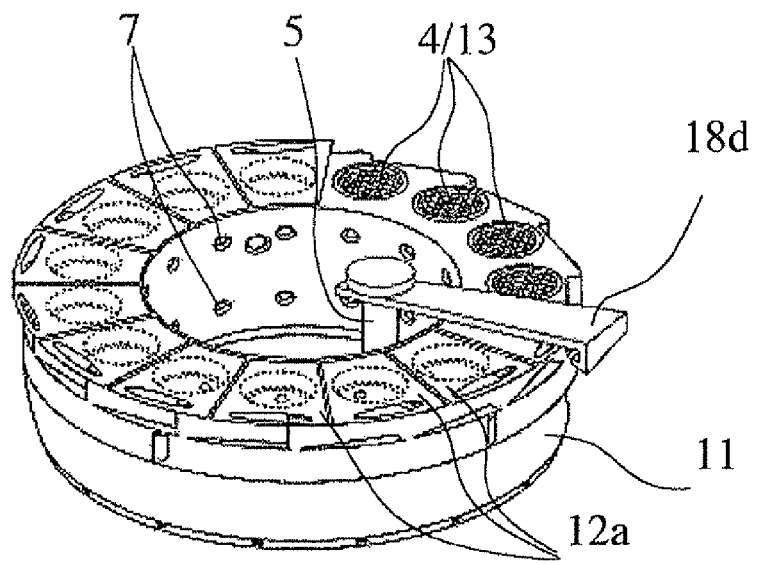
FIG. 3e is a schematic view of another embodiment.

FIG. 3e illustrates another embodiment. Here, the cover 12 is preferably formed from individual pieces or segments 12a which can be pulled away by means of an opening element 18d. The opening element 18d is preferably coupled to the opening device 5 such that when the piercing elements 6 are withdrawn the respective capsule chamber 4 is opened and thus made ready for inhalation.

Figure 3F:
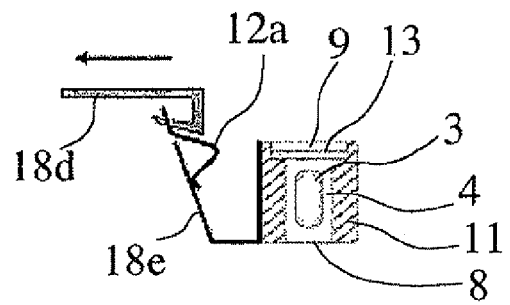
FIG. 3f is a schematic section through a detail of FIG. 3e.

The schematic section in FIG. 3f illustrates the principle. The opening element 18d is preferably constructed like a hook and preferably hooks into an optional recess and opening in the respective cover portion 12a which is to be pulled off first. In the state shown in FIG. 3e—in the course of the movement indicated by the arrow in FIG. 3f—the respective cover portion 12a is preferably pulled radially inwards and in this way the associated capsule chamber 4 is opened. This state is shown in FIG. 3f. At the latest during the movement of the opening element 18b back into its starting position shown in FIG. 3e the pulled-off cover portion 12a can become detached from the opening element 18d or its hook and preferably drop into or be placed into an optional catching container 18e or the like shown in FIG. 3f.

Figure 3G:
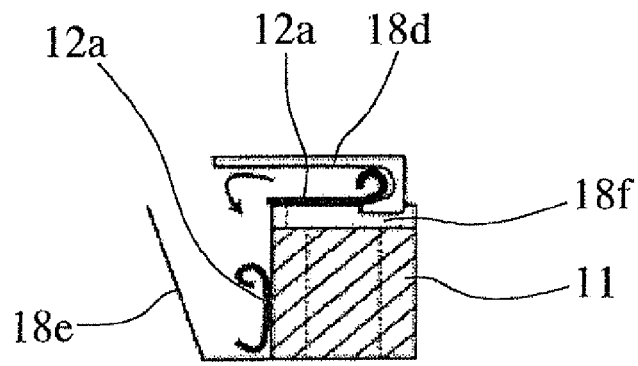
FIG. 3g is a schematic section of a detail of another embodiment.

FIG. 3g shows another embodiment in a comparable section. Here, the opening element 18d is in particular in the shape of a shovel. Preferably the opening element 18d engages with two shovel-like ends in preferably radial grooves 18f in the carrier 11 laterally underneath the respective cover portion 12a and peels it off, particularly from the outside. The cover portions 12a that are peeled off or pulled off are preferably in turn received by the collecting container 18e.

If necessary the cover 12 may also be made in one piece. In this case it is opened, preferably by a suitable construction of the opening element 18d, in such a way that the cover 12 is cut or otherwise separated into individual cover portions 12a, provided that the cover 12 is not coiled, in particular, or otherwise collected as a continuous band, strip or the like. To assist with the formation of individual or separable cover portions 12a the cover 12 is if necessary slotted, perforated and/or provided with other frangible points or the like. Preferably, separate or distinct covers 12 or cover portions 12a are provided for the inlet side on the one hand and the outlet side, on the other hand, of the capsule chambers 4. However, it is theoretically also possible to use a common cover 12 or common cover portions 12a which cover at least the respective inlet 8 and outlet 9 of a capsule chamber 4.

Figure 4A:
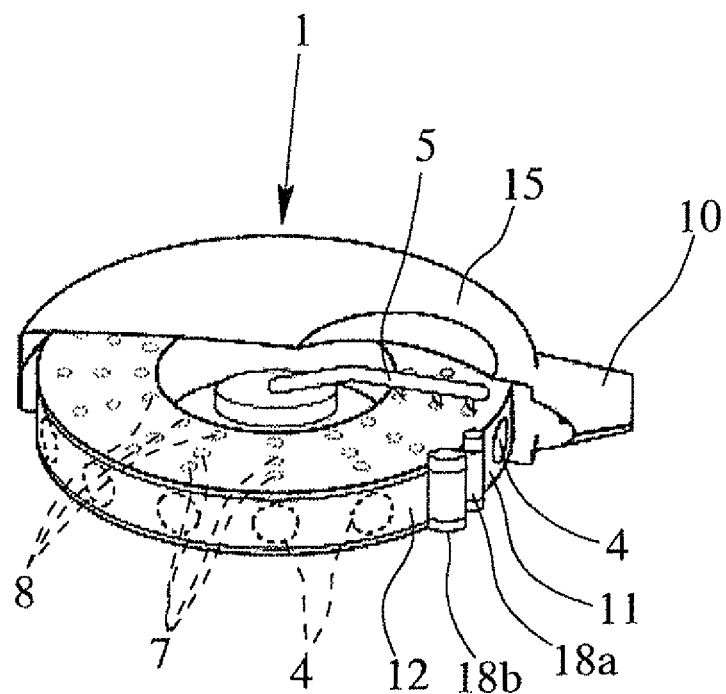
FIG. 4a is a schematic view of the inhaler according to another embodiment.
Figure 4B:
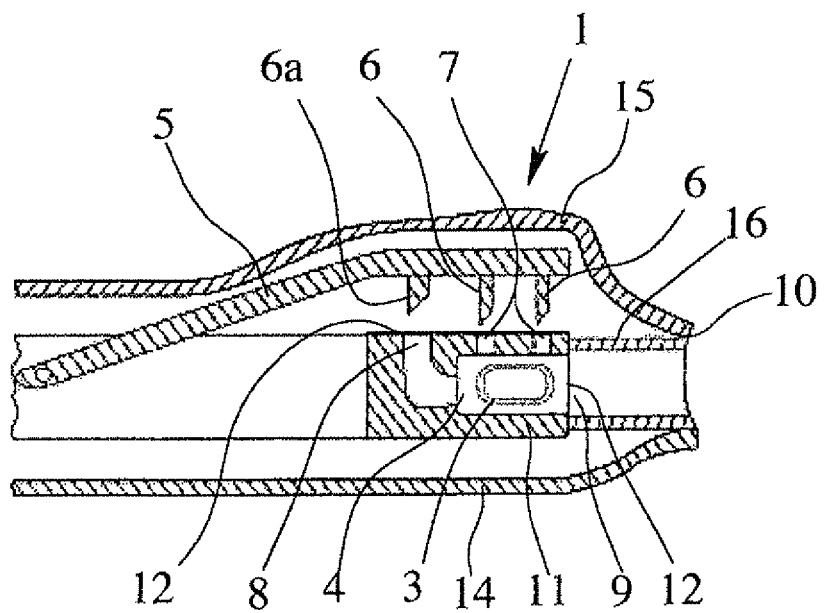

FIG. 4a shows, in a schematic view, another embodiment of the proposed atomiser 1. The capsules 3 and chambers 4 are preferably aligned radially. The cover 12 is arranged around the circumference and is preferably peeled or pulled away at the circumference accordingly, particularly by means of the rollers 18a and b or in some other suitable manner.

The opening device 5 preferably also serves to open the capsule chambers 4 on the air supply or inlet side. The common opening device 5, e.g. in the form of a lever, bar or finger, has an additional piercing element 6a for this purpose which is able to pierce the cover 12 on the axial side, for example, in order to expose or open up the inlet 8 of the respective capsule chamber 4. The piercing and/or opening movement preferably takes place in the axial direction in this embodiment. FIG. 4*b* shows a capsule chamber 4 which is still closed on the inlet and outlet side in the inhaling position adjacent to the mouthpiece 10 which here extends preferably radially.

FIGS. 5*a* to 5*c* show another embodiment. FIG. 5*a* shows in a perspective view the carrier 11 with radially aligned capsules 3 and capsule chambers 4 which are arranged or offset from one another alternately in two axial planes. Preferably, each capsule chamber 4 is associated with an opening device 5, which is in particular in the form of a lever or bar, and which is constructed in particular similarly to the opening device 5 shown in FIGS. 4a and b. To allow the overall height to be kept low in the axial direction the carrier 4 preferably has radial grooves 18f between the capsule chambers 4, on both of the flat or end faces, into which the opening devices 5 extend, as shown in the magnified detail in FIG. 5b.

The piercing or opening of the respective capsule chamber 4 preferably takes place in the axial direction. The individual opening devices 5 are preferably actuated by means of a cam, slide 18g or the like. It is particularly preferable for this to be arranged on the mouthpiece 10 or formed thereby, as can be seen from the schematic section in FIG. 5c.

The mouthpiece 10 can be radially extended and in particular rotated through 180°. With the rotary movement, the preferably annular carrier 11 is rotated further by one position, i.e. to the next capsule chamber 4. In addition the flow channel or outlet 9 formed by the mouthpiece is moved by the rotation into the corresponding axial plane of the capsule chamber 4 intended for the next inhalation. The radial movement of the mouthpiece 10 preferably brings about the, in particular, automatic actuation or movement of the opening device 5, for example by the engagement of a projection 18h into the slide 18g which preferably extends radially. The piercing or opening may if necessary take place while the mouthpiece 10 is being pulled out or pushed in.

FIGS. 6a to 6c illustrate another embodiment of the proposed inhaler 1. The capsule chambers 4 are preferably housed in two annular carriers 11 rotating in opposite directions which are aligned radially, in particular, as shown especially in FIG. 6a. The peeling of or removal of the covers 12 then preferably takes place accordingly in opposite directions, more particularly peripherally or tangentially as in the embodiments described previously.

When the mouthpiece 10 is rotated through 180°, the carriers 11 move or rotate alternately. At the same time the two covers 12 are peeled or pulled off at the circumference, preferably coiled, as explained previously. By means of a cam, slide 18g or the like, particularly on the mouthpiece 10, the preferably central or shared opening device 5 which is arranged in particular between the two carriers 11 is actuated so as to open or pierce the capsules 3 and the inlets 8 of the capsule chambers 4 alternately in the upper and lower carrier 11.

Figure 7A:
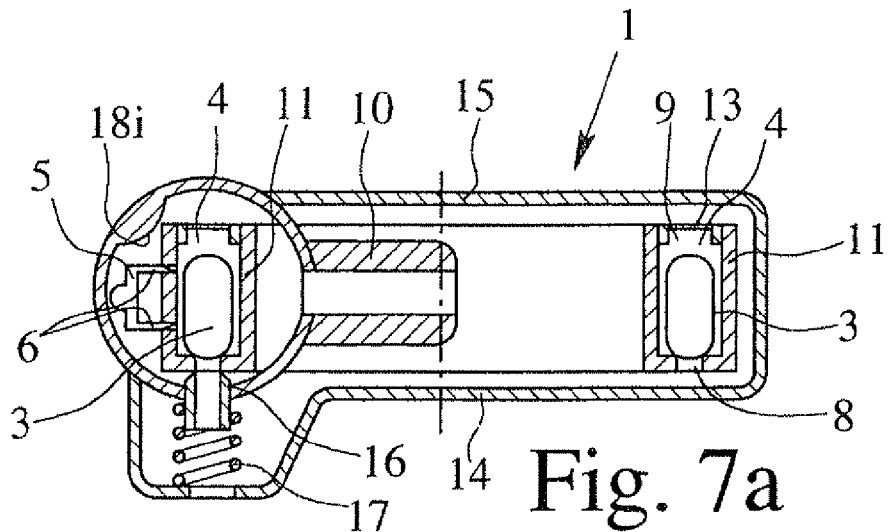
FIG. 7a is a schematic section through the inhaler according to another embodiment in a position of non-use.
Figure 7B:
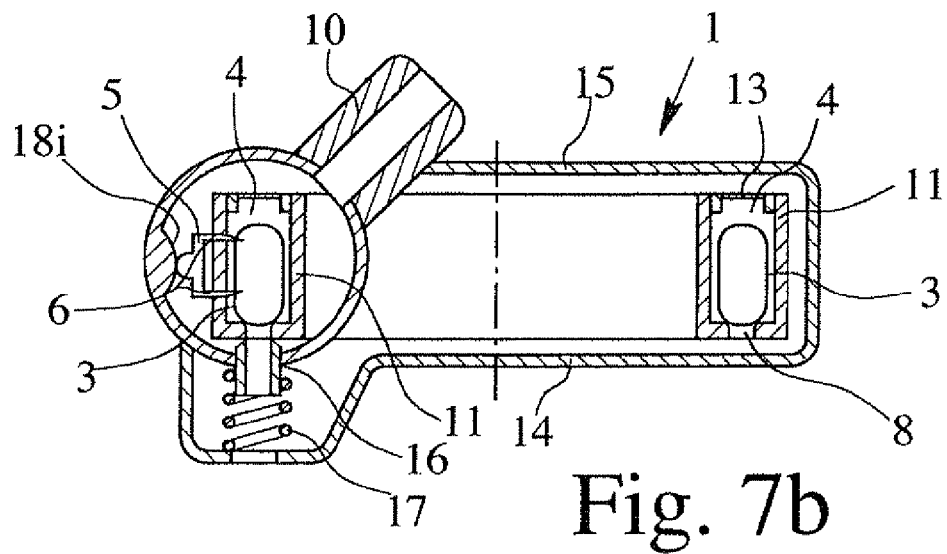
FIG. 7b is a schematic section through the inhaler according to FIG. 7a in an intermediate position.
Figure 7C:
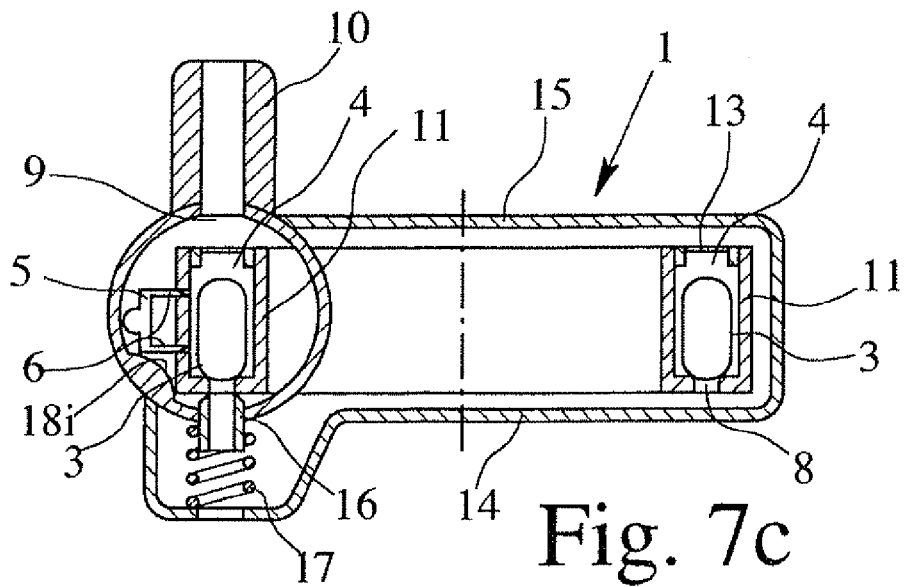
FIG. 7c is a schematic section through the inhaler according to FIG. 7a in a position of use.

FIGS. 7a to 7c show another embodiment of the proposed inhaler 1 in schematic section. The mouthpiece 10 can be rotated or folded back at right angles, particularly perpendicularly, to the plane of the ring. In this case the mouthpiece 10 or its connecting portion surrounds the carrier 11 in the region of the inhaling position preferably at least substantially completely with a preferably annular outer contour. FIG. 7a shows the mouthpiece 10 in the storage position, in which it is folded over into the centre, FIG. 7b shows an intermediate position and FIG. 7c shows the mouthpiece 10 in the folded out, particularly axial position of use.

Preferably the inhaler 1 has a mechanism such as the cam 18i or the like such that the folding out or up of the mouthpiece 10 results in the desired actuation of the inhaler 1, particularly the advancing of the carrier 11, the opening of the capsule 3 and/or the opening of the capsule chamber 4. If necessary the advancing of the carrier 11 may take place in addition or alternatively during the folding inwards of the mouthpiece 10 or as a result of this folding inwards.

The mouthpiece 10 may if required be capable of pivoting or folding through 90° or even up to 270°. Preferably the mouthpiece 10 latches both in its position of use and in its storage position.

Figure 8A:
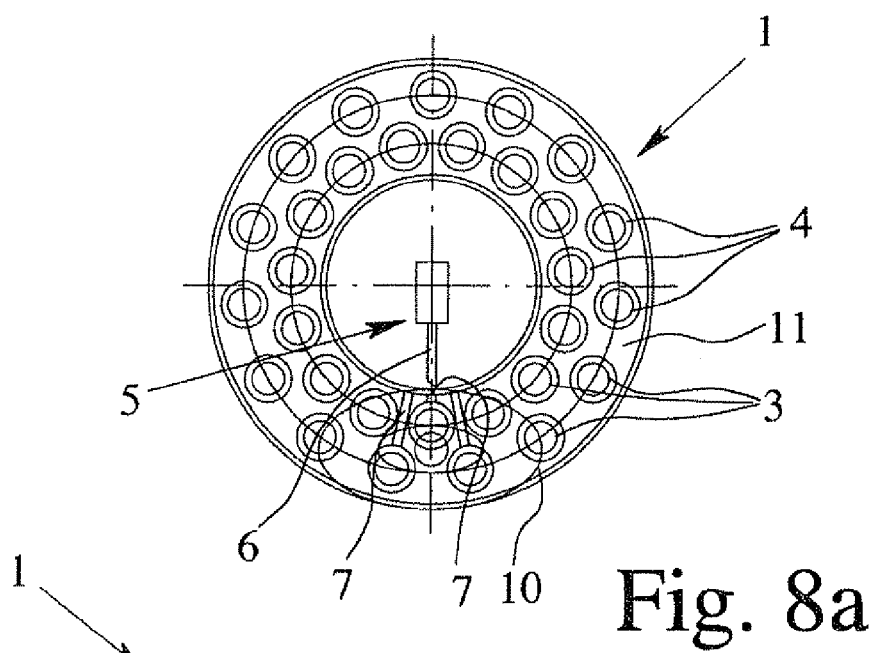
FIG. 8a is a schematic sectional view of the inhaler according to another embodiment.
Figure 8B:
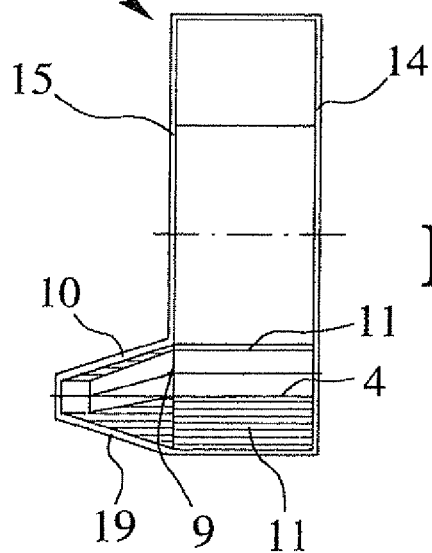
Figure 8C:
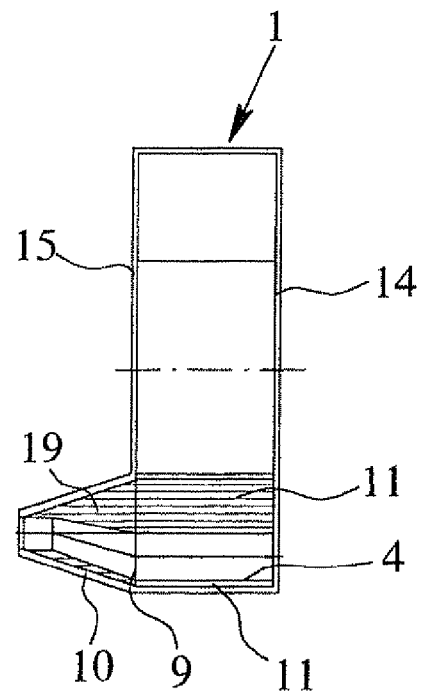

FIGS. 8a to 8c are highly schematic views of another embodiment. Here, the capsules 3 and capsule chambers 4 are arranged in several rows, particularly in two concentric rings with two different radii aligned axially and thus form a double ring arrangement. The inner and outer capsule chambers 4 are preferably offset such that the opening device 5 preferably arranged inside the ring can pierce the outer capsule chambers 4 radially with the piercing elements 6 between the inner capsule chambers 4. The piercing channels or openings are preferably arranged accordingly, as shown in FIG. 8a. The double ring arrangement results in a particularly compact construction of the inhaler 1 with a high number of capsule chambers 4 and capsules 3.

The mouthpiece 10 is preferably constructed so that the user can inhale alternately or selectively from a capsule chamber 4 and capsule 3 located on the inner circle or on the outer circle. For this purpose the mouthpiece 10 comprises, in particular, a rotatable insert 19 as illustrated in the sectional views in FIGS. 8b and 8c. Instead of the rotatable insert 19 it is also optionally possible for the mouthpiece 10 as a whole to be rotatable and in particular for rotation of the mouthpiece 10 to cause the carrier 11 to advance. Alternatively, two intake channels with different configurations may also be formed in the mouthpiece 10, inhalation being carried out through only one channel, from either an outer or an inner capsule chamber 4.

In the double ring arrangement too, a continuous or shared cover may be provided if desired for all the capsule chambers 4 or for all the inlets 8 on the one hand and for all the outlets 9 on the other hand, on the two flat or end faces of the carrier 11. However it is also possible, for example, for the covers to serve only one group of capsule chambers 4 or inlets 8 or outlets 9, and in particular for two concentric, preferably strip-like or annular covers to be provided on each flat side, so as to cover the inner capsule chambers 4 on the one hand and the outer capsule chambers 4 on the other hand.

Figure 9:
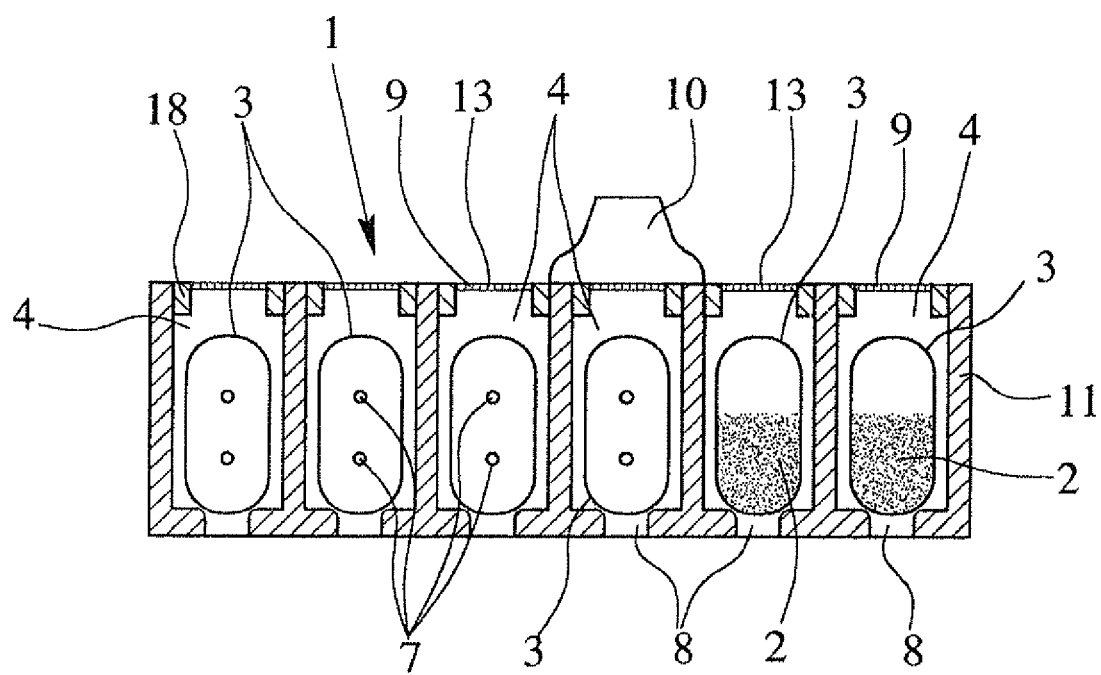
FIG. 9 is a schematic section through the inhaler according to another embodiment.

FIG. 9 is a schematic section showing another embodiment of the proposed inhaler 1. The capsule chambers 4 are preferably arranged or formed in the carrier 11 in a straight line side by side or one behind the other, but if necessary are also arranged with different alignments and/or in several directions.

The mouthpiece 10 is moveable along the carrier 11 and can be positioned over the individual capsule chambers 4 or their outlets 9 in order to allow the formulation 2 to be inhaled from the respective capsule chambers 4 or capsules 3. FIG. 9 does not show any other parts or components, such as the opening device 5, means for opening the preferably closed capsule chambers 4 or the like, on the grounds of simplicity.

The inlets 8 and outlets 9 of the respective capsule chamber 4 may if necessary also terminate at a common end of the carrier 11 facing the mouthpiece 10, for example, or at least relatively close to it, if the channel is designed accordingly. This makes it easier to use a common cover for the inlet 8 and outlet 9 and/or makes it possible to simplify the opening of the inlet 8 and outlet 9 of the respective capsule chamber 4 as a common device may be used for opening them, for example. In addition, this helps to keep the inhaler 1 compact in its construction.

Figure 10A:
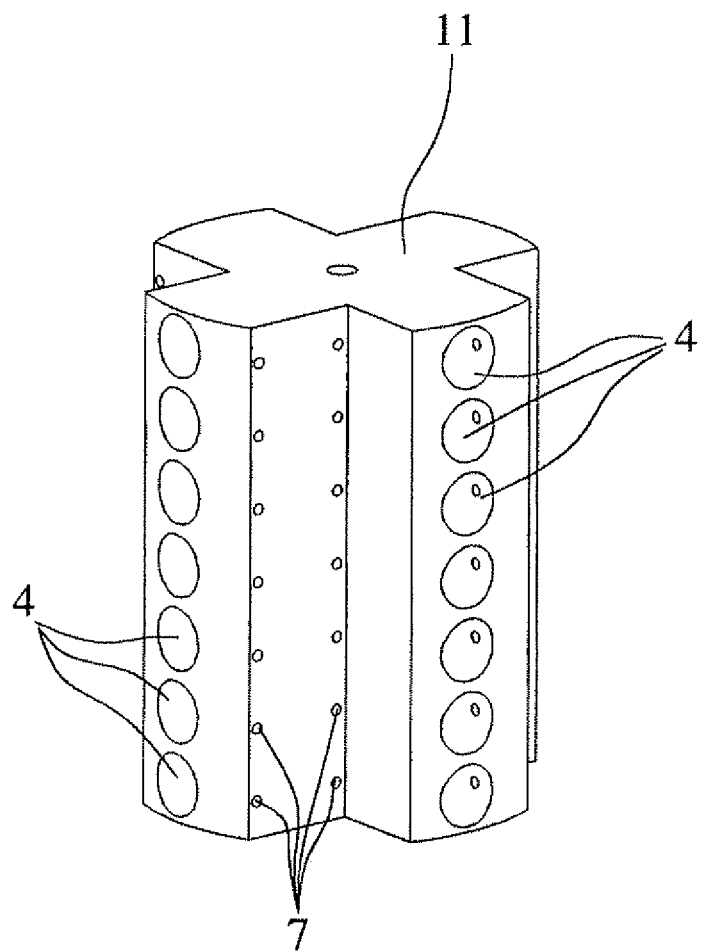
FIG. 10a is a schematic view of a carrier of the inhaler according to another embodiment.

FIG. 10a shows, in a highly schematic representation, another alternative embodiment of the carrier 11 with the capsule chambers 4 opened, in the unfilled state, i.e. without any capsules 3, covers 12 or the like. In this embodiment the capsule chambers 4 and capsules 3 are arranged preferably in a number of rows or groups and are aligned differently, in particular in terms of the directions of flow or the longitudinal directions of the various capsule chambers 4 and capsules 3.

In the variant shown in FIG. 10a the mouthpiece 10 (not shown) or other delivery device is preferably both moveable in the axial direction of the carrier 11 and also pivotable relative to the carrier 11. In particular, the carrier 11 is rotatably mounted or installed in the inhaler 1 (not shown) for this purpose.

Figure 10B:
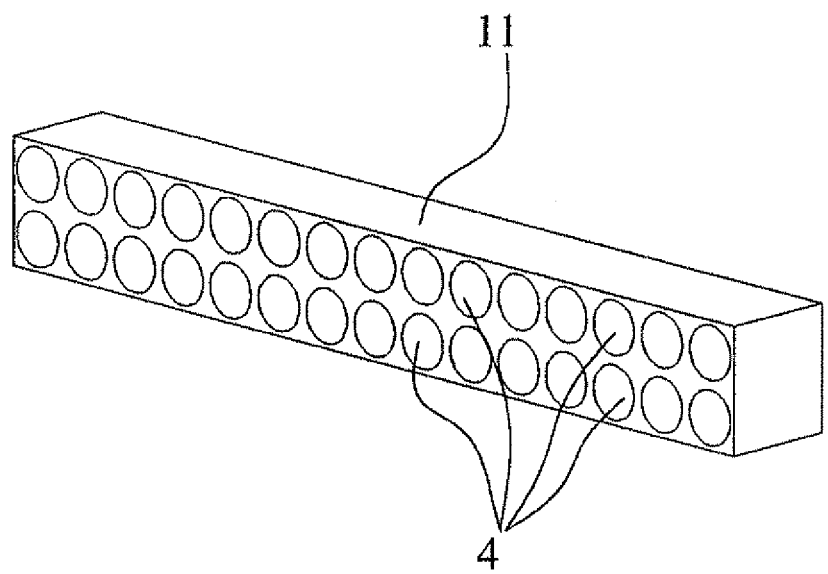
FIG. 10b is a schematic view of a carrier of the inhaler according to another embodiment.

FIG. 10b shows an embodiment in which the carrier 11 is formed with a number of rows, and in particular has at least two preferably parallel rows.

In the embodiments shown the carrier 11 is in the shape of a prism or bar, or is elongate or cruciform. However, any other shape is theoretically possible.

For example, the carrier 11 may also be of cylindrical design. The capsule chambers 4 may for example be distributed over the outer surface of any desired shape of carrier 11, e.g. over the outer surface of a cylinder, and/or may be arranged in layers, helically or in some other arrangement.

In the embodiments described above, a number of capsule chambers 4 of the inhaler 1 are formed in a common, preferably rigid or solid carrier 11 or a plurality of carriers 11. The capsule chambers 4 may, however, also be designed to be moveable relative to one another and in particular may also be separate from on another.

Figure 11:
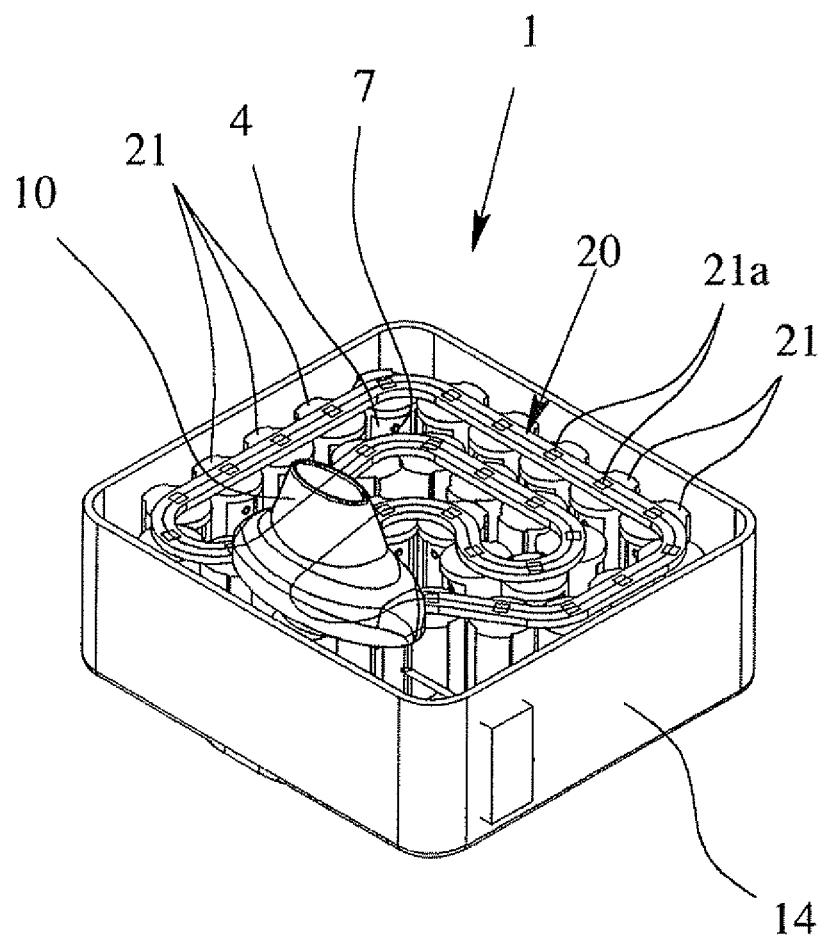
FIG. 11 is a schematic view of the inhaler according to another embodiment.

FIG. 11 shows, in a purely schematic view, a proposed inhaler 1 according to another embodiment in a partially opened or partially cut away state. Only essential differences or particular features will be described below, while the remarks and explanations already given continue to apply in a corresponding or supplementary fashion.

In the present embodiment the capsule chambers 4 are preferably intended to be used only once, and in particular are pre-packaged or filled with a capsule 3 at the factory. However, the capsule chambers 4 are not fixedly or rigidly joined together and in particular are not formed in a common carrier 11, but are preferably designed to be loose or separate or moveable units which can be separated from one another if desired. In particular, the capsule chambers 4 form a strip, chain or other arrangement.

In this embodiment the capsule chambers 4 are preferably guided so as to be moveable or displaceable within the inhaler 1 along a guide 20, particularly a rail, channel or the like.

Figure 12:
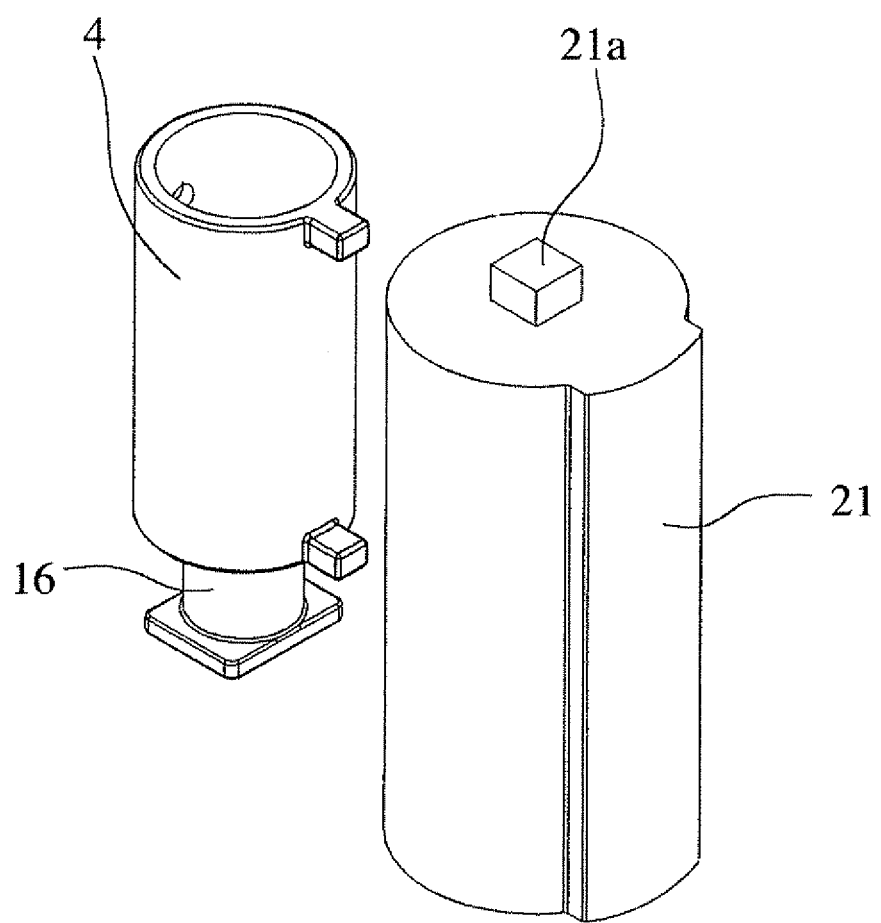
FIG. 12 is a schematic view of a guide element and a capsule chamber of the inhaler according to FIG. 11 detached therefrom.

The capsule chambers 4 may in principle be received directly by the guide 20. In the embodiment shown, the individual capsule chambers 4 are, however, preferably received in guide elements 21 which are in particular gondola-shaped and are preferably releasably held therein for inhalation, as shown in FIG. 12. The guide elements 21 are preferably guided in a specific rotational position by the guide 20 (for example by interlocking engagement of engaging elements 21a) and are if necessary releasably or non-releasably connected to one another, for example by jointing or latching.

Figure 13:
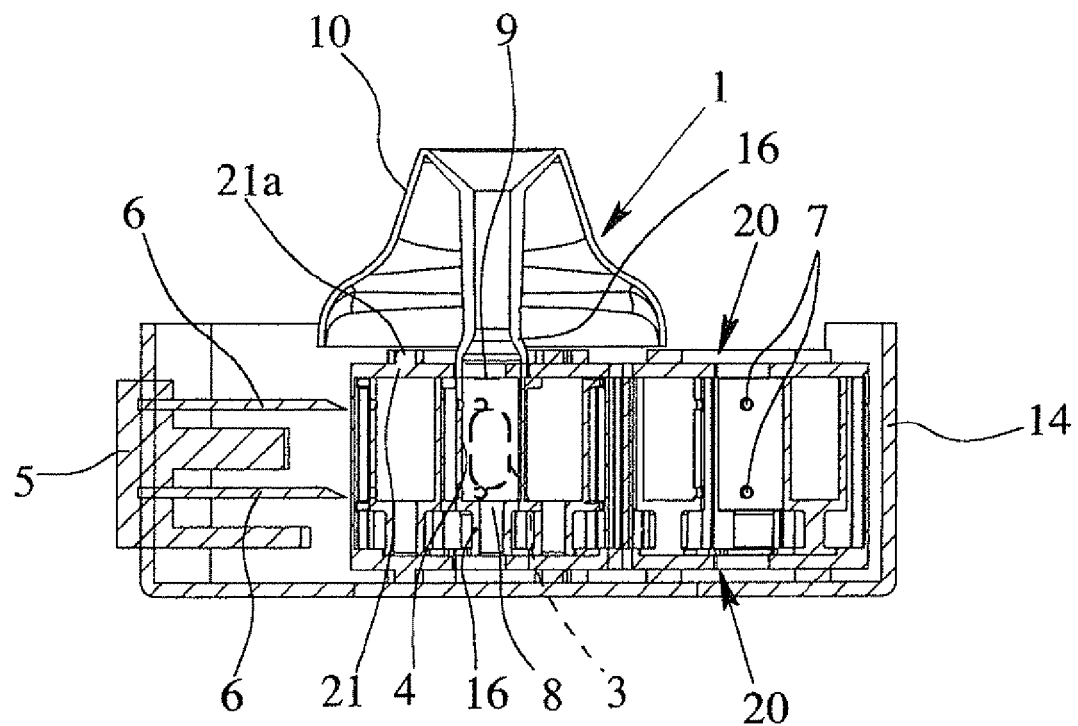
FIG. 13 shows a detailed schematic section through the inhaler according to FIG. 11.

FIG. 13 shows, in a detailed schematic section, one possible construction of the inhaler 1. The capsule chambers 4 or guide elements 21 are preferably guided at the top and/or bottom by the guide 20, particularly via the engagement elements 21a.

In the embodiment shown the capsule chambers 4 can be removed from the guide elements 21 for inhalation. FIG. 13 shows a capsule chamber 4 in the inhaling position immediately below the mouthpiece 10 with the outlet 9 or mouthpiece 10 adjacent to the capsule chamber 4. This capsule chamber 4 has been removed, particularly by the opening device 5 or some other mechanism, from the associated guide element 21, which is shown on the left hand side in the embodiment in FIG. 13, so as to open the capsule chamber 4 on the inlet side and outlet side, open the capsule 3 contained in the capsule chamber 4, particularly by piercing, and/or connect the capsule chamber 4 to the corresponding air or gas guide on the inlet side and/or outlet side.

FIG. 13 shows the capsule chamber 4 in the inhaling position, ready for inhalation. The inlet 8 and outlet 9 are open. The capsule 3 has been opened, i.e. in particular it has already been pierced. During inhalation, an air current is produced which passes through the capsule chamber 4 and causes the desired expulsion of the formulation 2 from the capsule 3, i.e. causes the formulation 2 to be dispersed in the airflow and hence in particular delivers the formulation 2 as a spray mist or particle mist.

The advancing of the capsule chambers 4 or guide elements 21 along the guide 20 is preferably carried out by actuating, particularly rotating the mouthpiece 10, preferably about the direction of inhalation or inhalation axis, i.e. about an axis which extends from the bottom to the top in the plain of FIG. 13. However, the advancing of the capsule chambers 4 or guide elements 21 may alternatively or additionally also be carried out for example by pivoting or flipping over the mouthpiece 10 and/or an associated cover (not shown) of the mouthpiece 10 about some other axis. The corresponding mechanism is not shown but would be a simple matter for the skilled man to produce. Alternatively or in addition, a separate actuating element may also be provided, particularly for advancing the capsule chambers 4 or guide elements 21.

In particular, the following sequence or following operation is possible. The mouthpiece 10 is rotated through 90°, for example, with the covering cap closed (not shown). As a result the capsule chambers 4 or guide elements 21 are moved on by one position. As the mouthpiece 10 rotates further, the next capsule chamber 4 is moved to a position under the mouthpiece 10, particularly out of the associated guide element 21, and the capsule 3 contained therein is opened or pierced. Preferably, the covering cap (not shown) cannot be flipped upwards to expose the mouthpiece 10 until this moment and only after the mouthpiece 10 has reached this rotational position, e.g. a rotation of 180° relative to the initial position.

As the covering cap of the mouthpiece 10 is flipped upwards the opening device 5 moves back into the inhaling position and in particular the piercing elements 6 are withdrawn from the capsule 3 at this stage. Inhalation can now take place.

After inhalation the covering cap is closed again. As a result the opening device is optionally withdrawn completely from the capsule chamber 4 at this stage and the capsule chamber 4 with the empty capsule 3 is exposed again. Moreover, as a result of this, the capsule chamber 4 can be received again by the associated guide element 21. However, if desired, this may only take place during the subsequent advancing of the capsule chambers 4, guide elements 21 or chain.

The movement of the capsule chamber 4 intended for the next inhalation from the respective guide element 21 into the inhaling position may be carried out for example by the opening device 5, in particular at the same time as the piercing elements 6 are introduced into the capsule chamber 4 or immediately afterwards.

Depending on the construction of the capsule chambers 4 and guide elements 21 or the connections, closures, covers or the like of the capsule chambers 4, it is not essential for the removal or release of the capsule chambers 4 from the respective guide element 21 to take place in order for inhalation to occur. Rather, corresponding opening or attachment of the capsule chamber 4 or guide element 21 in the inhaling position may be carried out without removing the respective capsule chamber 4 in order to allow the desired supply and removal or air during inhalation.

A suitable construction of the guide 20, other guide means, the capsule chambers 4 and/or the guide elements 21 ensures the desired alignment and positioning of the capsule chambers 4 or makes it possible, in particular in order to permit the piercing elements 6 to be inserted through the piercing openings 7 into the capsule chamber 4 intended for the next inhalation.

If necessary, the capsule chambers 4 or guide elements 21 may be configured or arranged in a helical, meandering, concentric or multi-row design or in any other suitable manner and may also be moveable in opposite directions.

In the embodiment according to FIGS. 11 to 13 the capsule chambers 4 or guide elements 21 are preferably joined together releasably or non-releasably by jointing, latching or by any other suitable method. Alternatively, the capsule chambers 4 or guide elements 21 or capsules 3 may also not be connected to one another but be guided loosely by the guide 20, for example, or received in the inhaler one in some other suitable manner.

The drive for moving the capsule chambers 4 or guide elements 21 or the chain formed thereby or a strip or the like thus formed may be provided, as desired, from inside, outside, below or above, for example by means of a rotary cross, a pinion or the like. The drive may, if desired, act directly on the capsule chambers 4 or guide elements 21. Alternatively, the capsule chambers 4 or guide elements 21 may also be arranged on a preferably common or continuous or encircling drive means such as a chain, belt or the like, which is itself driven.

The above explanations and remarks apply accordingly to the capsules 3 as well, if they are accommodated not in capsule chambers 4 but in other packages or are loose in the inhaler 1, so that a transfer into a capsule chamber 4 is still necessary for the actual inhalation. Some embodiments of this kind are explained by way of example hereinafter.

Figure 14A:
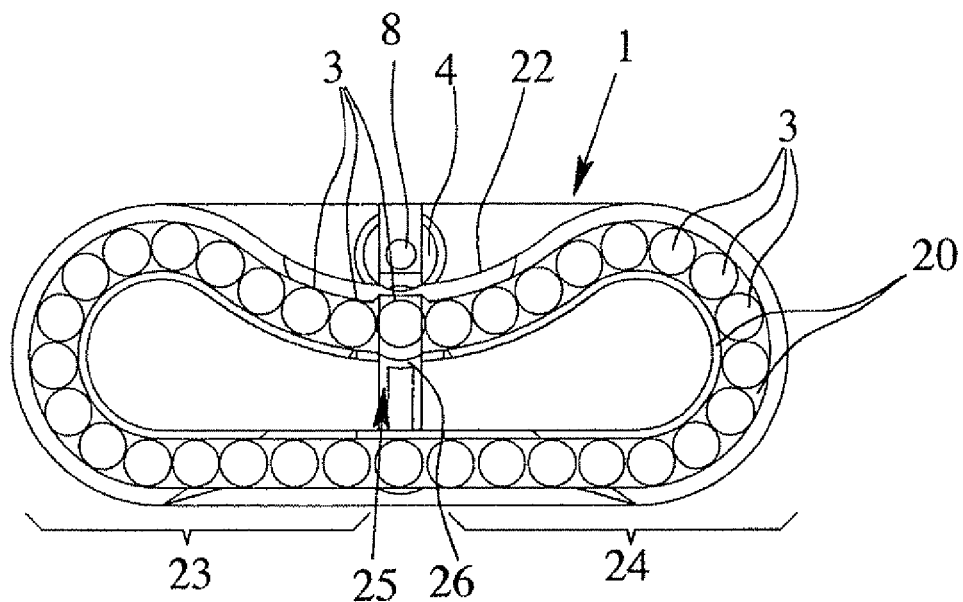
FIG. 14a is a schematic section through the inhaler according to another embodiment with the capsule chamber open.
Figure 14B:
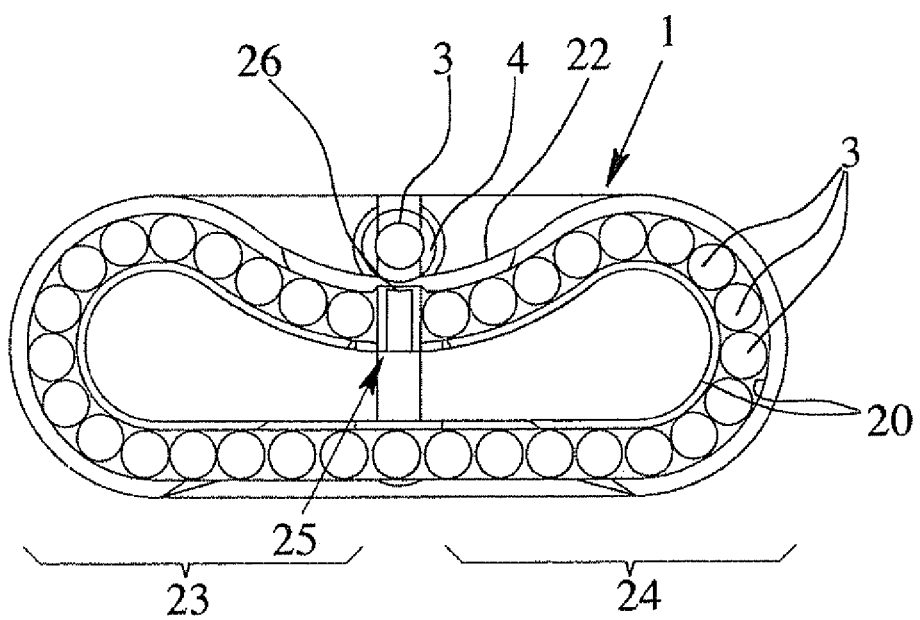
FIG. 14b is a schematic section through the inhaler according to FIG. 14a with a closed capsule chamber.

FIGS. 14a and b show one embodiment of the proposed inhaler 1 which is preferably kidney-shaped, particularly with a taper or constriction 22 in a central region (of the housing). FIGS. 14a and 14b show the inhaler 1 in schematic section in various operational states.

The inhaler 1 preferably has a first receiving chamber 23 (capsule reservoir) for unused or still full capsules 3 and a second receiving chamber 24 for used or emptied capsules 3. The capsules 3 are preferably contained in the first and/or second receiving chamber 23, 24 in a helical, linear or circumferential arrangement and/or one behind the other, or may be conveyed through this or the inhaler 1. It is also possible, in particular, for them to be held in a multi-row or meandering or any other arrangement.

The capsules 3 are preferably joined together and/or moveable by means of a flexible connecting or drive means, such as a belt, a plastic strip, a blister strip or the like. However, the capsules 3 may also be contained in some other arrangement, e.g. loose or in the manner of roller bearings and/or guided by a guide 20 as shown in the second embodiment.

The inhaler 1 preferably has only one capsule chamber 4. The capsule chamber 4 can be opened in order to fill it with capsules 3 and/or empty it, and in particular can be opened along its longitudinal side or at right angles to the direction of flow during inhalation. For automatic filling or emptying of the capsule chamber 4 with capsules 3, in particular, the inhaler 1 has a device 25 also known as a filling device.

Figure 14C:
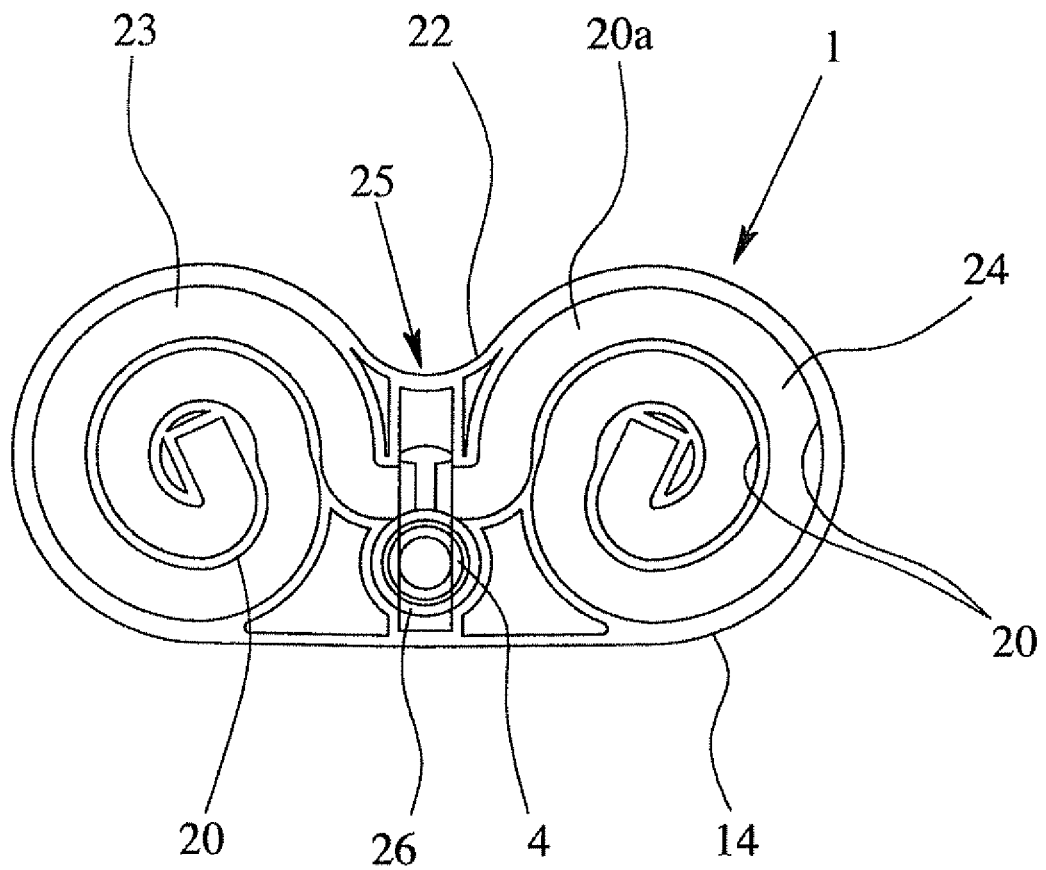
FIG. 14c is a schematic section through the inhaler according to another embodiment with a closed capsule chamber.
Figure 14D:
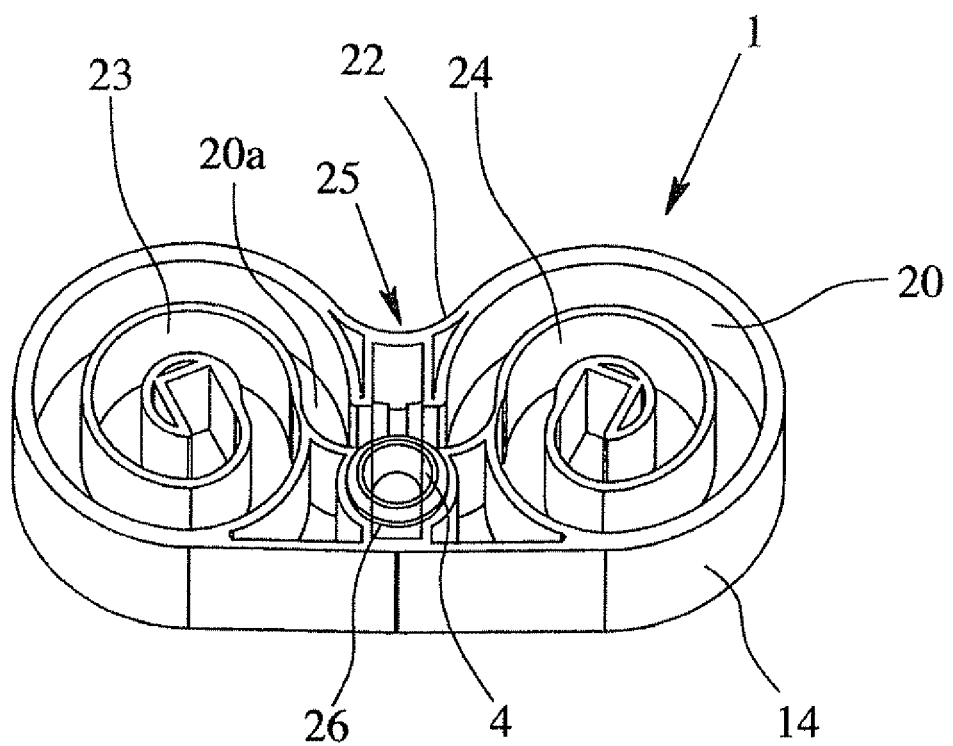
FIG. 14d is a perspective view of the open inhaler according to FIG. 14c.

FIGS. 14c and 14d show a very similar embodiment of the proposed inhaler 1, and consequently only aspects that are different from the preceding embodiment will be described hereinafter.

FIGS. 14c and 14d show the capsule chamber 4 in the closed state. Capsules 3 are not shown.

The guide 20 preferably in turn forms a track 20a for the capsules 3, which is not circumferential but helical.

FIGS. 14c and 14d illustrate the preferably kidney shaped design of the atomiser 1, particularly by means of the taper 22 which is preferably arranged in the region of the centre of the housing. This makes the inhaler 1 in particular very pleasant and ergonomic to grip or hold.

The upper housing part 15 (not shown) of the inhaler 1 preferably carries the mouthpiece 10, which is upwardly adjacent to the capsule chamber 4 and on an extension thereof, in particular.

The capsules 3 are particularly adapted to be contained in the first receiving chamber 23 and/or second receiving chamber 24 in a helical arrangement or any other suitable arrangement.

FIG. 14a of the preceding embodiment shows the capsule 4 in the open state. A capsule chamber segment or portion 26, which forms in particular a central portion of the capsule chamber 4, has been moved or pulled out of the capsule chamber 4.

Figure 15A:
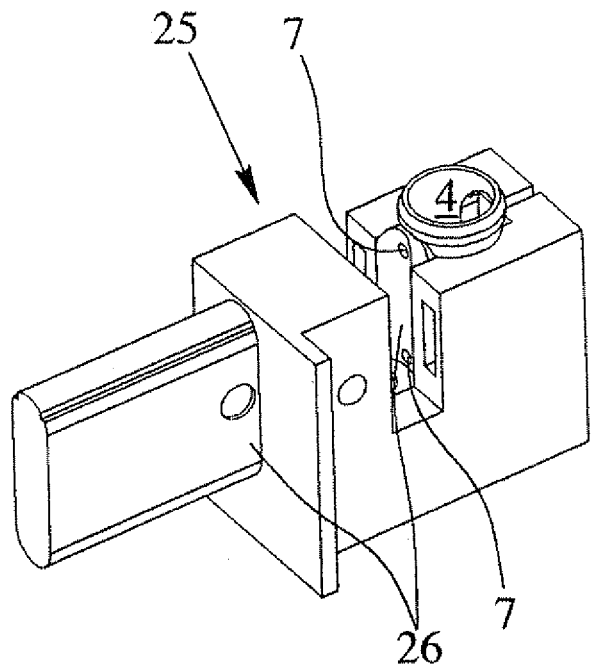
FIG. 15a is a schematic view of a filling device and the capsule chamber of the inhaler according to FIG. 14a with the capsule chamber open.

FIGS. 15a and b are schematic views illustrating one possible embodiment of the device 25. In particular, the slide-like construction of the capsule chamber portion 26 is shown. The capsule chamber part 26 is moveable radially to the central axis of the capsule chamber 4 or the main direction of flow in the capsule chamber 4 and/or at right angles to the main direction of movement of the capsules 3 or longitudinal axis of the capsules 3, in the embodiment shown.

Figure 15B:
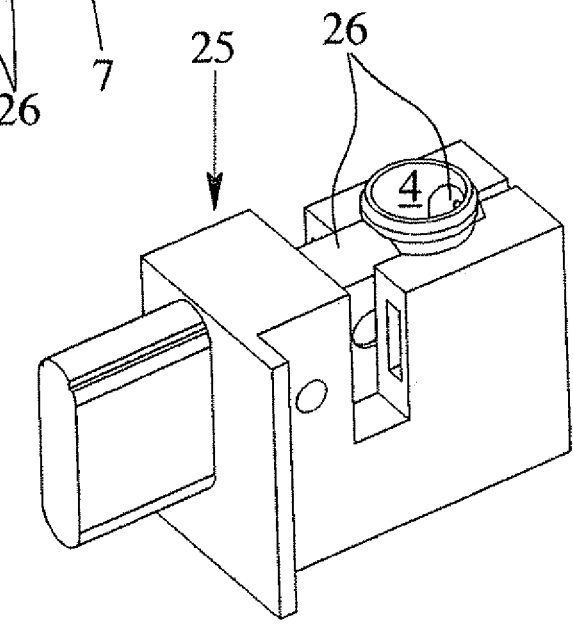
FIG. 15b is a schematic view of a filling device and the capsule chamber of the inhaler according to FIG. 14a with the capsule chamber closed.
Figure 15C:
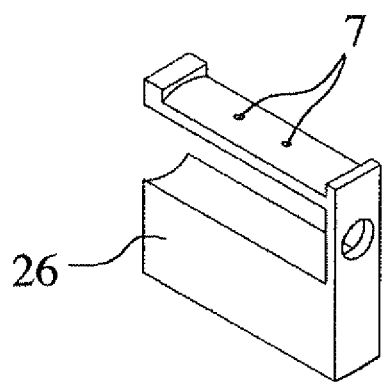

FIG. 15a shows the device 25 in the open state, i.e. with the capsule chamber portion 26 moved out. FIG. 15b shows the device 25 in the closed state, i.e. with the capsule chamber 4 closed. FIG. 15c is a perspective view showing one possible embodiment of the capsule chamber part 26.

The capsule chamber part 26 can be moved out, in particular, into the guide 20 or a guide or movement area or a preferably encircling path for the capsules 3, so that the extended capsule chamber part 26 can be loaded or filled directly with the capsule 3 intended for the next inhalation as the capsules 3 are correspondingly moved onwards from the first receiving chamber 23 into the second receiving chamber 24.

Then the device 25 conveys the capsule 3 received into the capsule chamber 4, particularly by corresponding displacement or other movement of the capsule chamber part 26. In this way the capsule chamber 4 is filled with the capsule 3 and closed, as shown in FIG. 14b.

The opening, particularly piercing, of the capsule 3 may be carried out if desired by means of the device 25, a separate opening device 5, not shown here, or other suitable means. In particular, the opening may take place directly as the capsule 3 is conveyed or transferred to or into the capsule chamber 4 or only after it has reached the capsule chamber 4, i.e. only after the capsule chamber 4 has been closed. In the latter case it is also possible to open the capsule 3 only immediately before inhalation, for example by suitable actuation of the mouthpiece 10, a covering cap (not shown) associated with the mouthpiece 10, or the like.

After the emptying of the capsule 3, i.e. after the inhalation or delivery of the formulation 2, the emptied or used capsule 3 is taken out of the capsule chamber 4 once more by means of the device 25 (emptying of the capsule chamber 4). This removal and the opening of the capsule chamber 4 are carried out here by correspondingly moving out the capsule chamber part 26 together with the emptied capsule 3. If the capsule chamber part 26 is back in the pulled out position, the capsules 3 are advanced by means of a mechanism or drive (not shown) (for example by rotating or pivoting the mouthpiece 10) or operating some other actuating element (not shown) of the inhaler 1. In this way the empty capsule 3 is advanced into the second receiving chamber 24.

In the present embodiment the capsule chamber 4 is used many times. This results in a particularly compact and space saving construction for the inhaler 1 or—for the same size of inhaler—a capacity for a larger number of capsules 3.

The automatic filling and emptying of the capsule chamber 4 with the capsules 3 means that handling is very simple and particularly hygienic. The individual capsules 3 may be opened, as desired, during transportation or during the filling of the capsule chamber 4, as already discussed. For this purpose the corresponding opening device may optionally have a fixed opening element such as a blade or the like in the path of travel so that the capsules 3 are automatically opened, e.g. cut open longitudinally, during the filling of the capsule chamber 4. However, the opening may also take place as the capsules 3 are removed from the first receiving chamber 23 or fed into some other reservoir 31. For example, each capsule 3 may if necessary be packed individually and/or held in another suitable container, in which case the opening of the packaging or container or the removal of the capsules 3 and optionally the simultaneous opening of the capsules 3 preferably take place individually.

Figure 16A:
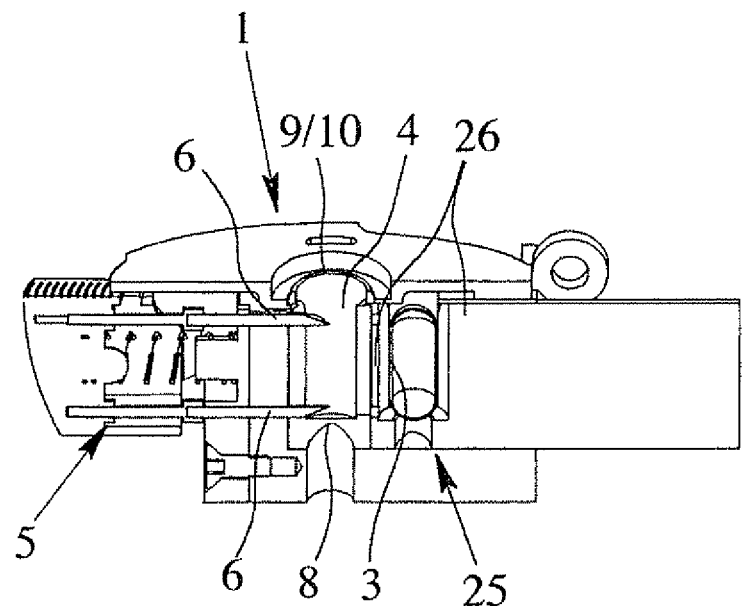
FIG. 16a is a schematic detailed section through the inhaler according to FIG. 14a with the capsule chamber open.
Figure 16B:
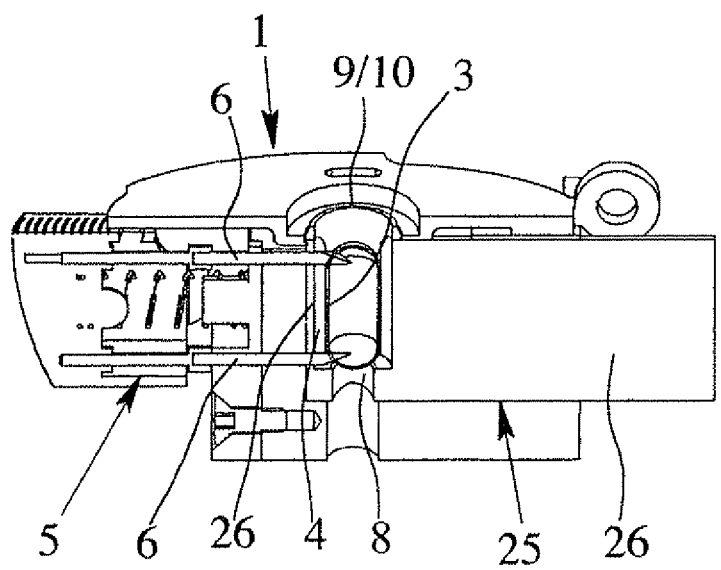
FIG. 16b is a schematic detailed section through the inhaler according to FIG. 14a with the capsule chamber closed.

FIGS. 16a and b are schematic sections through details of the inhaler 1 showing one possible design of the opening device 5 and/or the filling device 25. FIG. 16a shows the capsule chamber 4 in the open state while FIG. 16b shows it in the closed state.

In the example shown the capsule 3 is preferably opened or pierced directly as the capsule chamber 4 is closed. This is done by the piercing elements 6 already projecting into the empty or opened capsule chamber 4. As the capsules move in or the chambers are closed, the piercing elements 6 are able to penetrate the piercing openings 7 in the capsule chamber part 26 and open or pierce the capsule 3 directly. For inhalation, the piercing elements 6 are then withdrawn from the capsule 3, for example by opening the mouthpiece 10 or some other actuation.

Instead of the construction of the capsule chamber 4 shown, it is also possible, however, to use constructions which allow the capsule chamber 4 to be opened, particularly along its longitudinal side, but if necessary also in its equatorial plane, on the inlet or outlet side or by some other means.

Figure 17A:
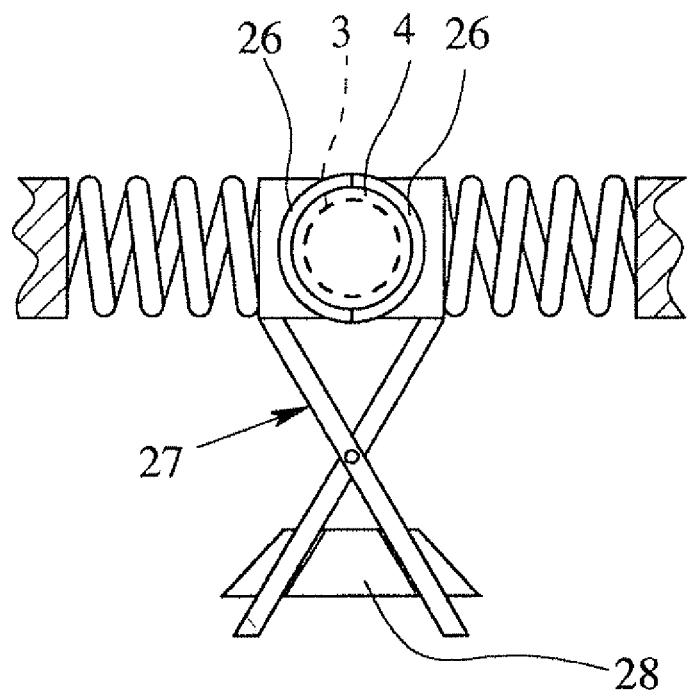
FIG. 17a is a schematic view of a closed capsule chamber of an inhaler according to another embodiment.
Figure 17B:
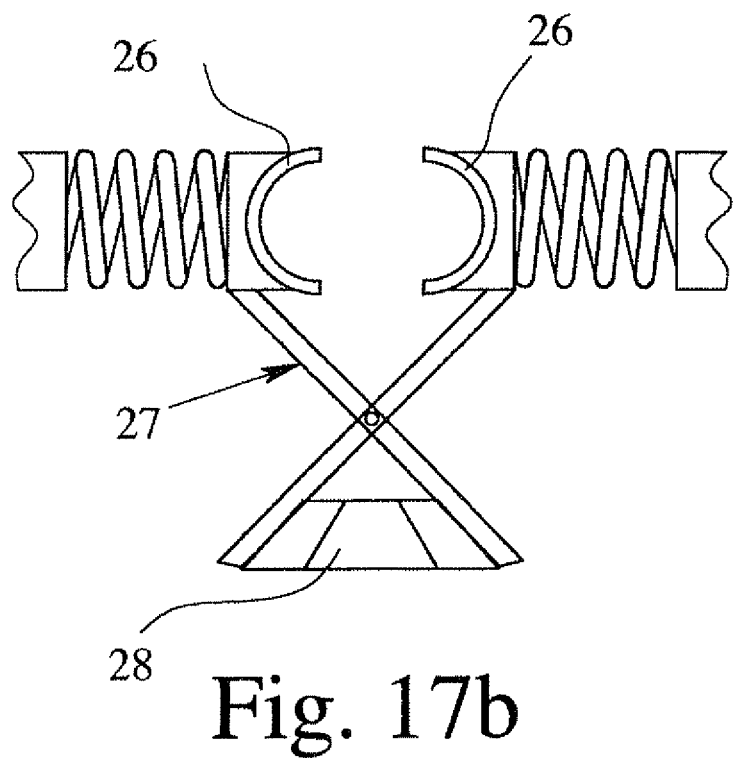
FIG. 17b is a schematic view of the capsule chamber of the inhaler according to FIG. 17b in the open state.

FIGS. 17a and b are schematic sectional views of another embodiment of the openable capsule chamber 4. The capsule chamber 4 is divided lengthways, in particular, or is made up of at least two segments or parts 26 which can be moved apart and together again by means of a tong-like mechanism 27, for example. FIG. 17a shows the capsule chamber 4 in its closed state. FIG. 17b shows the capsule chamber 4 in its open state, i.e. with parts 26 moved away from one another. Preferably, opening is effected countered to the spring force, for example by means of a control slide 28 which expands the tong mechanism 27 and is thus able to open the capsule chamber 4.

Figure 18:
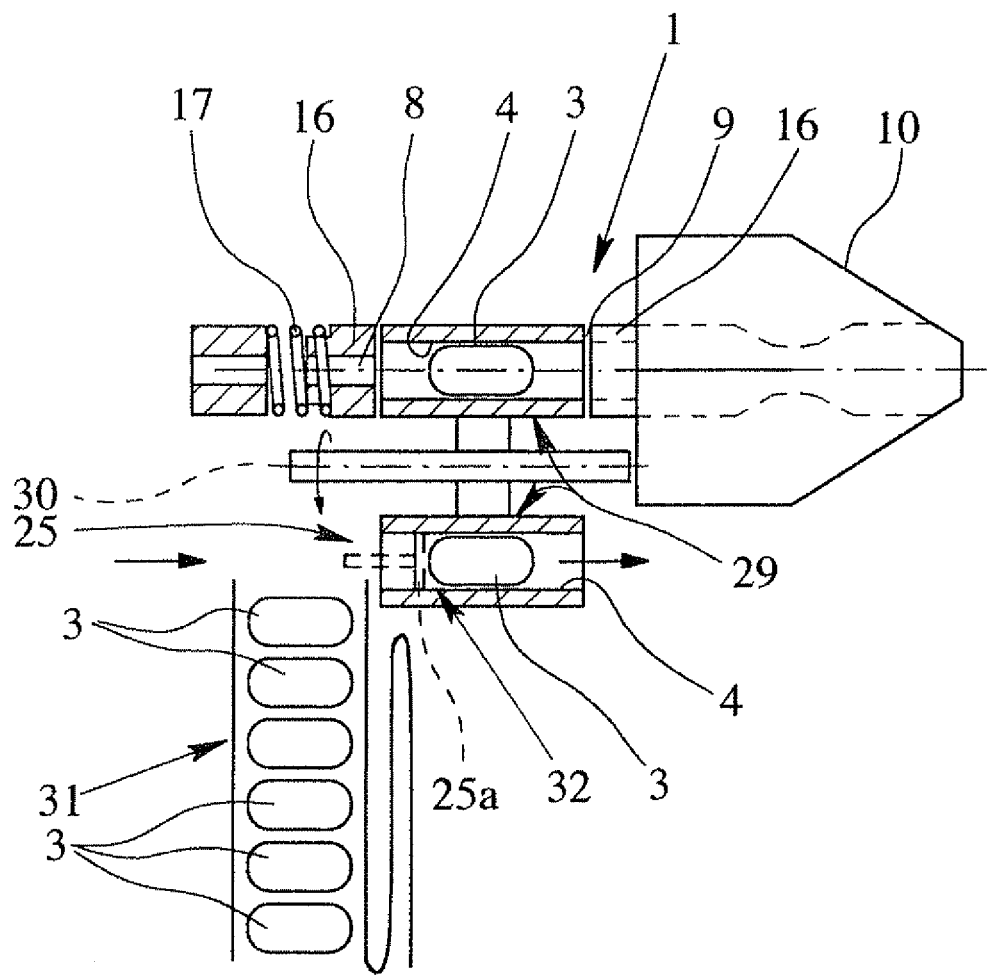
FIG. 18 is a schematic construction of the inhaler according to another embodiment.

FIG. 18 shows another embodiment of the proposed inhaler 1 in a purely schematic, partially sectional view of a detail. The inhaler 1 preferably has several, at least two, capsule chambers 4 which are arranged in particular in the manner of a revolver on a rotary or conveying means or pivoting device 29 or are formed thereby. The capsule chambers 4 are preferably pivotable about a pivot axis 30 extending parallel to the longitudinal extent or main direction of flow. In this embodiment the capsule chambers arranged on the pivoting device 29 or formed thereby are used many times.

In the case of two capsule chambers 4, one capsule chamber 4 can be pivoted alternately into the inhalation position for connecting to the inlet 8 and outlet 9, in particular. The other capsule chamber 4 then preferably assumes a filling position in which this capsule chamber 4 can be loaded with the capsule 3 intended for the next inhalation. The capsule 3, which has already been emptied beforehand, is removed, particularly expelled, from the capsule chamber 4 at this stage or previously, as shown in FIG. 18.

Preferably the capsule chamber 4 is filled with capsules 3 and emptied thereof by the device 25, which particularly comprises a conveying element 25a, as shown in FIG. 18. The direction of filling and emptying is indicated by arrows P. In particular, the capsule chamber 4 is filled and emptied in the longitudinal or axial direction and/or by means of the preferably slide-like conveying element 25a, which can optionally clean the capsule chamber 4 at the same time as it is pushing out or removing the emptied or used capsule 3. However, other constructive solutions and/or filling or emptying devices are also possible.

Preferably, the inhaler 1 has a device 32 for cleaning its re-useable capsule chamber or chambers 4. This cleaning device 32 may if necessary be formed by the device 25 for filling and emptying the capsule chamber 4 or the conveying element 25a thereof, as shown in FIG. 18, which can preferably be inserted in the form of a slide or the like into the capsule chamber 4 for filling or emptying and is provided with a brush or other cleaning element for cleaning the capsule chamber 4 accordingly, preferably on each filling or emptying.

After the emptying of the capsule chamber 4 indicated in FIG. 18 this chamber is filled with the next capsule 3. Preferably, for this purpose, the next capsule 3 is pushed or inserted by means of the conveying element 25a into the capsule chamber 4 which is in the filling position (the lower one in FIG. 18). In the embodiment shown the cleaning device is thus preferably formed by the device 25 or its conveying element 25a.

In the case of the pivoting device 29, if three capsule chambers 4 are formed, for example, there is the possibility that the capsule chambers 4 can occupy three positions alternately, namely the filling position, the inhaling position and an (additional) cleaning position. By suitable further rotation each capsule chamber 4 is moved from one position to the next. In the cleaning position, using the cleaning device already mentioned, the used capsule 3 can be removed from the respective capsule chamber 4 and the capsule chamber 4 can be cleaned.

The unused capsules 3 are preferably taken from a capsule reservoir 31, which is shown purely diagrammatically in FIG. 18. This capsule reservoir 31 may contain or receive the capsules 3 for example in loose form or in any other suitable form, for example as a stack, strip, chain or in discrete receptacles, holders or spaces. If necessary, a conveying device or the like is also integrated in the capsule reservoir 31 and/or is formed by the device 25 for filling the capsule chamber 4 (cf. FIGS. 15a and b and FIGS. 16a and b).

In the embodiment shown the capsules 3 are preferably taken from the capsule reservoir 31 individually. In particular they may be removed through a gate or the like so that the capsules 3 which are not yet used and are contained in the capsule reservoir 31 still remain hermetically sealed as far as possible, and in particular are protected from environmental influences.

The capsule reservoir 31 may in particular be in the form of a magazine. It is either integrated in the inhaler 1 or can be coupled thereto. If necessary the capsule reservoir 31 is also replaceable and/or refillable.

The capsule reservoir 31 may for example be of tubular construction, while the capsules 3 may for example be aligned or accommodated parallel to the longitudinal axis of the capsule reservoir 31, as explained hereinafter by way of example with reference to FIGS. 39 to 42.

The removal or expulsion of the capsules 3 may take place individually one after the other or possibly also in batches. This may be done for example using a rotary mechanism, a slide device, a spring mechanism or any other suitable method, as explained hereinafter with reference to FIGS. 39 to 42, by way of example.

The removal device or gate or the like can preferably be closed again in order to protect the capsules 3 still contained in the capsule reservoir 31. Additionally or alternatively, a desiccant is preferably provided in the capsule reservoir 31, in particular to protect the capsules 3 from excessive moisture.

Alternatively or in addition, the capsules 3 may also be provided with an additional outer packaging. The capsules 3 are, in particular, individually wrapped or packaged.

In addition or alternatively the capsule reservoir 31 may itself be provided with an outer packaging which is not opened, for example, until the capsule reservoir 31 is placed in the inhaler 1 or when a capsule 3 is removed for the first time.

The used or empty capsules 3 are preferably received by the inhaler 1, for example in a second receiving chamber as in the previous embodiment. However, the used or emptied capsules 3 may also be expelled, if necessary. This allows the inhaler 1 to be made more compact.

Figure 19:
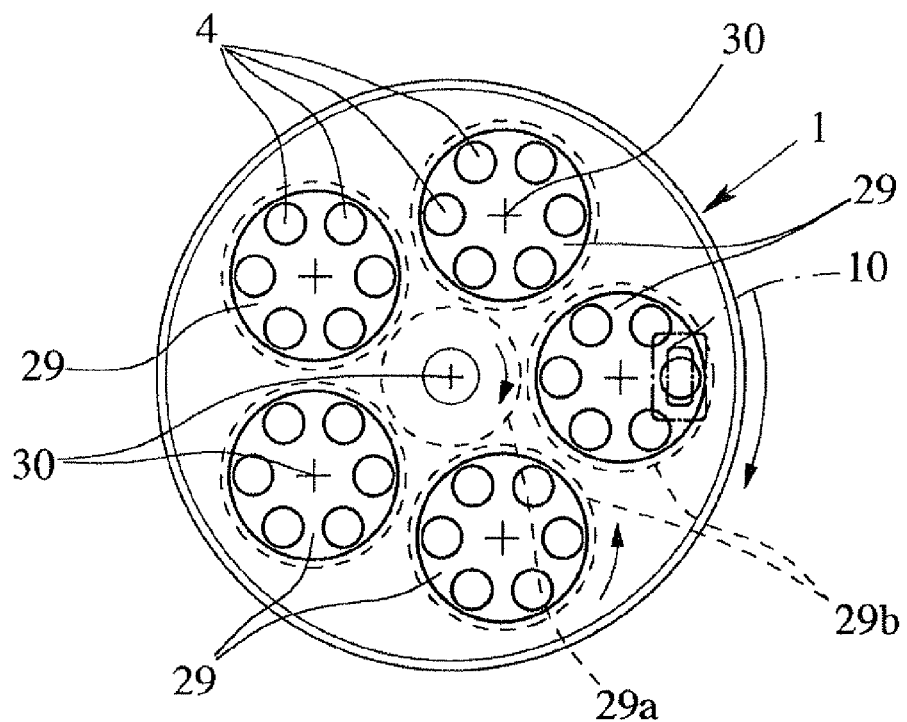
FIG. 19 shows a schematic construction of the inhaler according to another embodiment.
Figure 20:
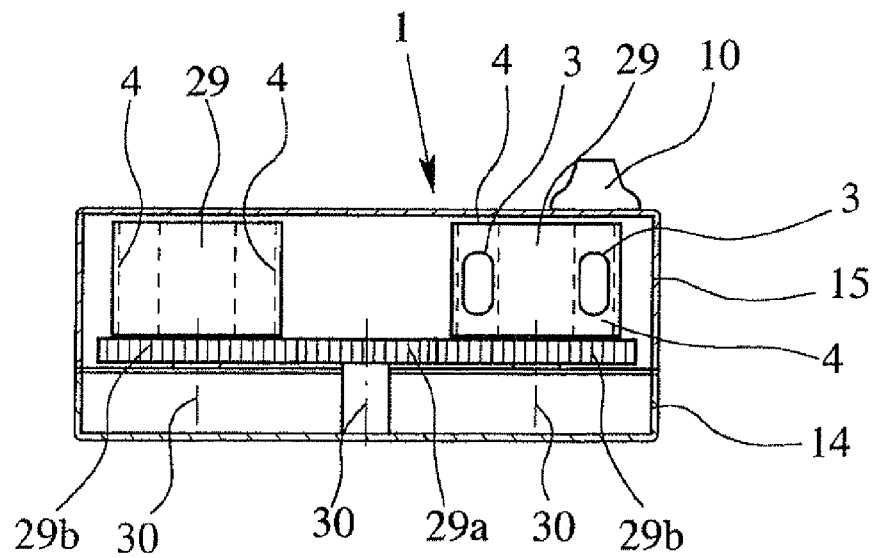
FIG. 20 is a schematic section through the inhaler according to FIG. 19.

FIG. 19 shows another embodiment of the proposed inhaler 1 in a purely schematic open plan view. FIG. 20 shows the inhaler 1 in schematic section. The inhaler 1 preferably has a plurality of rotary or conveying means or pivoting devices 29 each having a plurality of capsule chambers 4. The pivot axes 30 of the pivoting device 29 preferably run parallel to one another. The pivoting devices 29 are preferably arranged in a common plane or alternatively offset, arranged above one another or superimposed.

The capsule chambers 4 are preferably intended to be used only once and in particular are already pre-packaged or filled with a capsule 3. The capsule chambers 4 are preferably sealed, particularly by means of covers 12 (not shown) and can be opened individually.

The longitudinal directions or directions of flow of the capsules 3 and capsule chambers 4 preferably run parallel to each other and parallel to the pivot axes 30. Alternatively, however, these may also run transversely and in particular radially with respect to the pivot axes 30.

The pivot devices 29 may if desired be rotatable together or independently of one another. In the former case they may engage, for example, peripherally over their outer circumference with the adjacent pivot device 29 or may be connected by gearing, for example in the manner of a planet gear, particularly via a sun wheel 29a and gear wheels 29b of the pivot devices 29, as shown in FIG. 19 and the schematic section in FIG. 20, or by some other suitable means, for example with an encircling belt, strap or the like.

In addition the arrangement of the pivot devices 29 is preferably rotatable relative to the mouthpiece 10 so that the individual pivot devices 29 can be brought into the inhaling position one after another in order to be able to open the respective capsule chamber 4 and the capsule 3 contained therein and then expel the formulation 2 from the opened capsule 3. Depending on the construction and requirements it is possible for all the capsule chambers 4 of a pivot device 29 to be used one after another for inhalation and only then to switch over to the next pivot device 29, or first of all a capsule chamber 4 of each pivot device 29 is used for inhalation and only afterwards is another capsule chamber 4 of each pivot device 29 used for inhalation.

Figure 21:
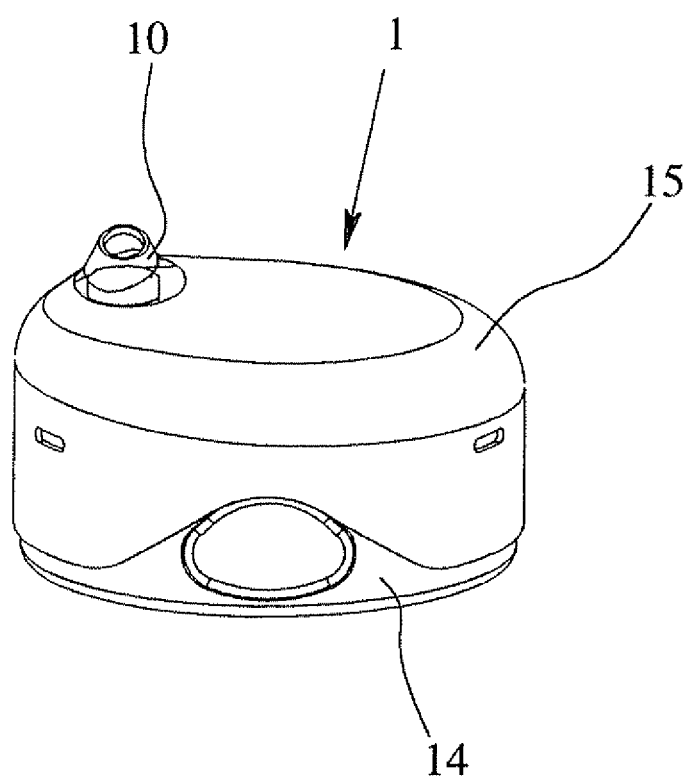
FIG. 21 is a view of the inhaler according to another embodiment in the transportation or inhalation state.
Figure 22:
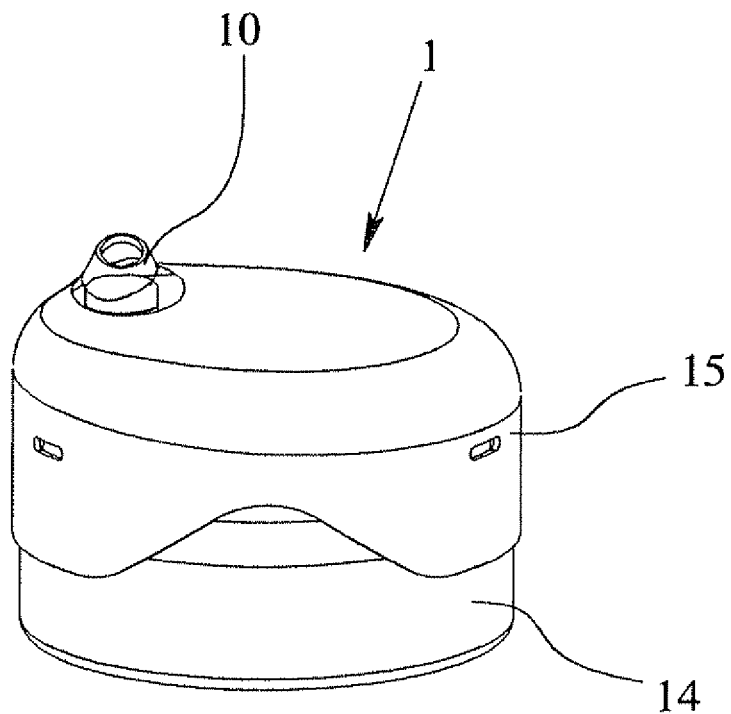
FIG. 22 is a view of the inhaler according to FIG. 21 in an intermediate stage during actuation.

FIGS. 21 and 22 show another embodiment of the proposed inhaler 1. In FIG. 21 the inhaler 1 is in the transporting state of inhalation state. FIG. 22 shows an intermediate phase in which the upper housing part 15 has been rotated in particular through 90° relative to the lower housing part 14 and is preferably axially raised at the same time. Generally, the upper housing part 15 and lower housing part 14 may be any, preferably external parts of the inhaler 1. Preferably, however, the upper part 15 engages over or around the lower part 14 in the manner of a pot, or vice versa.

Figure 23:
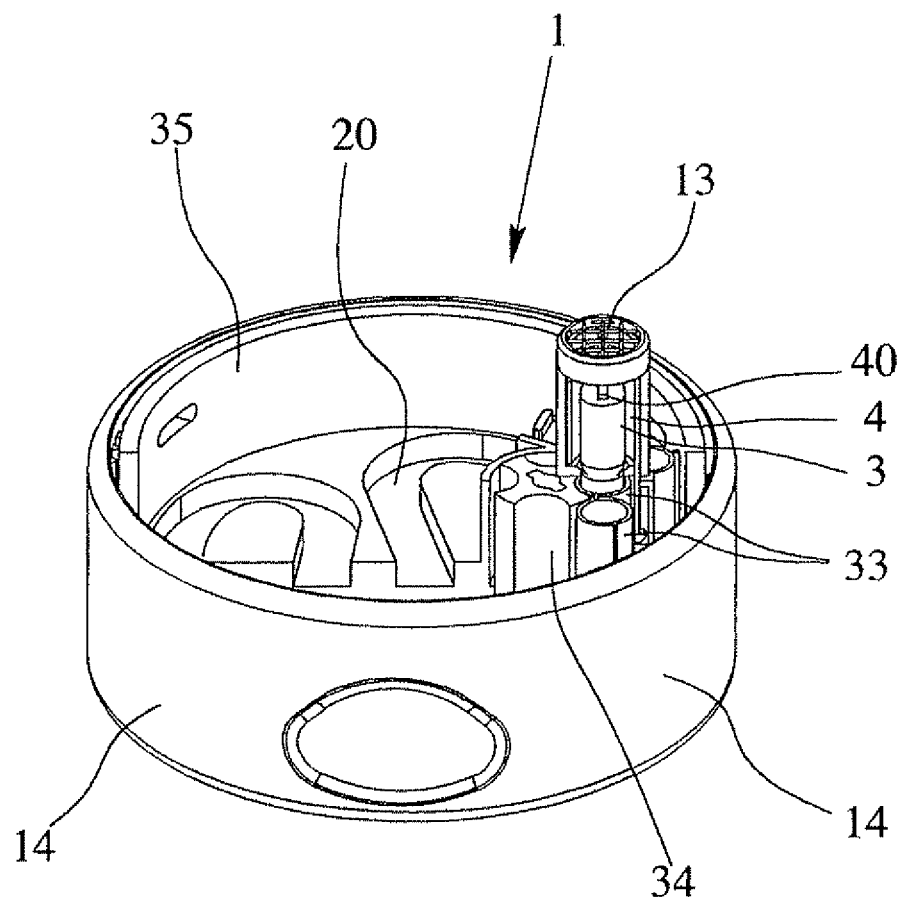
FIG. 23 is a detailed, section-like functional view of the inhaler according to FIG. 21 in the state for transportation or inhalation.
Figure 24:
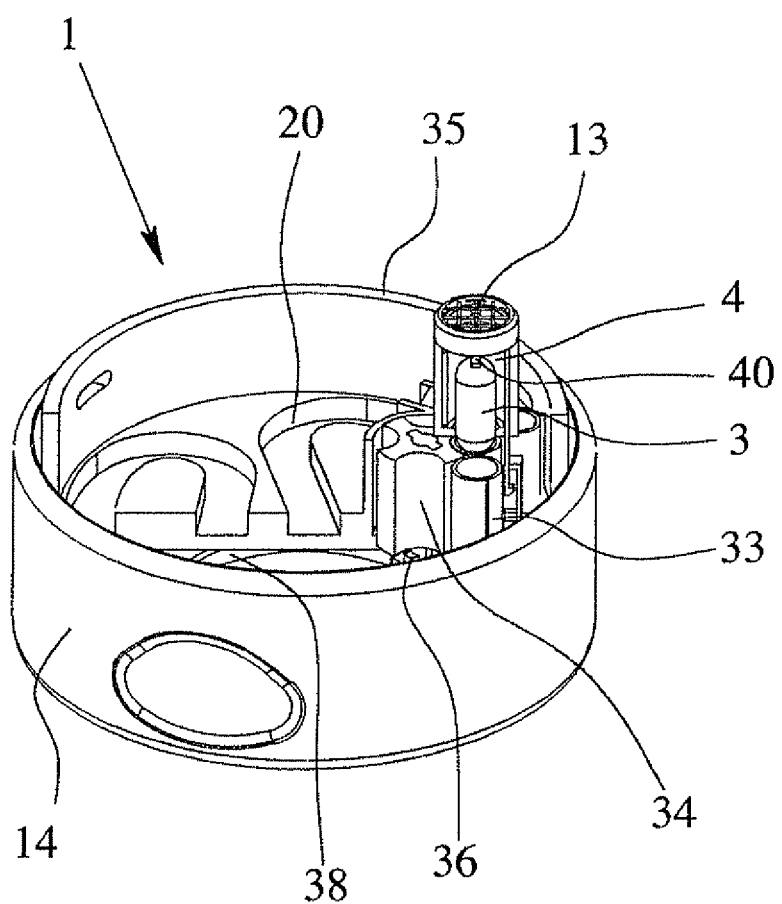
FIG. 24 is a detailed section-like functional view of the inhaler according to FIG. 21 during the initial rotation.

FIG. 23 shows schematically, in a partially sectional view, the inner structure of the opened inhaler 1. The inhaler 1 preferably has only one capsule chamber 4. The capsules 3 which are merely indicated in FIG. 23 are preferably held in a strip (not shown), such as a blister strip, a chain or the like, received for example in preferably sleeve-like receptacles 33 and/or capable of being conveyed by means of a conveying device 34 such as a transporting wheel.

In order to drive it, the inhaler 1 comprises in particular a control sleeve 35 with an associated gear 36 which is rotatable inside the inhaler housing (FIGS. 24 to 27). The control sleeve 35 is preferably provided with the guide 20, particularly in the form of a track or groove for the capsules 3 and preferably carries the conveying device 34, the capsule chamber and/or the opening device 5 (not shown).

The inhaler 1 also comprises a chamber part 26 (not shown) which is constructed here, in particular, as the lower part of the capsule chamber 4, shown in section, and/or in the manner of a push rod and constitutes an element of the device 25 for filling and emptying the capsule chamber 4 with capsules 3.

The method of operation of the inhaler 1 will now be described with reference to FIGS. 23 to 27, which show the inhaler 1 in similar schematic views at different stages. For reasons of simplicity the upper part 15 has been omitted.

In the transporting or resting state shown in FIG. 23 the last capsule 3 which has already been emptied is still in the capsule chamber 4.

The two halves or parts of the housing 14 and 15 are rotated relative to one another. By means of a cam or other geared connection the rotation of the control sleeve 35 relative to the lower housing part 14, in particular, causes the control sleeve 35 to be raised axially from the lower housing part 14. The capsule chamber part 26 is movable along a search in a track but is held axially by a guide 38 on the lower housing part 14. The axial or lifting movement of the control sleeve 35 causes the capsule chamber part 26 to move axially away from the capsule chamber 4, in particular to be withdrawn, by means of a push rod 39 (FIGS. 25, 26), from the receptacle 33 which is provided for the capsule 3 still contained in the capsule chamber 4. Moreover, during the initial rotary movement, the next capsule 3 is opened, particularly pierced, this capsule being located, in particular, in a strip or in the guide 20 or in the next receptacle 33.

Figure 25:
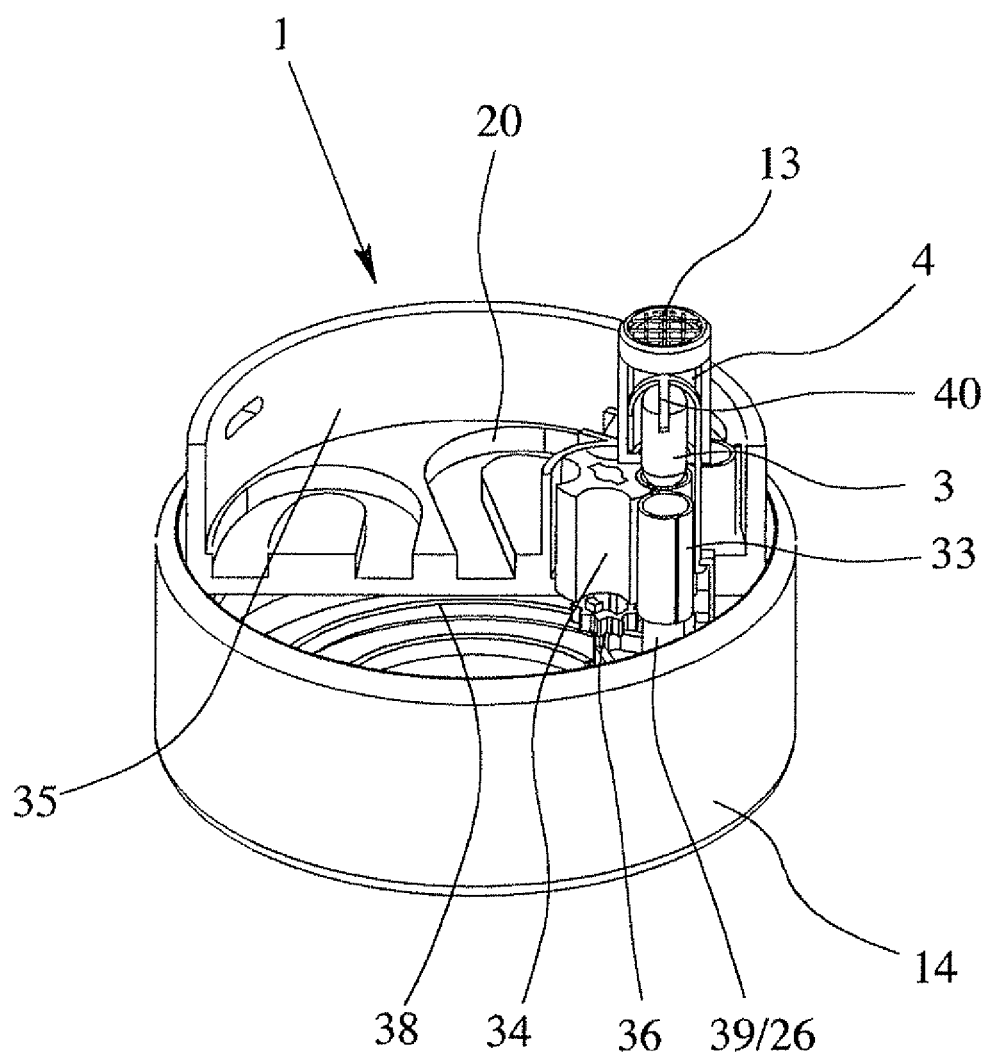
FIG. 25 is a detailed, section-like functional view of the inhaler according to FIG. 21 during further rotation.

FIG. 25 shows a position of further rotation. The push rod has been retracted further from the receptacle 33 for the empty capsule 3 in the strip 44. A resetting element 40, which may optionally also be formed by the lattice 13 or may form the lattice and/or is of a cage-like construction, acts on the capsule 3 and pushes it back into the empty receptacle 33. In addition, the opening device 5 (not shown) with its piercing elements 6 or the like is withdrawn from the following capsule 3 which has already been opened or pierced.

Figure 26:
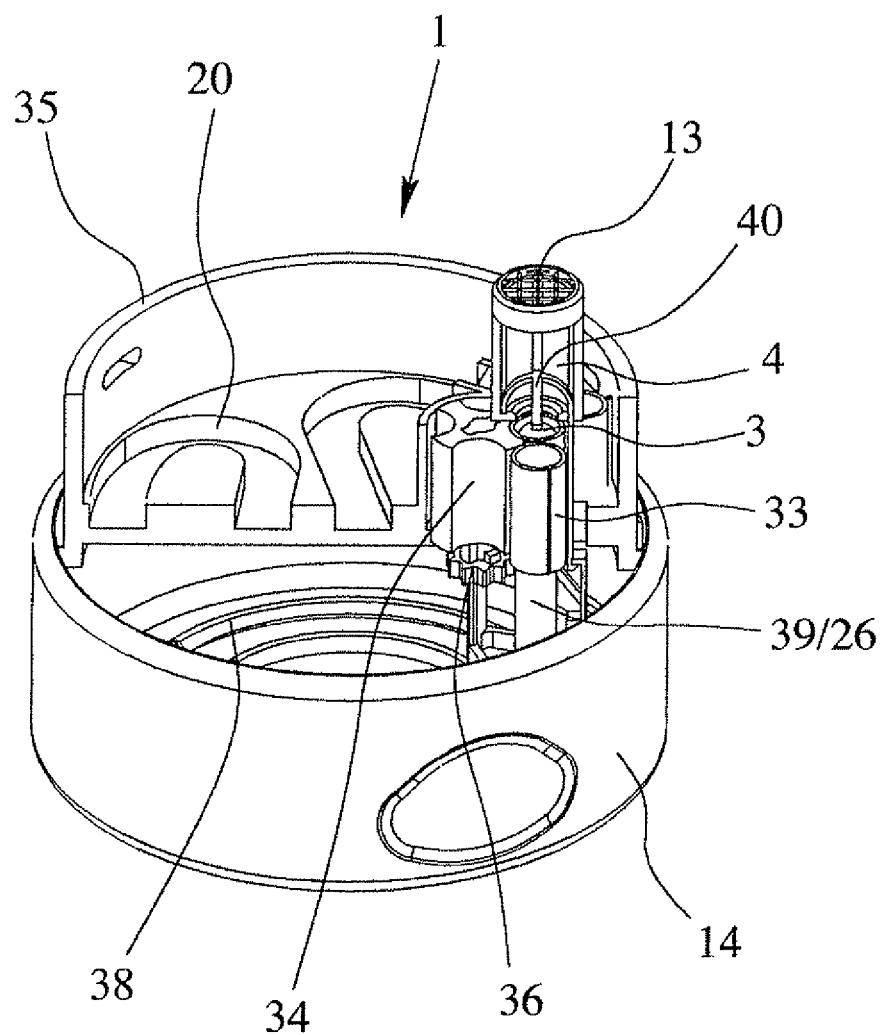
FIG. 26 is a detailed, section-like functional view of the inhaler according to FIG. 21 after rotation through 90°.

The rotary movement or rotation of the upper housing part 15 relative to the lower housing part 14 is continued. FIG. 26 shows a state in which the control sleeve 35 has already been rotated through about 90° or 180° relative to the lower housing part 14. The push rod 39 or the part 26 has been fully retracted from the receptacle 33. The empty capsule 3 has been moved back out of the capsule chamber 4 into the receptacle 33. The piercing elements 6 have again been fully withdrawn from the following capsule 3 and receptacle 33.

The conveying device 34 now advances the capsules 3 or receptacles 33 by one step, and in particular the next, already opened capsule 3 is moved under or into the open capsule chamber 4. This is achieved in particular by advancing the strip 44 formed by the capsules 3 or receptacles 33, for example by rotating the transporting wheel shown, or the like. However, other constructive solutions are also possible.

The conveying device 34 is driven in particular by the gears 36, while corresponding devices such as locking latches, spring elements or the like may be used for the intended stepwise advancement of the capsules 3 or of the strip, in order to achieve the desired, in particular stepwise conveying, which is matched to the other processes.

Figure 27:
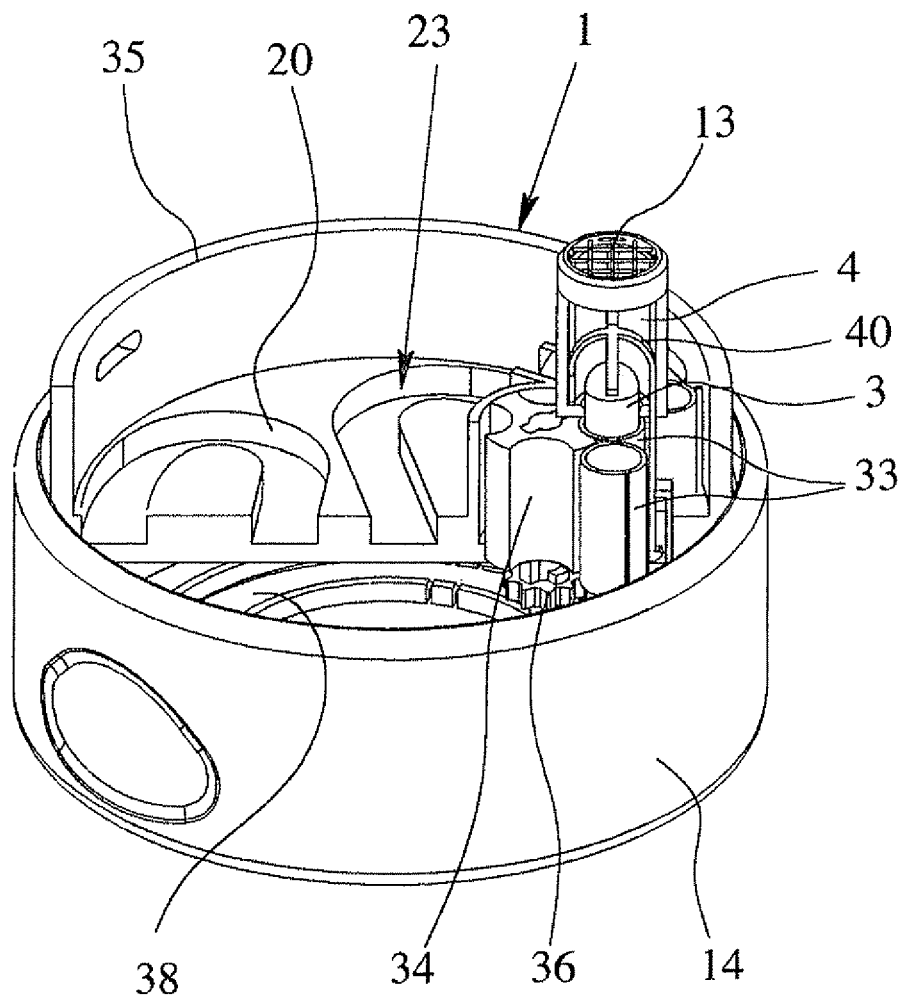
FIG. 27 is a detailed section-like functional view of the inhaler according to FIG. 21 shortly before the rotary movement is completed.

During the further rotation the push rod 39 moves back into the next receptacle 33 and thereby conveys or pushes the next, already opened capsule 3 into the capsule chamber 4, as shown in FIG. 27. This axial movement is achieved in particular by the fact that the control sleeve 35 or the capsule chamber 4 carried by it is moved axially close to the lower housing part 14 or capsule chamber part 26 with the push rod 39, as a result of the cam (not shown).

Finally, as rotation continues, the inhaler 1 returns to the position shown in FIG. 23 in which an opened capsule 3 has been fully inserted in the capsule chamber 4. Inhalation can now take place. The formulation 2 is then expelled, as described previously, with the air flow passing through the capsule chamber 4.

After inhalation no further actuation is necessary, although it is possible. Rather, it is preferable for further actuation to be carried out immediately before the next inhalation or before the delivery of the next dose.

In the embodiment shown, actuation is very simple. In particular, all that is required is to rotate the parts 14, 15 relative to one another. Preferably, in the embodiment shown, rotation through 180° or 360° is necessary in order to run through the procedure described above, i.e. to allow the next dose to be delivered.

According to one particular aspect of the present embodiment, a lifting or axial movement, particularly caused by forcible guiding, is superimposed on the rotary movement. This allows complex or more complicated movements to take place in the inhaler 1, while keeping the operation simple. In particular, the axial enlargement of the inhaler 1 during the actuation gives more room to carry out corresponding processes such as the replacement of the capsule 3 in the capsule chamber 4. However, other constructive solutions are also possible.

The proposed inhaler 1 is preferably provided with a covering cap (not shown) for the mouthpiece 10. To ensure particularly simple operation it may be provided that the covering cap can only be opened once the inhaler 1 has undergone a complete actuation, in particular a complete rotation of the two parts 14 and 15 relative to one another. The covering cap protects the inhaler 1, particularly the capsule chamber 4 and the other air passages from undesirable contamination or the like.

A further advantage of the proposed inhaler 1 is its simple construction from a few parts.

Preferably in the inhaler 1 are formed both a first receiving chamber 23 (FIG. 27) for the unused capsules 3 or the strip 44 or the receptacles 33 containing the unused capsules 3 and a second receiving chamber 24 (not shown) for the used capsules 3 or the strip 44 containing the used capsules 3. Alternatively, however, a common capsule reservoir 31 may also be provided, for example, both for the unused and for the used capsules 3. This makes it possible to reduce the overall height of the inhaler 1 while keeping the same capacity. In the latter case the strip 33 may also be in the form of an endless strip or web, although this is not essential.

Figure 28:
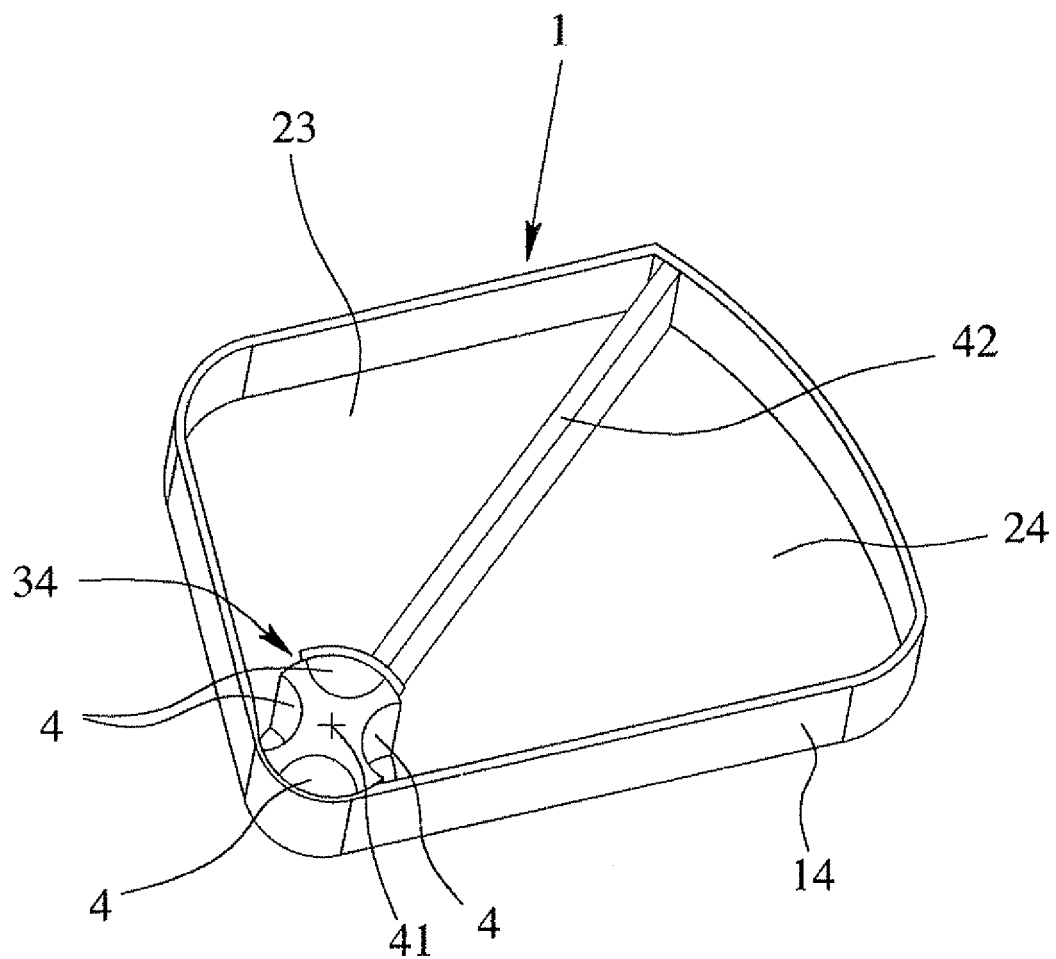
FIG. 28 is a schematic view of an interior of the inhaler according to another embodiment.

FIG. 28 schematically shows the structure of another embodiment of the proposed inhaler 1. The inhaler 1 has a plurality of capsule chambers 4 which are formed by the conveying device 34 or a drive wheel 41. The capsules 3 which are preferably in strip form or loose (not shown) are transported onwards by the rotation of the drive wheel 41 and are accommodated one after the other in the capsule chambers 4 which are preferably initially open at the side. For example, the drive wheel 41 is rotated in steps of 90° (in the embodiment shown, four capsule chambers 4 are formed on the drive wheel 41, arranged uniformly at 90° intervals). Thus, one after the other, one of the capsule chambers 4 containing a capsule 3 is placed or moved into the inhaling position located in the corner of the housing, for example, and is closed off laterally, in particular, by a wall such as the lower housing part 14.

The opening or piercing of the capsules 3 is preferably carried out during or as a result of the conveying, particularly the rotation of the drive wheel 41, so that the next capsule 3 is automatically opened, particularly before it reaches the inhalation position.

An aspect of the present invention which can also be implemented independently of the construction of the drive wheel 41 with capsule chambers 4 consists in the fact that the capsules 3 are preferably opened automatically as they are conveyed along. This can be done by a suitable construction of the opening device 5, the filling device 25, the pivoting device 29, the conveying device 34 and/or the drive wheel 41 or other components of the inhaler 1 and makes operation easier for the user or patient.

In the embodiments shown the inhaler 1 has a first receiving chamber 23 for the unused capsules 3, i.e. those that are still full, and a second receiving chamber 24 for the used, i.e. empty capsules 3. According to a particularly preferred aspect that can also be implemented independently of the functional structure of the present inhaler 1 as described hereinbefore, a moveable, flexible and/or elastic partition wall 42 is preferably provided between the two receiving chambers 23 and 24. This results in a particularly compact structure as a result of corresponding displacement, deformation or other modification of the partition wall 42, as the total space available for the receiving chambers 23 and 24 can be utilised to an optimum degree, preferably initially only for the first receiving chamber 23, essentially, containing the filled capsules 3. As the use increases, the receiving chamber 23 becomes smaller as a result of the movement, displacement and/or deformation of the partition wall 42 and by contrast the second receiving chamber 24 for receiving the used empty capsules 3 is made larger. If necessary the separating wall 42 can also be in the form of an elastic strip, moveable segment, foil or the like.

The moveable and/or deformable partition wall 42 can also be used accordingly to separate two receiving chambers 23, 24 for capsule chambers 4, particularly unused capsule chambers 4 on the one hand and used capsule chambers 4 on the other hand.

Figure 29:
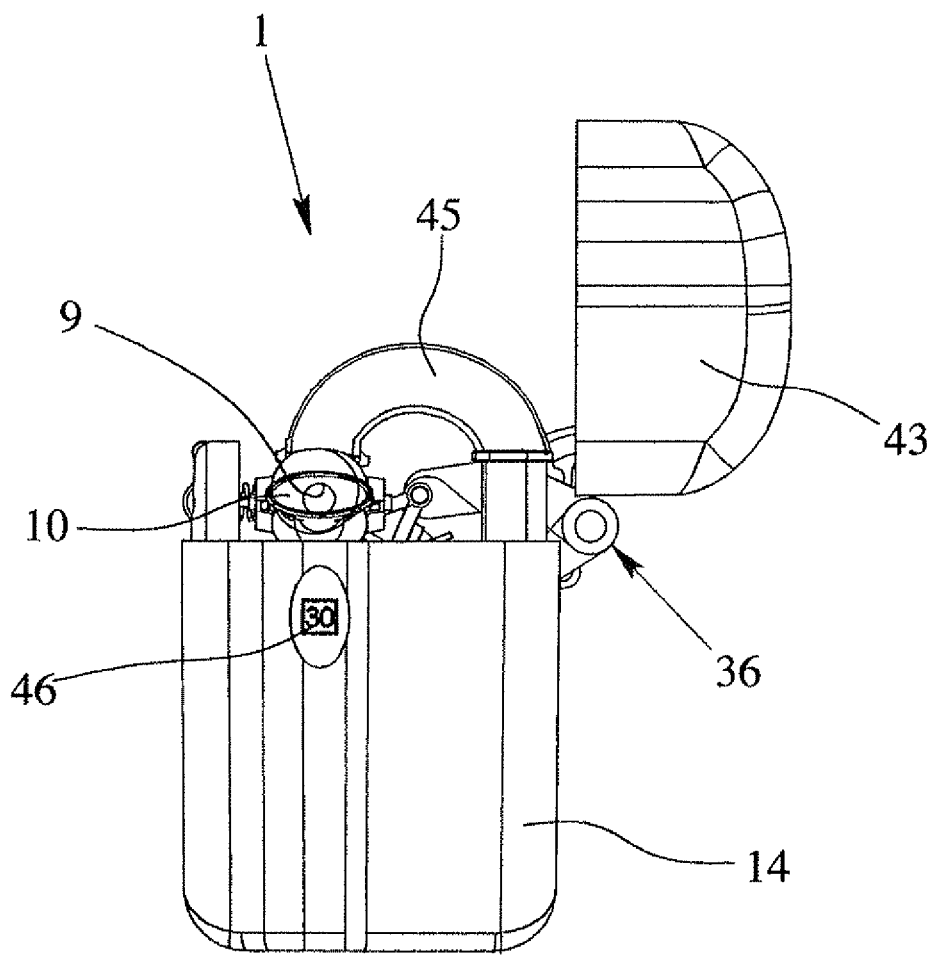
FIG. 29 is a schematic view of the inhaler according to another embodiment.
Figure 30:
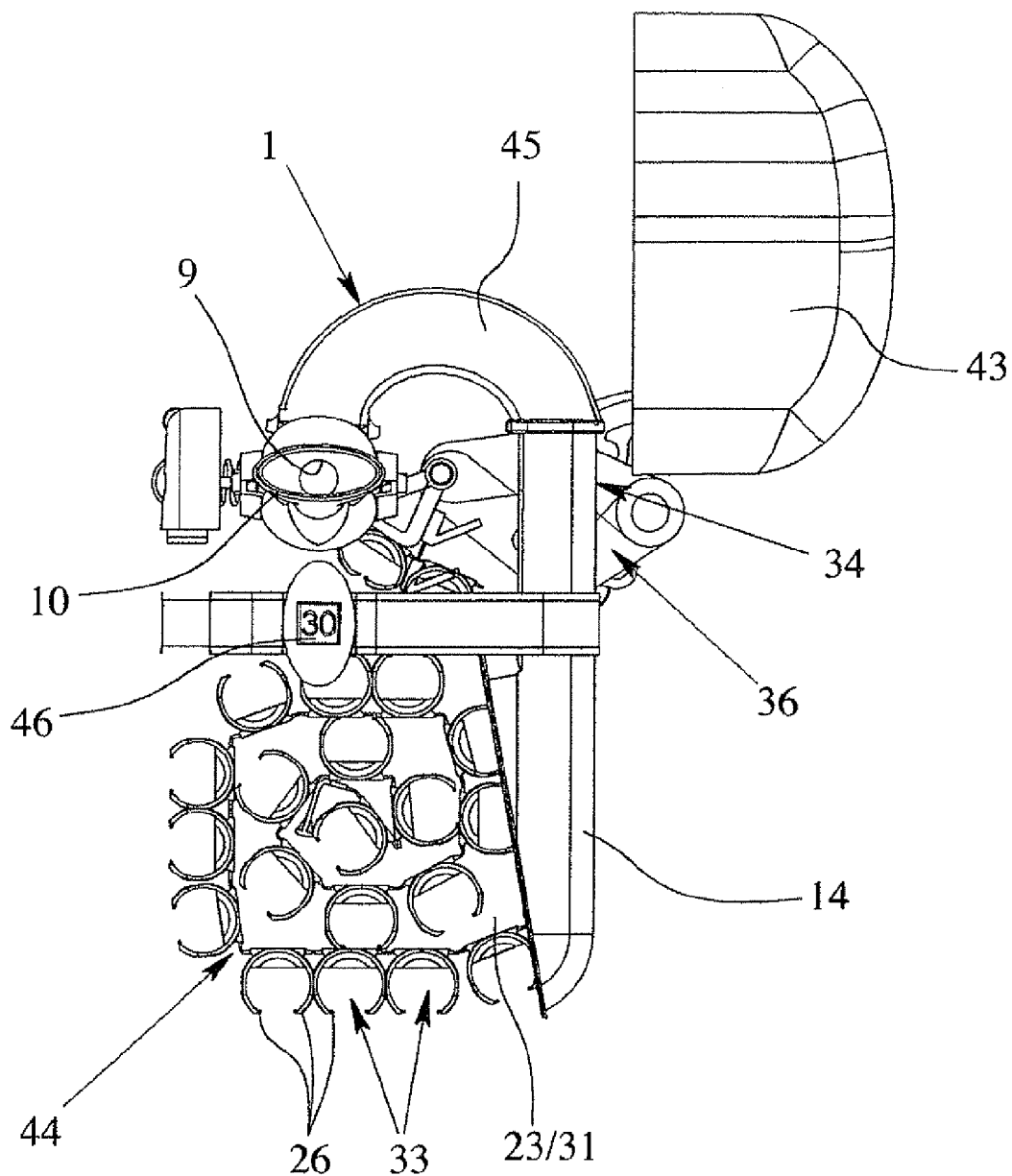
FIG. 30 is a schematic, partially sectional view of the inhaler according to FIG. 29.
Figure 31:
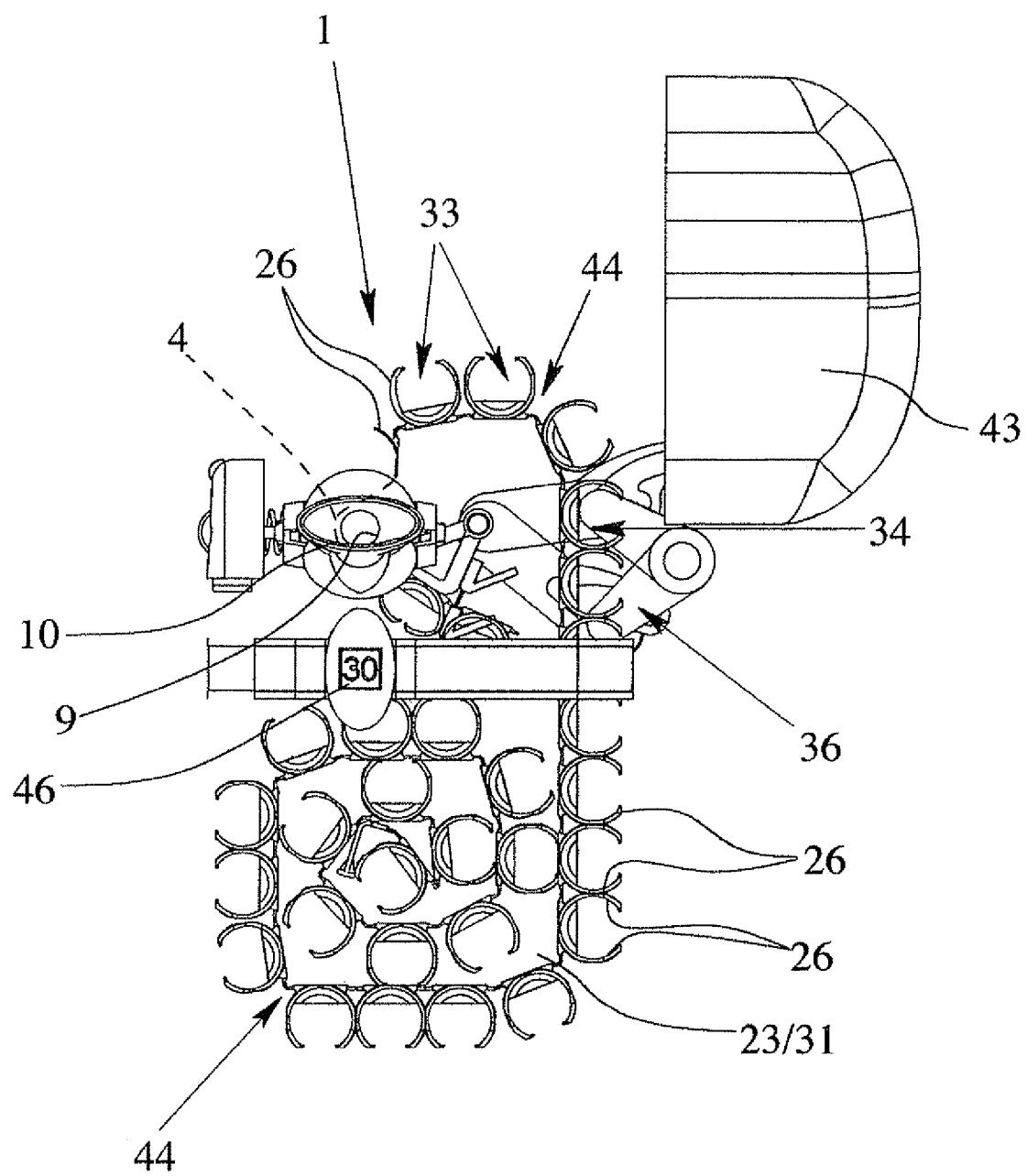
FIG. 31 is another, head-on view of the inhaler according to FIG. 29.

FIG. 29 shows another embodiment of the proposed inhaler 1 with its covering cap 43 open and its mouthpiece 10 folded out. FIG. 30 shows an enlarged view, partially in section, while FIG. 31 shows another enlarged view partially in section.

The capsules 3 (not shown) are preferably accommodated in a chain or a strip 44 or form such a chain or strip, which is accommodated, preferably in a coil, in a first receiving chamber 23 or capsule reservoir 31. The strip 44 has receptacles 33 for the individual capsules 3, which are preferably formed by capsule chamber segments or parts 26 or form such segments or parts.

The strip 44 with the capsules 3 is guided into the region of the mouthpiece 10, in particular via a channel 45. The capsule chamber 4, which is not individually shown, is arranged there. Conveying is carried out by means of the conveying device 34, which is preferably actuated by opening and closing the covering cap 43. The following sequence is possible, for example.

Starting from the closed position, the covering cap 43 is flipped open. To begin with, no action is required. Starting from a certain pivot angle, further conveying of the strip 44 or of the capsules 3 takes place, and preferably opening, particularly piercing, of the next capsule 3 by means of the opening device 5 which is not shown here. Thus the capsules 3 are opened automatically. The drive or actuation are carried out in particular by means of the gear 36 which is constructed in this case as a lever mechanism and is associated with the covering cap 43.

The next receptacle 33 is conveyed, as the advance continues, with the opened capsule 3 to the capsule chamber 4 shown in FIG. 31, which extends in particular at right angles to the plane of the drawing and/or the direction of travel, so that the receptacle 44 with its capsule chamber segment or part 26 closes off the capsule chamber 4. The capsule chamber part 26 which consists, for example, of an elastic or relatively rigid plastic material can be deformed elastically or inelastically. This allows expansion to take place, for example, in order to achieve the desired size of capsule chamber. Alternatively or in addition, this may contribute to total closure of the capsule chamber 4 or good sealing of the capsule chamber 4.

Once the covering cap 43 has opened far enough, for example more than 90° and in particular more than 130°, and accordingly the next capsule 3 has been opened and conveyed into the capsule chamber 4 and the capsule chamber 4 has been closed, the mouthpiece 10 can be flipped outwards and inhalation may take place. This condition is illustrated in FIG. 30.

After inhalation, the mouthpiece 10 is folded in again and the covering cap 43 is closed again. The closing of the covering cap 43 causes the used or emptied capsule 3 to be discharged into the receiving chamber 23 or capsule reservoir 31. According to a particularly preferred aspect which can also be implemented independently, the used capsule 3 is compressed and/or shredded or otherwise comminuted in order to minimise the storage space needed in the inhaler 1 and hence also the overall height of the inhaler 1. Alternatively or in addition, the receptacle 33 or the used capsule strip 44 or the like is compressed, shredded, cut up or in some other way treated in order to minimise the storage space required.

If the inhaler 1 is designed to accommodate used capsules 3, capsule chambers 4 and/or parts or segments 26 thereof, the second receiving chamber 24 or the like required for this purpose is preferably separated from other parts, sections or areas of the inhaler 1, particularly from the first receiving chamber 23, and is preferably formed by the partition wall 42, which may in particular also be formed by a foil. Alternatively or additionally, such a separation may also be provided for non-emptied capsules 3 or unused capsule chambers 4 or the first receiving chamber 23 and may serve in particular as a protection against moisture.

If a plurality of capsule chambers 4 are provided these may be compressed and/or shredded, cut up or otherwise treated after use in order that they can be accommodated or stored as compactly as possible in the inhaler 1.

The proposed inhaler 1 is preferably provided with a counter 46 which can for example count the number of capsules 3 already used or those which have not yet been used and display the number. The counter 46 may for example be coupled to the gear 36, the covering cap 43, the conveying device 34, the strip 44 or the mouthpiece 10 and/or a sensor (not shown) for detecting inhalation and may optionally be driven or actuated thereby.

Figure 32:
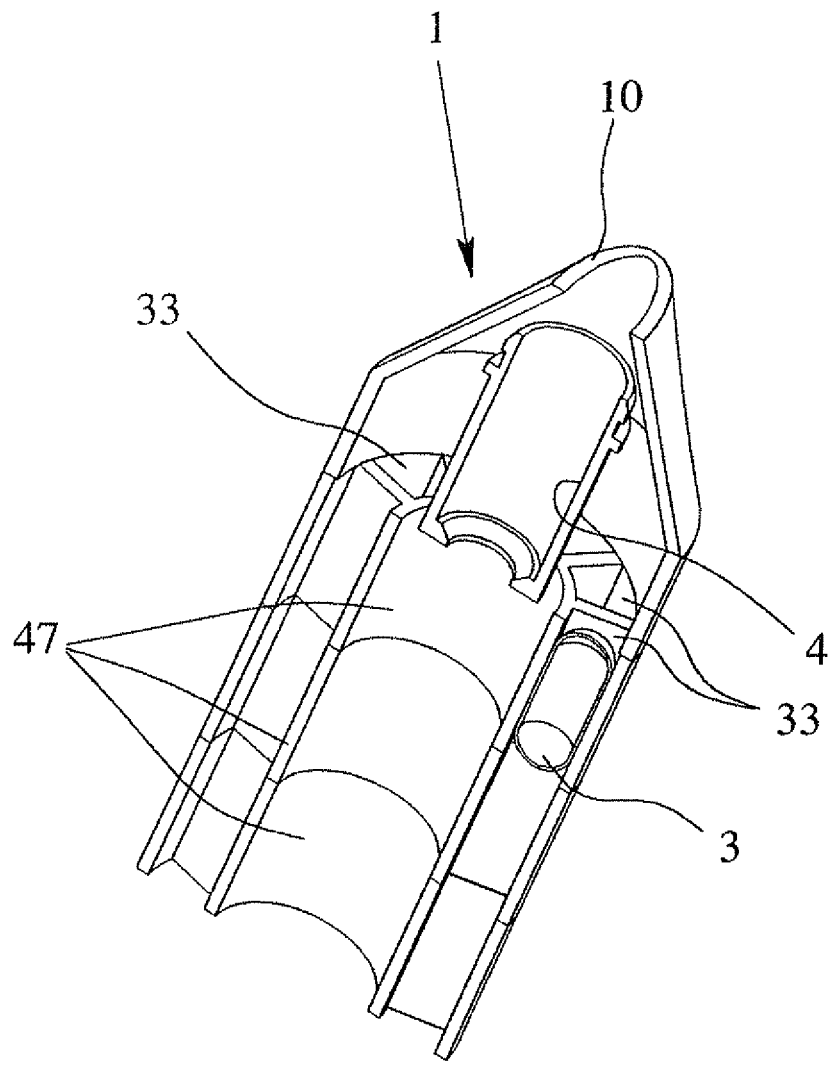
FIG. 32 shows a schematic, section-like structure of the inhaler according to another embodiment.

FIG. 32 shows a schematic sectional view of another embodiment of the proposed inhaler 1 with rotatable rings or segments 47. As the rings or segments 47 are rotated, any capsules 3 contained therein, e.g. in segment-like chambers or receptacles 33 (only one such capsule 3 being shown in FIG. 32, by way of example) are supplied one after another to a central capsule chamber 4 where they are pierced. After inhalation the used capsules 3 are received in the rings or segments 47 or receptacles 33 once more or expelled.

Figure 33:
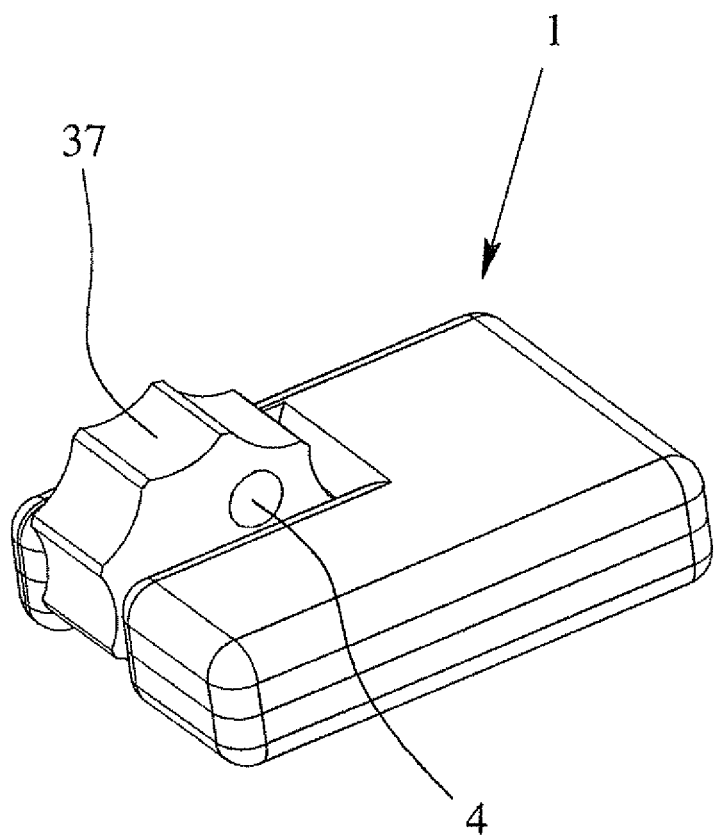
FIG. 33 shows a schematic construction of the inhaler according to another embodiment.

FIG. 33 shows a diagram of the inhaler 1 according to another embodiment. The inhaler here has a preferably manually rotatable control wheel 37 with the capsule chamber 4. Preferably, the capsule chamber 4 can be filled manually with a capsule 3 (not shown) and then rotated to open the capsule 3 and enable inhalation into the inhaler housing.

Figure 34:
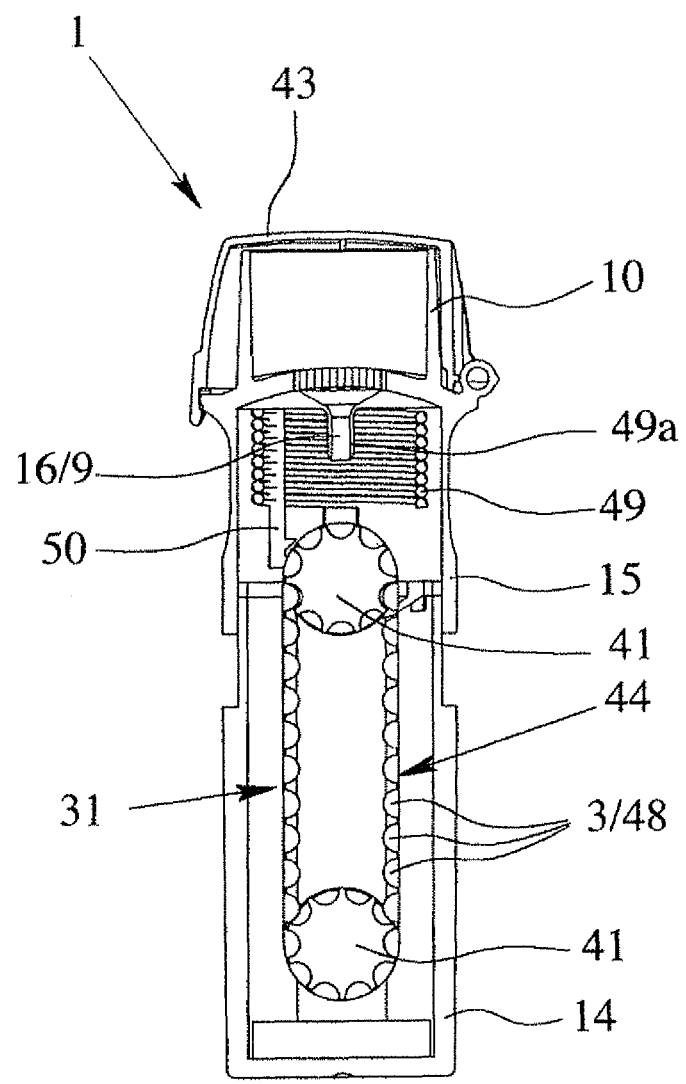
FIG. 34 shows a schematic section through the inhaler according to another embodiment.

FIG. 34 shows, in schematic section, another embodiment of the proposed inhaler 1 with an endless strip 44 which runs around drive wheels 41. The strip 44 may have receptacles 33 for capsules 3 (not shown). Preferably the capsules 3 for the purposes of the present invention are formed by blister pouches 48 or other receptacles for the formulation 2. The capsules 3 are in this case fixedly connected to one another, in particular.

By axially pushing the lower housing part 14 and upper housing part 15 of the inhaler 1 together, particularly counter to the force of a spring 49, the strip 44 is advanced by one step or one position or blister pouch 48 in order to move the next capsule 3 or blister pouch 48 into the inhaling position underneath the mouthpiece 10, so that this capsule 3 or blister pouch 48 can be emptied during the next inhalation by expulsion of the formulation 2 contained therein. The opening, particularly piercing, is preferably carried out by the opening device 5 (not shown), particularly by having a spike 49a or the like, as shown, penetrate into the blister pouch 48 shortly before it reaches the pushed-together position.

Figure 35:
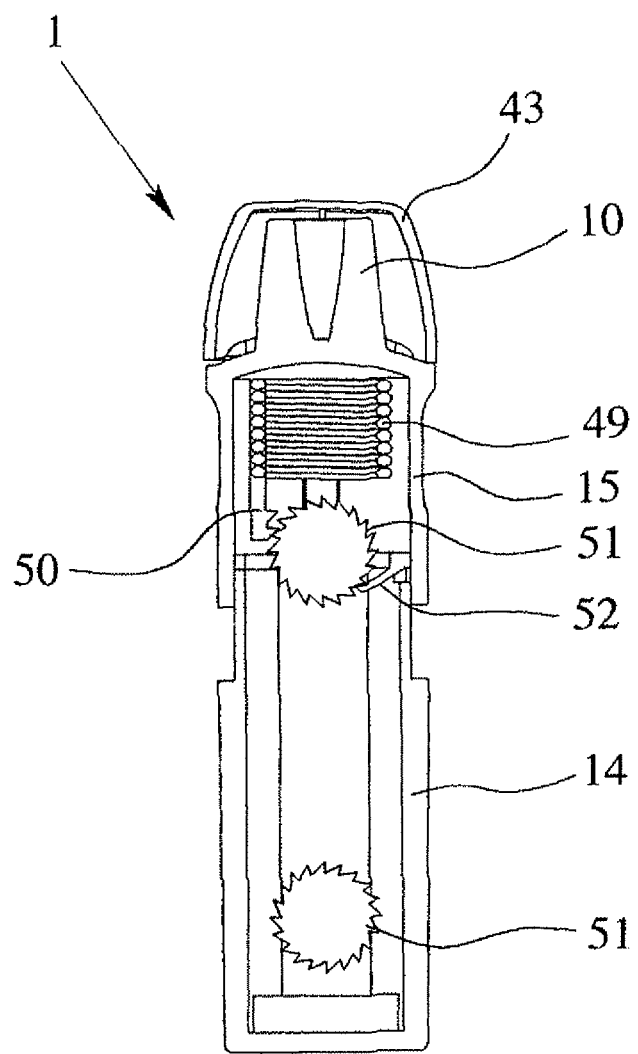
FIG. 35 shows another section through the inhaler according to FIG. 34.

FIG. 35 shows, in another section, a possible embodiment of the drive. An engagement hook 50 is moveable back and forth, tangentially to a gear rim 51 of a drive wheel 41, as the housing parts 14 and 15 are pushed together and moved apart, so that the gear wheel 41 is rotated stepwise in one direction, as a locking pawl 52 preferably also engaging the gear rim 51 prevents it from rotating back again.

In the transporting or delivery position the inhaler is preferably pushed together. In particular, the housing parts 14 and 15 are joined together, preferably latching with one another, by means of at least one snapping hook or the like (not shown) in the compressed state. This engagement can be released by manual operation. The spring 49 then causes the two housing parts 14 and 15 to move apart, more particularly in the longitudinal direction, so that the state shown in FIGS. 34 and 35 is achieved once more.

Figure 36:
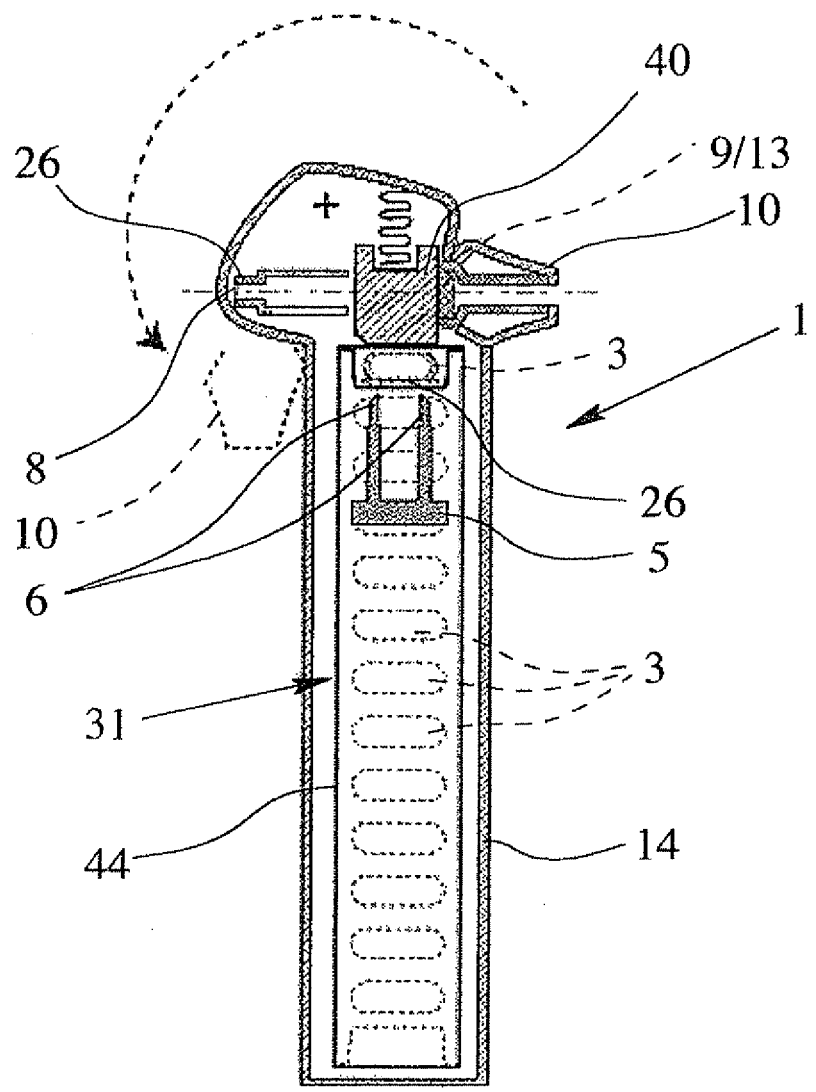
FIG. 36 shows a schematic section through the inhaler according to another embodiment.

FIG. 36 shows, in schematic section, an inhaler 1 similar to the previous embodiment. In the illustration, the capsules 3 are accommodated by the strip 44 or in receptacles 33 or blister pouches 48 and can be removed separately, in particular.

In contrast to the previous embodiment with an axial direction of delivery, the mouthpiece 10 here has a preferably transverse or radial direction of delivery and alignment for inhalation, in relation to the longitudinal direction of the inhaler 1 or the preferably elongate or rod-like lower housing part 14.

The mouthpiece 10 can preferably be flipped away into the position shown by dotted lines, from the position of inhalation shown. This flipping or folding movement is preferably used to actuate or drive the inhaler 1 or the opening device 5, the conveying device 34, a drive wheel 41 or to advance the strip 44, e.g. using the gear 16 (not shown).

Figure 37A:
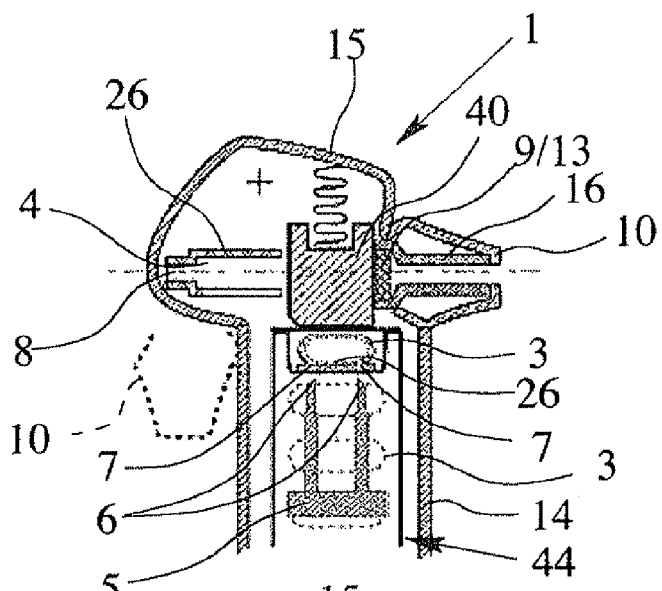
FIG. 37a shows a detailed schematic section through the inhaler according to FIG. 36 in a first state.
Figure 37B:
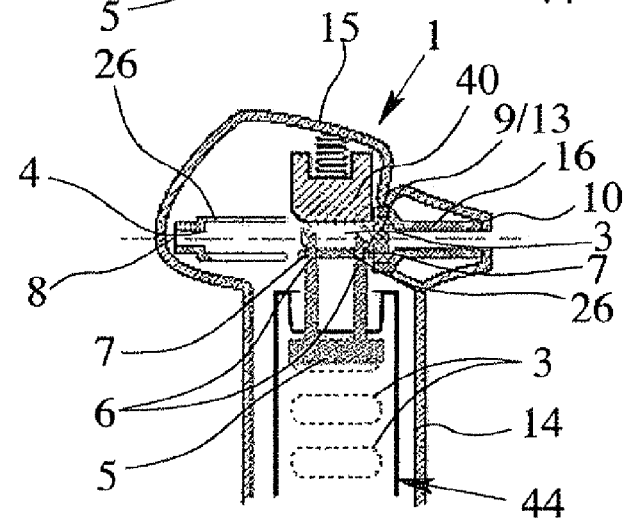
FIG. 37b shows a detailed schematic section through the inhaler according to FIG. 36 in a second state.
Figure 37C:
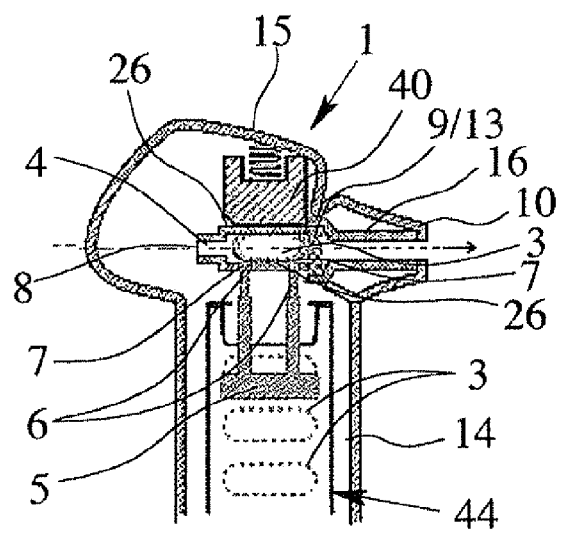
FIG. 37c shows a detailed schematic section through the inhaler according to FIG. 36 in a third state.

FIGS. 37a to 37c show different states of the preferred operation, in schematic sections of details.

FIG. 37a shows a first state. There is still no capsule 3 in the position of inhalation or in the capsule chamber 4. A first capsule chamber part 26 has moved away from the capsule chamber 4 counter to the direction of delivery or main direction of flow. The capsule chamber 4 is open at the side.

FIG. 37b shows a second state. The opening device 5 has moved or displaced the capsule 3 intended for the next inhalation, counter to the force of the preferably spring loaded resetting element 40, and in particular has pierced it laterally with the piercing elements 6, together with a second, particularly beam-like capsule chamber part 26 from the blister pouch 48 into the capsule chamber 4 or into the extension of the mouthpiece 10 which is in the inhaling position.

FIG. 37c shows a third state. The opening device 5 is withdrawn from the capsule 3 with its piercing elements 6, particularly only to a point where piercing openings 7 formed in the second capsule chamber part 26 remain closed off by the piercing elements 6, in order to ensure the desired air flow (longitudinally through the capsule chamber 4). Moreover the first capsule chamber part 26 has been pushed forward. The capsule chamber 4 is thus closed. The inhaler 1 is ready for inhalation.

When the opening device 5 is pushed back into its starting position and the capsule chamber 4 is opened, the preferably spring loaded resetting element 40 returns the emptied capsule 3 to the empty blister pouch 48 or receptacle 33 in the strip 44. The strip 44 can then be moved on to the next capsule 3.

In the embodiments shown, a second capsule chamber part 26 is provided in each receptacle 33 or blister pouch 48. Alternatively, only one capsule chamber part 26 may be provided which is then preferably not detachable from the piercing elements 6.

FIG. 38a shows another embodiment of the inhaler 1 with a receiving chamber 23 or capsule reservoir 31 in a schematic section. Each capsule 3 is pre-packaged in a capsule chamber 4, as shown in section in FIG. 38b.

The capsule chambers 4 with the capsules 3 are in particular contained in a meandering or other configuration in the inhaler 1 or receiving chamber 23 or reservoir 31 and can preferably be advanced by means of at least one and in particular for transporting or driving wheels 41 individually to the mouthpiece 10.

The capsule chamber 4 intended for the next inhalation is preferably picked up by the conveying device 34, particularly a manually operable actuating element 53, which can be pressed in this case, in the desired alignment axially to the mouthpiece 10, opened on the inlet and outlet sides, moved towards the opening device 5 for opening or piercing the capsule 3 and/or finally connected to a connecting member 16 associated with the mouthpiece 10 on the outlet side, as shown in the enlarged detail in FIG. 38c. The delivery of the formulation 2 or inhalation can then take place.

After the inhalation, the used capsule chamber 4 with the emptied capsule 3 is picked up again by the conveying device or the receiving chamber 23 or the reservoir 31, particularly by means of the next transporting or drive wheel 41.

Figure 39:
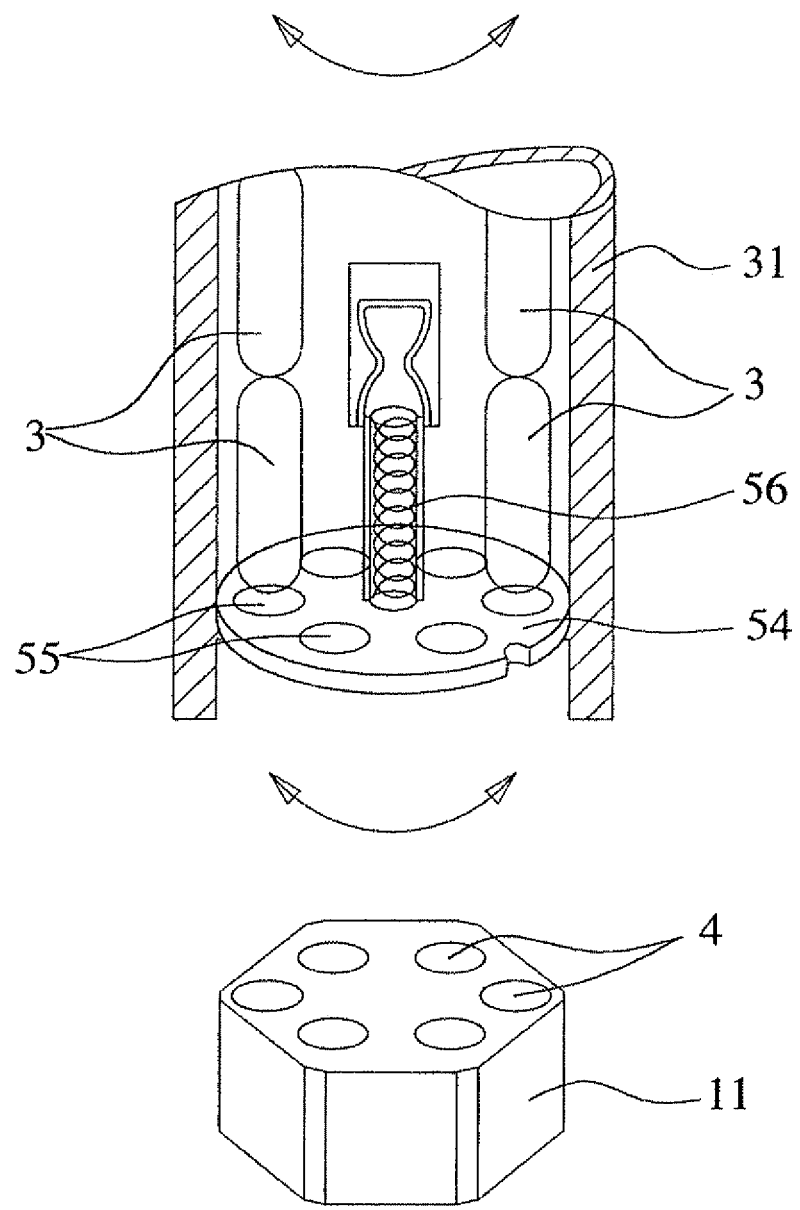
FIG. 39 shows a schematic sectional structure of a reservoir of the inhaler according to another embodiment.

FIG. 39 shows another embodiment with a capsule reservoir 31, shown as a partial section. The capsule reservoir 31 is of tubular design. The capsules 3 are preferably contained therein axially one behind the other and distributed around the circumference of the capsule reservoir 31.

The capsule reservoir 31 is in particular designed for the group expulsion of capsules 3, for example six capsules 3, to be held in a carrier 11 which is correspondingly provided with six capsule chambers 4, for example. It has a preferably shutter-like gate or exit 54 with openings 55 corresponding to the number of capsules 3 to be discharged simultaneously. The gate is preferably rotatable counter to the force of a spring 56 such that the openings 55 can be aligned on an extension of or axially with respect to the capsules 3, so that the capsules 3 are discharged through the openings 55 and caught by the magazine or carrier 11 located underneath. After the expulsion the gate 54 closes automatically as a result of spring force or turning back.

Figure 40:
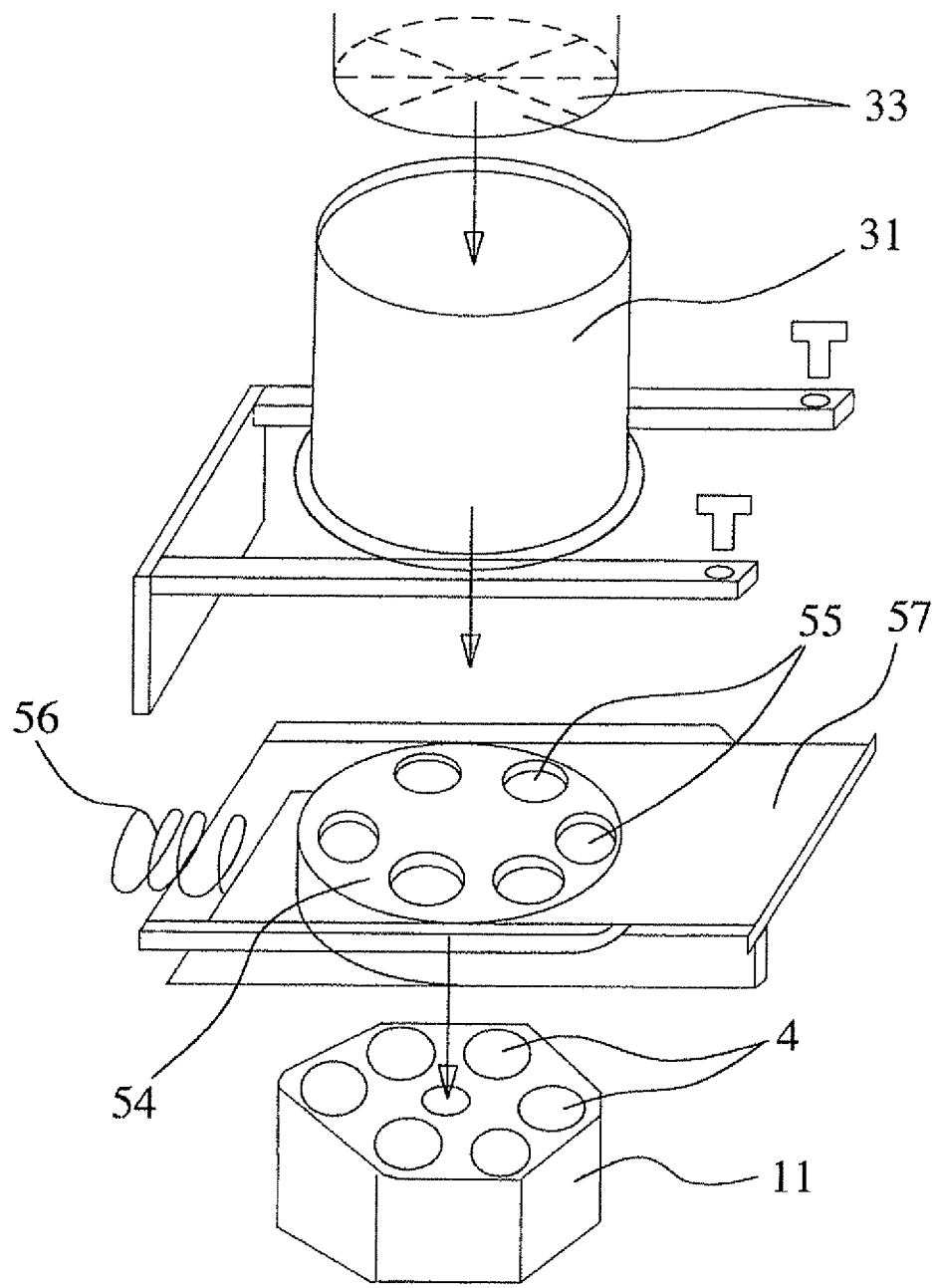
FIG. 40 shows a schematic sectional structure of a reservoir of the inhaler according to another embodiment.
Figure 41:
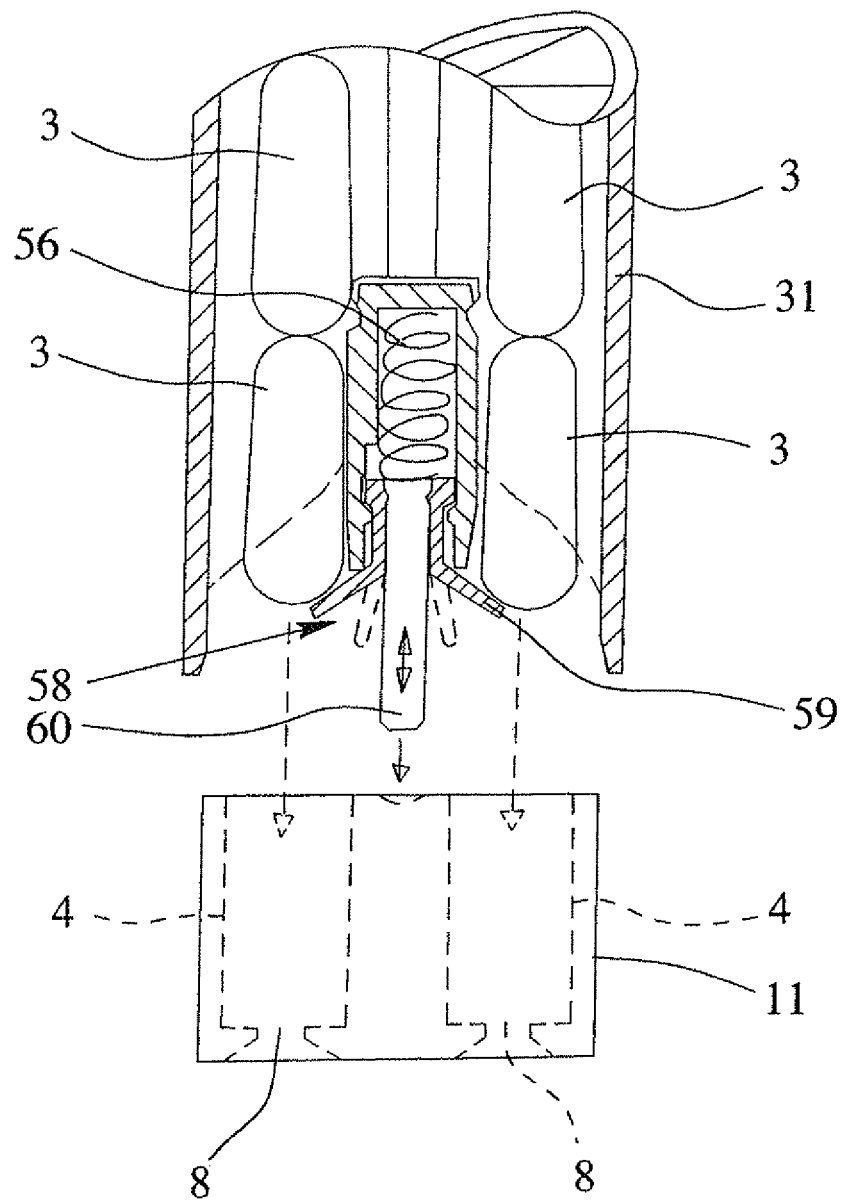
FIG. 41 shows a schematic sectional structure of a reservoir of the inhaler according to another embodiment.
Figure 42:
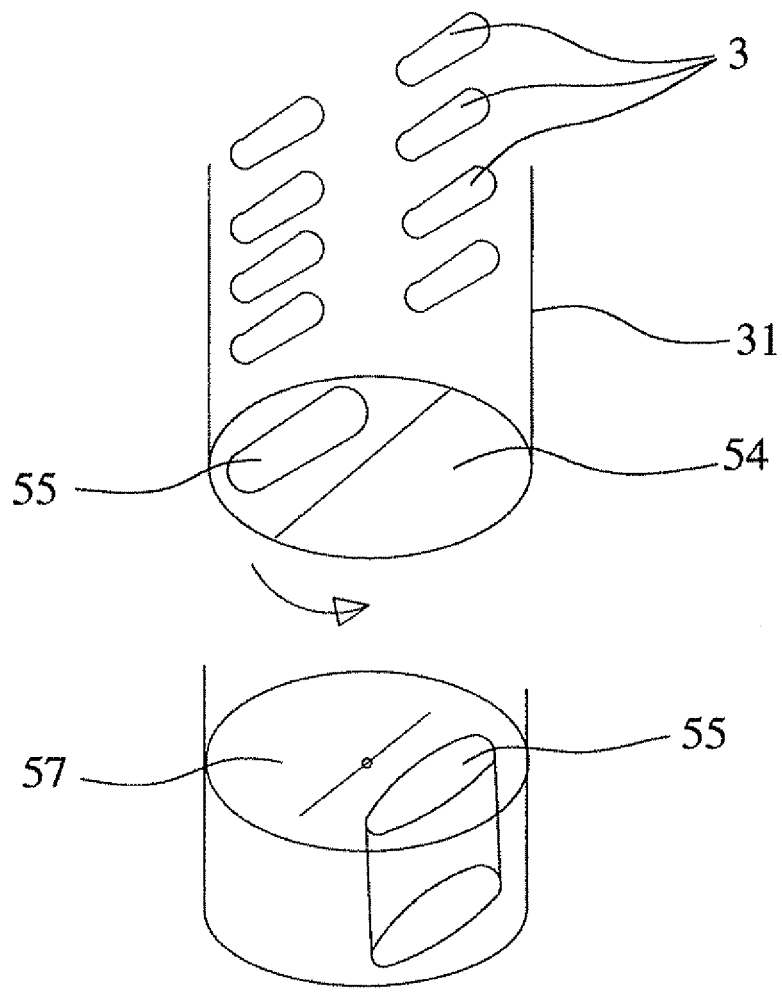
FIG. 42 shows a schematic sectional structure of a reservoir of the inhaler according to another embodiment.

FIGS. 40 to 42 show similar embodiments of the capsule reservoir 31.

In the embodiments shown in FIG. 40 the gate 54 can be closed off by an associated slide-like shutter 57 which is moveable transversely or radially counter to the force of the spring 56 for expelling the capsules, i.e. for opening the gate 54 or exposing the openings 55. In the interests of simplicity, FIG. 40 does not show any capsules 3.

In the embodiments shown in FIG. 41 the capsule reservoir 31 has a preferably central holding device 58 which blocks axial movement of the capsules 3 by means of arms 59 spreading radially in the blocked position. When the carrier 11 presses axially on a pin 60 of the holding device 58, it releases the capsules 3 by folding the arms 59 radially against the pin 60, as shown by dotted lines in FIG. 41. The next group of capsules 3 can then slide into the carrier 11 located below or its capsule chambers 4. When the carrier is removed, resetting takes place as a result of the spring 56, the arms 59 spread out again and the holding device 58 prevents any further expulsion of capsules 3.

In the embodiment according to FIG. 42 the capsule reservoir 31 receives the capsules 3, preferably in an alignment at right angles to the longitudinal direction of the capsule reservoir 31. The capsules 3 are arranged either in two rows or stacks in the axial direction of the capsule reservoir 31 or along a coil or helical line in the capsule reservoir 31. The gate 54 comprises, in particular, only one opening 55. As the shutter 57 is rotated or turned stepwise, so that its opening 55 is brought into alignment with the opening 55 in the gate 54, the capsules 3 are preferably expelled singly. In particular, one capsule 3 can be expelled in a specific rotational position of the shutter 57. In the opposite position of rotation or the position shown in FIG. 42 which is rotated through 180°, in particular, the capsule reservoir 31 is preferably tightly sealed, particularly to protect the capsules from excessive climatic fluctuations and/or prevent the capsules 3 from drying out too much.

Figure 43:
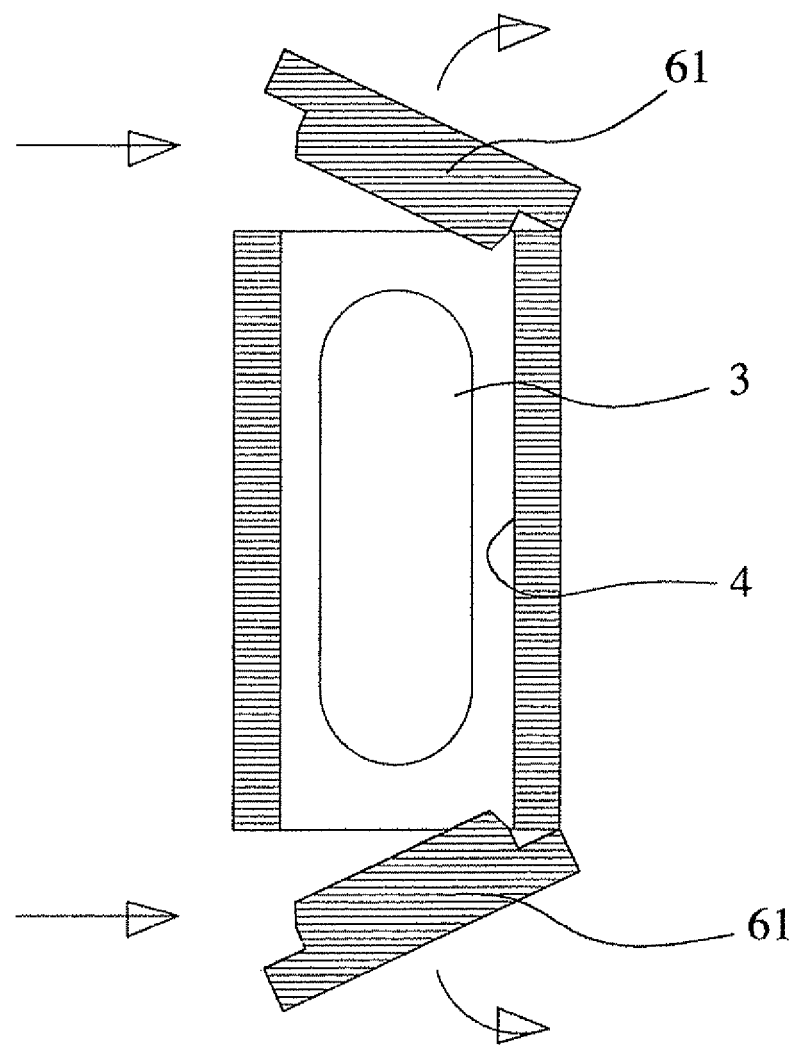
FIG. 43 shows a schematic section through a carrier or a capsule chamber of the inhaler according to another embodiment.

FIG. 43 shows a section through an embodiment in which the capsule chamber 4 can be closed off or is closed off on the inlet and/or outlet side by removable stoppers 61 or other closure elements such as caps, lids or the like.

Figure 44:
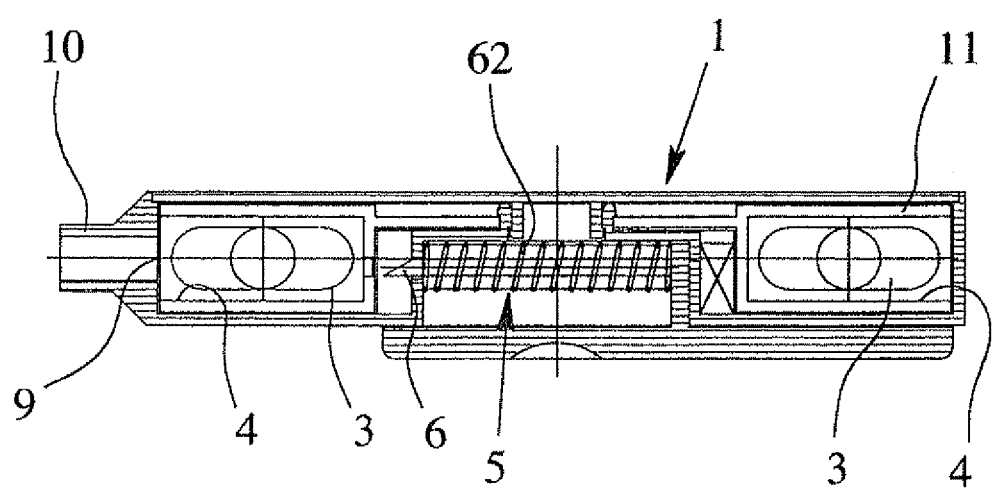
FIG. 44 shows a schematic section through the inhaler according to another embodiment.

FIG. 44 shows in a schematic section another embodiment of the inhaler 1. The capsule chambers 4 and capsules 3 are radially aligned in the rotatable annular carrier 11. The piercing of the capsules 3 by the opening device 5 in the position of inhalation also takes place radially, i.e. axially or at the end face relative to the capsules 3. The opening device 5 has in this case a resetting spring 62 which preferably surrounds the piercing element 6 and can be actuated in particular in the manner of a slide counter to the force of the resetting spring 62.

Figure 45:
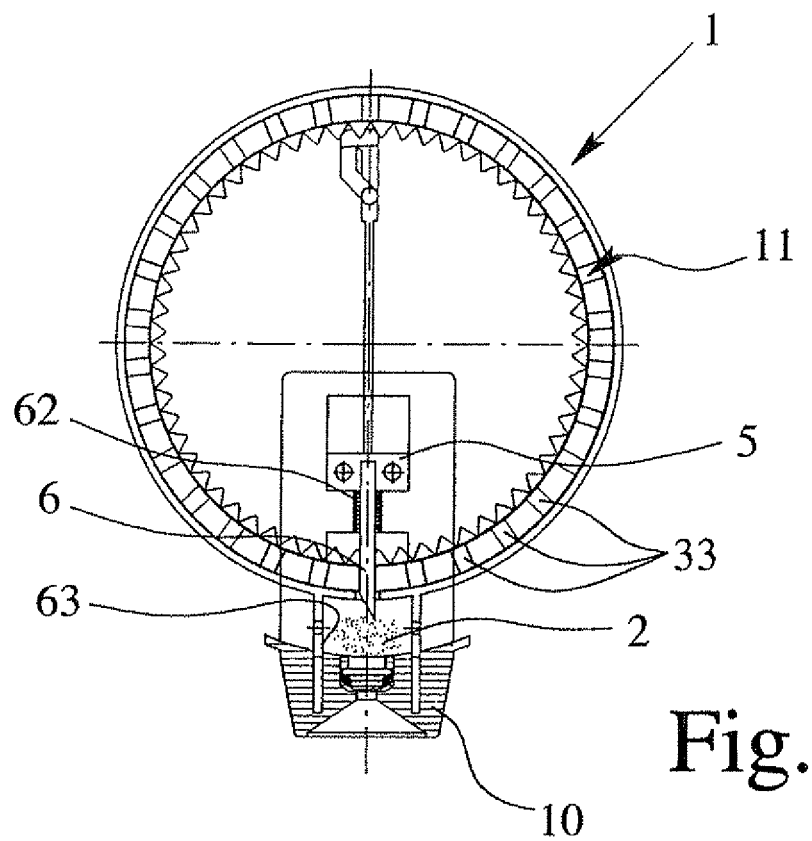
FIG. 45 shows a schematic section through the inhaler according to another embodiment in a first state.
Figure 46:
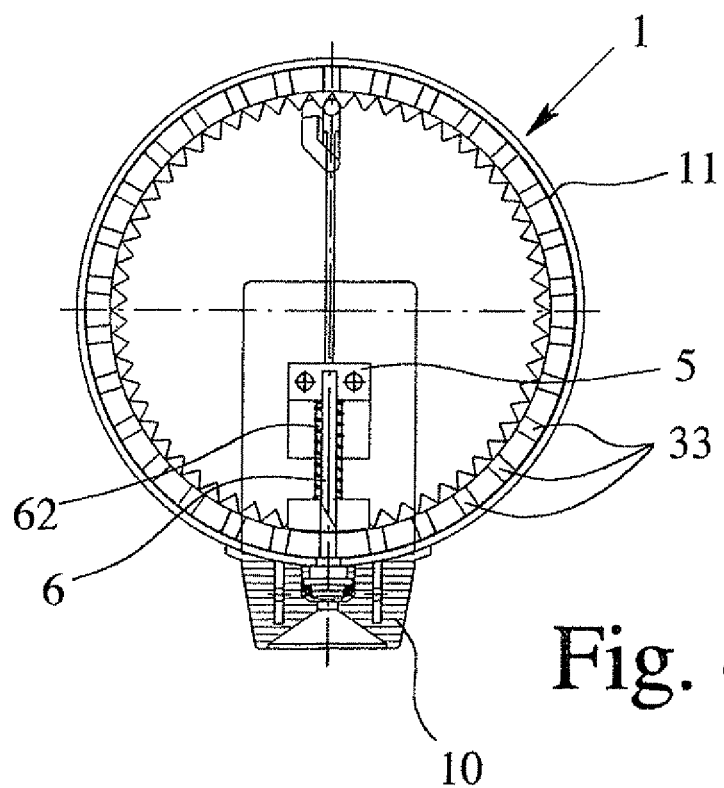
FIG. 46 shows a schematic section through the inhaler according to another embodiment in a second state.

FIGS. 45 and 46 schematically show another embodiment of the inhaler 1. Instead of separate capsules 3, the formulation 2 is pre-dosed directly into receptacles 33 in the carrier 11. Thus, the receptacles 33 preferably form capsules in the sense of the present invention. The carrier 11 preferably forms a ring, the receptacles 33 being distributed around its circumference and closed off.

The receptacles 33 can be opened individually by means of the again preferably radially acting opening device 5 by pulling the mouthpiece 10 radially outwards. This causes the opening device 5 which is coupled to the mouthpiece 10, particularly by a carriage, to move radially as well, so that the piercing element 6 engages in the receptacle 33 located in the position of inhalation and aligned with the piercing element 6, and the formulation 2 contained therein is pushed out or expelled radially outwards into the adjoining chamber 63. This situation is illustrated in FIG. 45.

Subsequently, during the inhalation, the formulation 2 is expelled from the chamber 63 through the mouthpiece 10 by means of the air flow. Then the mouthpiece 10 can be pushed relatively back again. This situation is shown in FIG. 46. Moreover, in this way, piercing element 6 is withdrawn from the receptacle 33 which has previously been pierced or emptied.

Finally, the carrier 11 is advanced or rotated by one receptacle 33. This can be done for example using the internal teeth shown, while the mouthpiece 10 is pushed fully inwards and/or initially pulled outwards.

Generally, an inhaler 1 is proposed for the inhalation of a formulation 2 from capsules 3, each of which contains one dose of the formulation 2. The capsules 3 are each preferably emptied in a capsule chamber 4 by being set in motion by a stream of gas or air flowing through the capsule chamber 4. The stream of gas or air can be produced by the breathing of a user or patient and/or actively by the inhaler 1. For ease of operation the inhaler 1 comprises, in particular, means for in particular automatically filling, emptying and/or cleaning the capsule chamber 4, if it is used more than once. Alternatively the inhaler 1 comprises a plurality of capsule chambers 4, each of which preferably already contains a capsule 3 and is preferably used only once.

The dispersing process preferably used (movement of the opened capsule 3 in a current of gas or air in order to expel and disperse the formulation 2 in the current of gas or air) has various advantages. It allows very uniform dispersion with good breaking up of the particles. A relative flow rate independence is made possible. In particular the capsule movement or vibration and hence the delivery of the formulation begins after about a flow rate of 10 or 20 l/min moreover, an acoustic signal perceptible to the user may be produced by the movement of the capsule, i.e. during inhalation.

Furthermore, the inhaler 1 may be provided with means for cleaning the mouthpiece 10. Alternatively, or in addition, the mouthpiece 10 may be removable particularly for cleaning.

If there are a number of capsule chambers 4, the inhaler 1 may have a retaining or clamping device (not shown) for fixing the capsule chambers 4 in the inhalation position, by frictional knocking and/or interlocking engagement. The retaining or clamping device may act for example on the longitudinal side of the capsule chamber 4, so as to preserve the inlet 8 and outlet 9 for the supply and removal of air. Alternatively, or in addition, the capsule chamber 4 may also be secured at its axial end regions, particularly at the inlet 8 and outlet 9, by clamping or frictional and/or interlocking engagement.

The capsules 3 shown in the embodiment by way of example are preferable cylindrical or elongate, particularly with rounded ends. However, in theory, the capsules 3 may have or assume any desired shape.

If necessary, the capsule reservoir 31 may also be constructed to be rotatable, particularly if it has discrete receiving chambers for the capsules 3 or corresponding followers for the capsules 3. The capsules 3 can then be moved accordingly into a delivery position from which they can be expelled, in particular, individually into the associated capsule chamber 4 or into some other handling or conveying device.

In the embodiments and variants described, the capsule chambers 4, carrier 11, capsule reservoir 31 or the like are preferably opened automatically. Additionally or as an alternative it is also possible for a cover, seal or the like to have to be opened manually, particularly when the inhaler 1 is used for the first time, for example by pulling it out sideways.

According to another alternative embodiment (not shown) the reservoir 31 for the capsules 3 or capsule chambers 4 may also be constructed so as to be suitable for fitting or coupling to the inhaler 1 for refilling the inhaler 1. In particular, the reservoir 31 is then opened automatically to transfer the capsules 3 or capsule chambers 4 to the inhaler 1.

To actuate the inhaler it is also possible for the mouthpiece 10 to be movable preferably axially or in the direction of exit, particularly manually. This may be used for filling or emptying the associated capsule chamber 4, for opening or piercing the capsule 3, particularly axially or in the longitudinal direction, and/or for opening/closing an outlet valve or the like which is preferably provided in the mouthpiece 10.

Generally, any desired drive may be used for conveying or further transporting the capsules 3 and/or capsule chambers 4. It is particularly preferable to have a purely mechanical and in particular manually operated drive. If necessary, spring means may be used. Thus it is possible, for example, to use a biased spring, such as a spiral spring, watch spring or the like, for further conveying the carrier 11 or for conveying and/or winding up the capsules 3, capsule chambers 4 or guide element 21 that form in particular a strip or a chain.

The proposed inhaler 1 is preferably provided with a locking or securing device to prevent unauthorised use, particularly a child lock or the like.

In addition the inhaler 1 may also have a locking mechanism such as a ratchet mechanism or the like to prevent conveying of the capsules 3, capsule chambers 4, carrier 11, guide element 21 or a chain or strip of the like formed thereby, in the opposite direction.

The proposed inhaler 1 is designed in particular to hold at least 30 capsules or more. For daily inhalation of one dose the inhaler thus holds one month's supply.

Individual features and aspects of the various embodiments can also be combined with one another as desired or used in inhalers of other designs.

The present invention is not restricted to inhalers, but can also be used accordingly in other atomisers. Therefore the term "inhaler" is preferably to be understood in the wider sense as meaning that it also encompasses other dispensers or atomisers, particularly for medicinal or other therapeutic purposes.

Some preferred ingredients and/or compositions of the preferred medicinal formulation 2 are listed below. As mentioned previously, these are powders, in particular, or fluids in the widest sense. Particularly preferably, the formulation 2 contains the following:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

- W denotes a betamimetic, combined with an anticholinergic, corticosteroid, PDE4-inhibitor, EGFR-inhibitor or LTD4-antagonist,
- W denotes an anticholinergic, combined with a betamimetic, corticosteroid, PDE4-inhibitor, EGFR-inhibitor or LTD4-antagonist,
- W denotes a corticosteroid, combined with a PDE4-inhibitor, EGFR-inhibitor or LTD4-antagonist
- W denotes a PDE4-inhibitor, combined with an EGFR-inhibitor or LTD4-antagonist
- W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide
5-[2-(5,6-diethyl-indan-2-ylamino)-1-hydroxy-ethyl]-8-hydroxy-1H-quinolin-2-one
4-hydroxy-7-[2-{[2-{[3-(2-phenylethoxy)propyl]sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2,4,6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1.1 dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

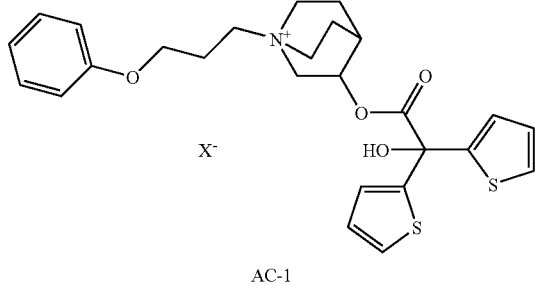 [SMILES: O=C(OC1C[N+]2(CCCOc3ccccc3)CCC1CC2)C(O)(c1cccs1)c1cccs1]

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

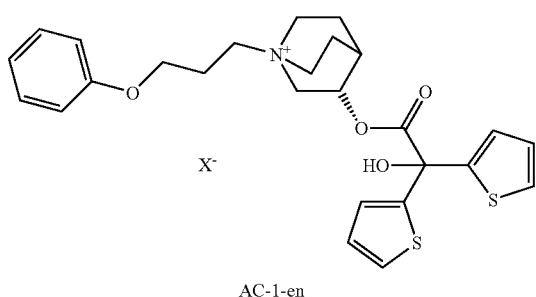

AC-1-en wherein $X^-$ may have the above-mentioned meanings. Other preferred anticholinergics are selected from the salts of formula AC-2

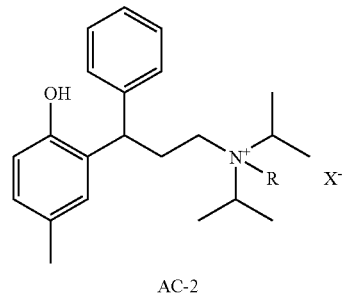

AC-2 wherein R denotes either methyl or ethyl and wherein $X^-$ may have the above-mentioned meanings. In an alternative embodiment the compound of formula AC-2 may also be present in the form of the free base AC-2-base.

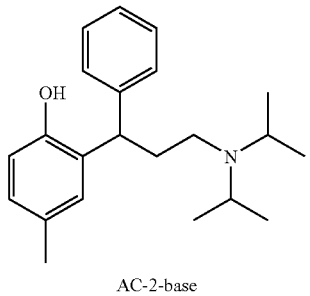 [SMILES: Cc1ccc(O)c(C(CCN(C(C)C)C(C)C)c2ccccc2)c1]

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;

tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and

- (S)-fluoromethyl 6,9-difluoro-17-[(2-furanylcarbonyl)oxy]-1,1-hydroxy-16-methyl-3-oxo-androsta-1,4-diene-17-carbothionate
- (S)-(2-oxo-tetrahydro-furan-3S-yl)6,9-difluoro-1,1-hydroxy-16-methyl-3-oxo-17-propionyloxy-androsta-1,4-diene-17-carbothionate,
- cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophylline, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and

- N-(3,5-dichloro-1-oxo-pyridin-4-yl)-4-difluoromethoxy-3-cyclopropylmethoxybenzamide
- (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
- (R)-(+)-1-(4-bromobenzyl)-4-[(3-cyclopentyloxy)-4-methoxyphenyl]-2-pyrrolidone
- 3-(cyclopentyloxy-4-methoxyphenyl)-1-(4-N'-[N-2-cyano-S-methyl-isothioureido]benzyl)-2-pyrrolidone
- cis[4-cyano-4-(3-cyclopentyloxy-4-methoxyphenyl)cyclohexane-1-carboxylic acid]
- 2-carbomethoxy-4-cyano-4-(3-cyclopropylmethoxy-4-difluoromethoxy-phenyl)cyclohexan-1-one
- cis[4-cyano-4-(3-cyclopropylmethoxy-4-difluoromethoxyphenyl)cyclohexan-1-ol]
- (R)-(+)-ethyl[4-(3-cyclopentyloxy-4-methoxyphenyl)pyrrolidin-2-ylidene]acetate
- (S)-(−)-ethyl[4-(3-cyclopentyloxy-4-methoxyphenyl)pyrrolidin-2-ylidene]acetate
- 9-cyclopentyl-5,6-dihydro-7-ethyl-3-(2-thienyl)-9H-pyrazolo[3,4-c]-1,2,4-triazolo[4,3-a]pyridine
- 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and

- 1-(((R)-(3-(2-(6,7-difluoro-2-quinolinyl)ethenyl)phenyl)-3-(2-(2-hydroxy-2-propyl)phenyl)thio)methylcyclopropane-acetic acid,
- 1-(((1(R)-3 (3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid
- [2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and

- 4-[(3-chloro-4-fluorophenyl)amino]-6-{[4-(morpholin-4-yl)-1-oxo-2-buten-1-yl]-amino}-7-cyclopropylmethoxy-quinazoline
- 4-[(3-chloro-4-fluorophenyl)amino]-6-{[4-(N,N-diethylamino)-1-oxo-2-buten-1-yl]amino}-7-cyclopropylmethoxy-quinazoline
- 4-[(3-chloro-4-fluorophenyl)amino]-6-{[4-(N,N-dimethylamino)-1-oxo-2-buten-1-yl]amino}-7-cyclopropylmethoxy-quinazoline
- 4-[(R)-(1-phenyl-ethyl)amino]-6-{[4-(morpholin-4-yl)-1-oxo-2-buten-1-yl]-amino}-7-cyclopentyloxy-quinazoline
- 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline
- 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline
- 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline
- 4-[(3-chloro-4-fluoro-phenyl)amino]-6-[2-((S)-6-methyl-2-oxo-morpholin-4-yl)-ethoxy]-7-methoxy-quinazoline
- 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline
- 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluorophenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluorophenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-[1-(tetrahydropyran-4-yloxy]-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino]-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimethindene, clemastine, bamipine, dexchlorpheniramine, pheniramine, doxylamine, chlorphenoxamine, dimenhydrinate, diphenhydramine, promethazine, ebastine, desloratidine and meclizine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, inhalable macromolecules mb used, as disclosed in EP 1 003 478 A1 or CA 2297174 A1.

In addition, the compound may come from the group of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

| List of reference numerals | |
|---|---|
| 1 | inhaler |
| 2 | formulation |
| 3 | capsule |
| 4 | capsule chamber |
| 5 | opening device |
| 6 | piercing element |
| 6a | additional piercing element |
| 7 | piercing opening |
| 8 | inlet |
| 9 | outlet |
| 10 | mouthpiece |
| 11 | carrier |
| 12 | cover |
| 12a | cover portion |
| 13 | lattice |
| 14 | lower housing part |
| 15 | upper housing part |
| 16 | connecting member |
| 17 | spring (connecting member) |
| 18 | insert |
| 18a | first roller |
| 18b | second roller |
| 18c | ring |
| 18d | opening element |
| 18e | collecting container |
| 18f | groove |
| 18g | slide |
| 18h | projection |
| 18i | cam |
| 19 | insert |
| 20 | guide |
| 20a | track |
| 21 | guide element |
| 21a | engaging element |
| 22 | taper |
| 23 | first receiving chamber |
| 24 | second receiving chamber |
| 25 | filling device |
| 25a | conveying element |
| 26 | capsule chamber part |
| 27 | mechanism |
| 28 | control slide |
| 29 | pivoting device |
| 29a | sun wheel |
| 29b | gear wheel |
| 30 | pivot axis |
| 31 | capsule reservoir |
| 32 | cleaning device |
| 33 | receptacle |
| 34 | conveying device |
| 35 | control sleeve |
| 36 | transmission |
| 37 | positioning wheel |
| 38 | guide |
| 39 | push rod |
| 40 | resetting element |
| 41 | drive wheel |
| 42 | partition wall |
| 43 | covering cap |
| 44 | strip |
| 45 | channel |
| 46 | counter |
| 47 | ring/segment |
| 48 | blister pouch |
| 49 | spring (housing) |
| 49a | spike |
| 50 | engaging hook |
| 51 | gear rim |
| 52 | locking pawl |
| 53 | actuating element |
| 54 | gate |
| 55 | opening |
| 56 | spring (gate) |
| 57 | shutter |
| 58 | holding device |
| 59 | arm |
| 60 | pin |
| 61 | stopper |

| List of reference numerals | |
|---|---|
| 62 | return spring |
| 63 | chamber |

The invention claimed is:

1. An inhaler (1) for the inhalation of a formulation (2) from capsules (3), each containing one dose of the formulation (2), wherein the inhaler (1) comprises a plurality of capsule chambers (4) containing respective capsules (3) in order to empty them during inhalation, wherein each of the capsule chambers (4) contains a respective one of the capsules (3), each capsule chamber (4) and capsule (3) can be used only once, and the capsule chambers (4) are arranged in a ring such that the capsule chambers (4) and the capsules (3) are aligned radially with respect to a central point.

2. The inhaler according to claim 1, further comprising a first ring of the capsule chambers (4) and the capsules (3) that aligned radially with respect to a first central point, and a second ring of the capsule chambers (4) and the capsules (3) that aligned radially with respect to a second central point, wherein the first and second rings are disposed one atop the other.

3. The inhaler according to claim 1, further comprising at least one annular carrier (11) within which the capsule chambers (4) and the capsules (3) are disposed.

4. The inhaler according to claim 1, wherein the capsule chambers (4) include an inlet side and an outlet side, which are closed off by a shared cover (12) at least on the inlet and/or outlet side, wherein said shared cover (12) is selected from foil, cover portions (12a), sleeves and stoppers (61).

5. The inhaler according to claim 4, wherein the cover (12) or cover portions (12a) is laminated on the carrier (11).

6. The inhaler according to claim 4, wherein the cover (12) or cover portions (12a) is used to cover respective piercing openings (7) extending in the respective capsule chambers (4).

7. The inhaler according to claim 4, wherein the capsule chambers (4) can be opened individually through the cover (12) or cover portions (12a), wherein said cover (12) or cover portions (12a) is pulled off, peeled off, unwound, wound up, pierced or cut.

8. The inhaler according to claim 7, wherein said cover (12) or cover portions (12a) is pulled off, peeled off, unwound, or wound up via at least one roller (18a, 18b).

9. The inhaler according to claim 7, wherein said cover (12) or cover portions (12a) is pulled off or peeled via a hook- or shovel-like opening element (18d).

10. The inhaler according to claim 7, wherein the capsule chambers (4) and the capsules (3) are closed in fluid-tight or gas-tight manner and/or can be opened individually.

11. The inhaler according to claim 1, wherein the capsule chamber (4) is of elongate construction and air can flow therethrough in a longitudinal direction thereof in order to empty the respective capsule (3) and/or expel the respective dose of the formulation (2).

12. The inhaler according to claim 1, wherein the capsule chambers (4) and the capsules (3) are movable for emptying after the respective capsule (3) has been opened.

13. The inhaler according to claim 1, wherein the capsules (3) can be moved back and forth or set oscillating or vibrating in the respective capsule chamber (4) in order to empty them.

14. The inhaler according to claim 1, further comprising an opening device (5) for opening the respective capsules (3)

laterally, radially axially or at an end face thereof, via piercing the capsule (3) through the capsule chamber (4).

15. The inhaler according to claim 14, wherein the capsule chamber (4) has at least one re-sealable opening (7) therethrough for receiving a piercing element (6) that pierces the capsule (3), the opening (7) being re-sealable by means of a cover (12), a cover portion (12a), a septum or a spring-loaded or elastic cover element.

16. An inhaler (1) for the inhalation of a formulation (2) from capsules (3), each containing one dose of the formulation (2), wherein the inhaler (1) comprises a plurality of capsule chambers (4) for receiving respective capsules (3) in order to empty them during inhalation, wherein each of the capsule chambers (4) contains a respective one of the capsules (3), each capsule chamber (4) and capsule (3) can be used only once, and the capsule chambers (4) are arranged in a ring such that the capsule chambers (4) and the capsules (3) are aligned radially with respect to a central point, wherein the capsule chambers (4) include an inlet side and an outlet side, which are closed off by a shared cover (12) at least on the inlet and/or outlet side, wherein said shared cover (12) is selected from foil, cover portions (12a), sleeves and stoppers (61), and wherein the cover (12) or cover portions (12a) is laminated on the carrier (11).

17. An inhaler (1) for the inhalation of a formulation (2) from capsules (3), each containing one dose of the formulation (2), wherein the inhaler (1) comprises:
   a plurality of capsule chambers (4) for receiving respective capsules (3) in order to empty them during inhalation, wherein each of the capsule chambers (4) contains a respective one of the capsules (3), each capsule chamber (4) and capsule (3) can be used only once, and the capsule chambers (4) are arranged in a ring such that the capsule chambers (4) and the capsules (3) are aligned radially with respect to a central point; and
   an opening device (5) for opening the respective capsules (3) laterally, radially axially or at an end face thereof, via piercing the capsule (3) through the capsule chamber (4).

* * * * *